United States Patent
Kim

(10) Patent No.: US 10,331,118 B2
(45) Date of Patent: Jun. 25, 2019

(54) MEDICAL DEVICE DIAGNOSTIC APPARATUS AND CONTROL METHOD THEREOF

(71) Applicant: SAMSUNG ELECTRONICS CO., LTD., Suwon-si (KR)

(72) Inventor: Sang Hoon Kim, Suwon-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 594 days.

(21) Appl. No.: 14/931,025

(22) Filed: Nov. 3, 2015

(65) Prior Publication Data

US 2016/0209837 A1 Jul. 21, 2016

(30) Foreign Application Priority Data

Jan. 21, 2015 (KR) .......................... 10-2015-0009982

(51) Int. Cl.
*G06F 11/30* (2006.01)
*G05B 23/02* (2006.01)
(Continued)

(52) U.S. Cl.
CPC .......... *G05B 23/0275* (2013.01); *A61B 5/055* (2013.01); *A61B 6/586* (2013.01);
(Continued)

(58) Field of Classification Search
None
See application file for complete search history.

(56) References Cited

U.S. PATENT DOCUMENTS

| 4,853,946 A | 8/1989 | Elliott et al. |
| 4,991,193 A | 2/1991 | Cecil et al. |

(Continued)

FOREIGN PATENT DOCUMENTS

| JP | 2009110281 A | 5/2009 |
| JP | 2011-175575 A | 9/2011 |
| KR | 1020130138987 A | 12/2013 |

OTHER PUBLICATIONS

Communication dated Dec. 11, 2015 by Korean Intellectual Property Office in related Application No. 10-2015-0009982.

(Continued)

*Primary Examiner* — Aditya S Bhat
(74) *Attorney, Agent, or Firm* — Sughrue Mion, PLLC

(57) ABSTRACT

A medical device diagnostic apparatus and a control method thereof are provided. The medical device diagnostic apparatus includes a communicator connected to a controlled medical device, the communicator being configured to transmit and receive data to and from the controlled medical device, and a controller configured to select a component from components of the controlled medical device based on the received data, calculate a difference value between input and output data of the selected component and input and output data corresponding to the selected component in reference data, determine whether the difference value is greater than a value, determine that the selected component operates abnormally in response to the controller determining that difference value is greater than the value, and select another component from the components in response to the controller determining that the difference value is less than or equal to the value.

21 Claims, 37 Drawing Sheets

(51) Int. Cl.
  *G06F 3/0484* (2013.01)
  *G06F 3/0482* (2013.01)
  *A61B 6/00* (2006.01)
  *A61B 8/00* (2006.01)
  *A61B 5/055* (2006.01)
  *G16H 40/40* (2018.01)

(52) U.S. Cl.
  CPC .............. *A61B 8/58* (2013.01); *G06F 3/0482* (2013.01); *G06F 3/04842* (2013.01); *G06F 3/04847* (2013.01); *G16H 40/40* (2018.01)

(56) References Cited

U.S. PATENT DOCUMENTS

| | | | |
|---|---|---|---|
| 5,235,510 A | | 8/1993 | Yamada et al. |
| 9,619,619 B2 * | | 4/2017 | Bewig .................. G06F 19/3406 |
| 2007/0050759 A1 * | | 3/2007 | Boing .................... G06Q 50/22 717/135 |
| 2007/0274115 A1 | | 11/2007 | Michaels et al. |
| 2008/0231269 A1 | | 9/2008 | Ookawa |
| 2013/0088452 A1 | | 4/2013 | Glaser-Seidnitzer et al. |

OTHER PUBLICATIONS

Communication dated Jun. 6, 2016, issued by the European Patent Office in counterpart European Application No. 16151929.3.
Chad A. Kinley; "Healthcare Technology: A Strategic Approach to Medical Device Management", Electronic Theses and Dissertations, East Tennessee State University, May 2012, Total 60 pages.
Communication dated Nov. 15, 2017, issued by the Korean Intellectual Property Office in corresponding Korean Application No. 10-2016-0146014.
Communication dated Jul. 27, 2017 by the Korean Intellectual Property Office in counterpart Korean Patent Application No. 10-2016-0146014.
Communication dated Oct. 4, 2016, issued by the Korean Intellectual Property Office in counterpart Korean Application No. 10-2015-0009982.
Communication dated Jan. 20, 2017, issued by the Korean Intellectual Property Office in corresponding Korean Application No. 10-2016-0146014.

* cited by examiner

MEDICAL DEVICE DIAGNOSTIC APPARATUS AND CONTROL METHOD THEREOF

CROSS-REFERENCE TO RELATED APPLICATION

This application claims priority from Korean Patent Application No. 10-2015-0009982, filed on Jan. 21, 2015 in the Korean Intellectual Property Office, the disclosure of which is incorporated herein by reference in its entirety.

BACKGROUND

1. Field

Apparatuses and methods consistent with exemplary embodiments relate to a medical device diagnostic apparatus for determining a malfunctioning component among components of a medical device.

2. Description of the Related Art

A medical device is an apparatus for diagnosing, preventing, controlling, treating, or reducing a patient's diseases or disabilities using instruments, tools, substances, materials, etc. Examples of the medical device include an ultrasonic imaging apparatus, an X-ray imaging apparatus, a magnetic resonance imaging (MRI) apparatus, a computed tomography (CT) apparatus, and a microfluidics device.

If a component of a medical device malfunctions, the corresponding component may be replaced with a new one to normally operate the medical device. However, because there are difficulties in finding such a malfunctioning component, and most of components of a medical device are expensive, it takes much time and high cost to replace a component determined to malfunction with a new one.

SUMMARY

Exemplary embodiments may address at least the above problems and/or disadvantages and other disadvantages not described above. The exemplary embodiments are not required to overcome the disadvantages described above, and may not overcome any of the problems described above.

One or more exemplary embodiments include a medical device diagnostic apparatus for diagnosing a malfunction of a medical device by operating the medical device after replacing a plurality of components of the medical device with virtual components, and a method of controlling the medical device diagnostic apparatus.

According to an aspect of an exemplary embodiment, a medical device diagnostic apparatus includes a medical device diagnostic apparatus including a communicator connected to a controlled medical device, the communicator being configured to transmit and receive data to and from the controlled medical device, and a controller configured to select a component from components of the controlled medical device based on the received data, calculate a difference value between input and output data of the selected component and input and output data corresponding to the selected component in reference data, determine whether the difference value is greater than a value, determine that the selected component operates abnormally in response to the controller determining that difference value is greater than the value, select another component from the components in response to the controller determining that the difference value is less than or equal to the value, and calculate another difference value between input and output data of the other selected component and input and output data corresponding to the other selected component in the reference data.

The reference data may be a medical device simulation corresponding to the controlled medical device.

The medical device diagnostic apparatus may further include a storage configured to store normal input/output data being inputs and outputs of the components, and the reference data may be the normal input/output data.

The communicator may be connected to an external reference medical device corresponding to the controlled medical device, the external reference medical device operating normally, and the communicator being further configured to receive data from the external reference medical device, and the reference data may be data received from the external reference medical device.

The medical device diagnostic apparatus may further include a user interface configured to display a state of the controlled medical device, and receive a diagnosis command.

The medical device diagnostic apparatus may further include a user interface configured to display the components, and receive an input selection of the component from the components to determine whether the selected component operates abnormally.

The controller may be configured to randomly select the component from the components, the component having not been subject to determination on whether the component operates abnormally.

The medical device diagnostic apparatus may further include a user interface configured to display an inventory of the component determined to operate abnormally.

The communicator may be further configured to order the component of which the inventory is displayed.

The medical device diagnostic apparatus may further include a storage configured to store a self-replacement manual for replacing the component determined to operate abnormally, and a user interface configured to display a method of replacing the component determined to operate abnormally, based on the self-replacement manual.

The communicator may be further configured to receive data for updating the reference data from a server.

The controller may be further configured to determine one or more upper components including the components of the controlled medical device based on the received data, select a upper component from the one or more upper components, calculate a first difference value between input and output data of the selected upper component and input and output data corresponding to the selected upper component in the reference data, determine whether the first difference value is greater than the value, and determine that the selected upper component operates abnormally in response to the controller determining that the first difference value is greater than the value.

The controller may be further configured to select another upper component having not been selected from the one or more upper components in response to the controller determining that the first difference value is less than or equal to the value.

The controller may be further configured to select a lower component from one or more lower components of the upper component determined to operate abnormally, calculate a second difference value between input and output data of the selected lower component and input and output data corresponding to the selected lower component in the reference data, determine whether the second difference value is greater than the value, and determine that the selected lower component operates abnormally in response to the controller determining that the second difference value is greater than the value.

According to an aspect of another exemplary embodiment, there is provided a method of controlling a medical device diagnostic apparatus, including transmitting and receiving data to and from a controlled medical device, selecting a component from components of the controlled medical device based on the received data, calculating a difference value between input and output data of the selected component and input and output data corresponding to the selected component in reference data, determining whether the difference value is greater than a value, determining that the selected component operates abnormally in response to the determining that difference value is greater than the value, selecting another component from the components in response to the determining that the difference value is less than or equal to the value, and calculating another difference value between input and output data of the other selected component and input and output data corresponding to the other selected component in the reference data.

The reference data may be normal input/output data being inputs and outputs of the components.

The method may further include receiving data from an external reference medical device corresponding to the controlled medical device, the external reference medical device operating normally, and the reference data may be the data received from the external reference medical device.

The method may further include displaying the components, and receiving an input selection of the component from the components to determine whether the selected component operates abnormally.

The selecting the component may include randomly selecting the component from the components, the component having not been subject to determination on whether the component operates abnormally.

The method may further include displaying an inventory of the component determined to operate abnormally.

The method may further include ordering the component of which the inventory is displayed.

The method may further include displaying a method of replacing the component determined to operate abnormally, based on a self-replacement manual for replacing the component determined to operate abnormally.

The method may further include receiving data for updating the reference data from a server.

According to an aspect of another exemplary embodiment, there is provided a method of controlling a medical device diagnostic apparatus, including transmitting and receiving data to and from a controlled medical device, determining one or more upper components including components of the controlled medical device based on the received data, selecting a upper component from the one or more upper components, calculating a first difference value between input and output data of the selected upper component and input and output data corresponding to the selected upper component in reference data, determining whether the first difference value is greater than the value, and determining that the selected upper component operates abnormally in response to the determining that the first difference value is greater than the value.

The method may further include selecting another upper component having not been selected from the one or more upper components in response to the determining that the first difference value is less than or equal to the value.

The method may further include selecting a lower component from one or more lower components of the upper component determined to operate abnormally, calculating a second difference value between input and output data of the selected lower component and input and output data corresponding to the selected lower component in the reference data, determining whether the second difference value is greater than the value, and determining that the selected lower component operates abnormally in response to the determining that the second difference value is greater than the value.

According to an aspect of another exemplary embodiment, a medical device diagnostic apparatus includes a communicator configured to transmit and receive data to and from a controlled medical device, and a controller configured to select a component from components of the controlled medical device based on the received data, compare data of the selected component with reference data of the selected component, and determine whether the selected component operates abnormally based on a result of the comparison.

The controller may be further configured to select another component having not been selected from the components, compare data of the selected other component with reference data of the selected other component, and determine whether the selected other component operates abnormally based on a result of the comparison of the selected other component with the reference data of the other selected other component.

The reference data may be at least one among a simulation of the selected component, normal input/output data of the selected component, and data that is received from an external reference medical device operating normally, the data being of a component corresponding to the selected component.

BRIEF DESCRIPTION OF THE DRAWINGS

The above aspects and/or other aspects will become more apparent by describing exemplary embodiments with reference to the accompanying drawings, in which.

DETAILED DESCRIPTION

Figure 1:
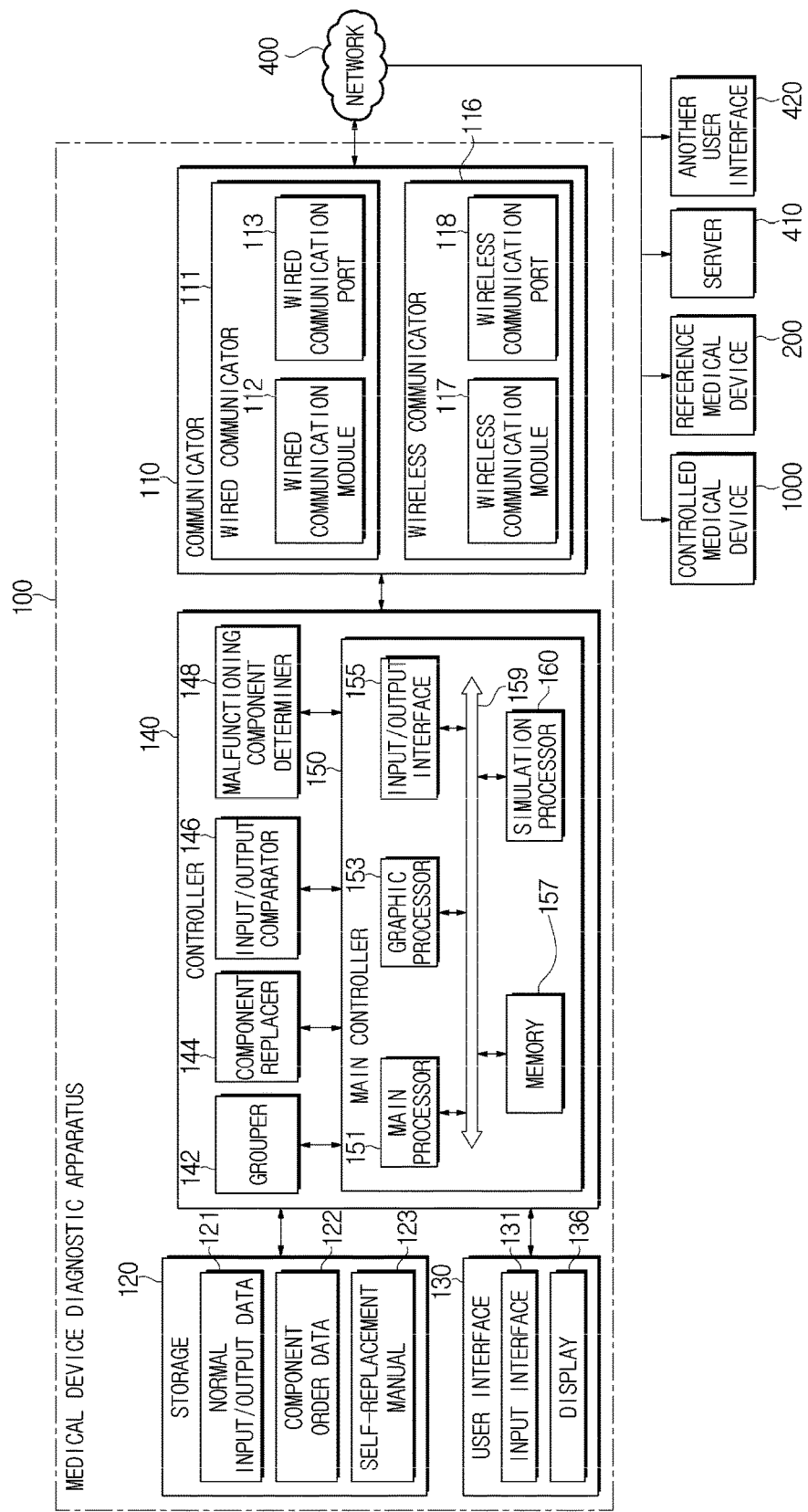
FIG. 1 is a block diagram of a medical device diagnostic apparatus according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments may be practiced without those specifically defined matters. Also, well-known functions or constructions may not be described in detail because they would obscure the description with unnecessary detail.

Figure 2:
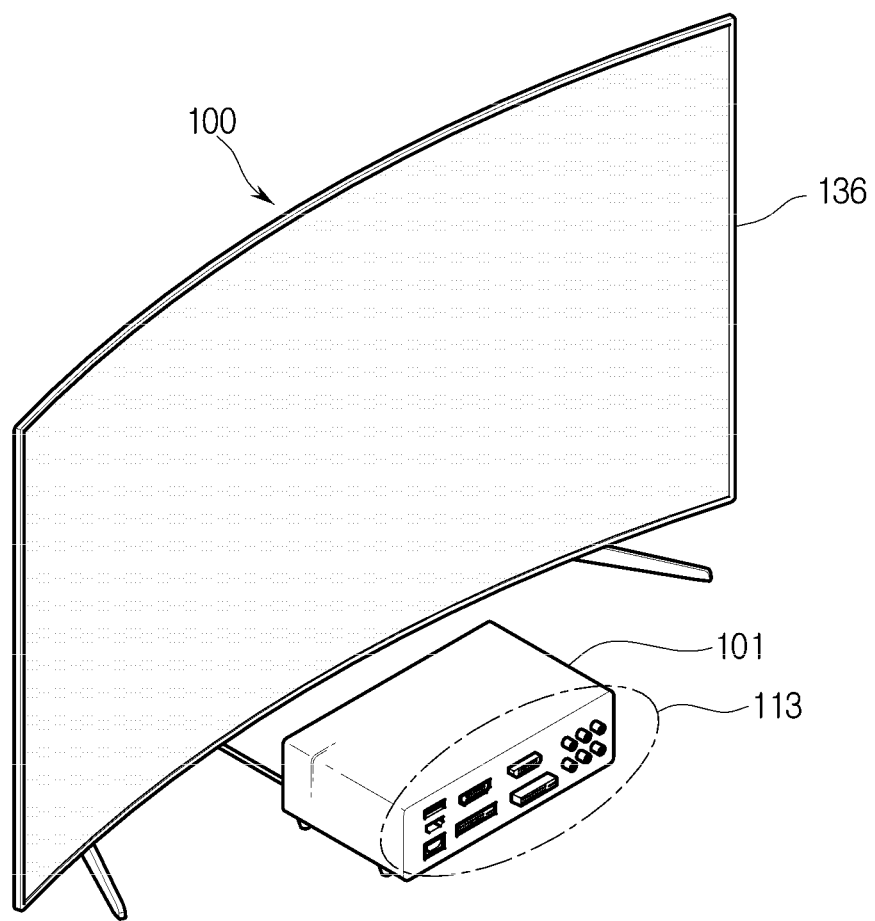
FIG. 2 is a perspective view of a medical device diagnostic apparatus according to an exemplary embodiment.
Figure 3:
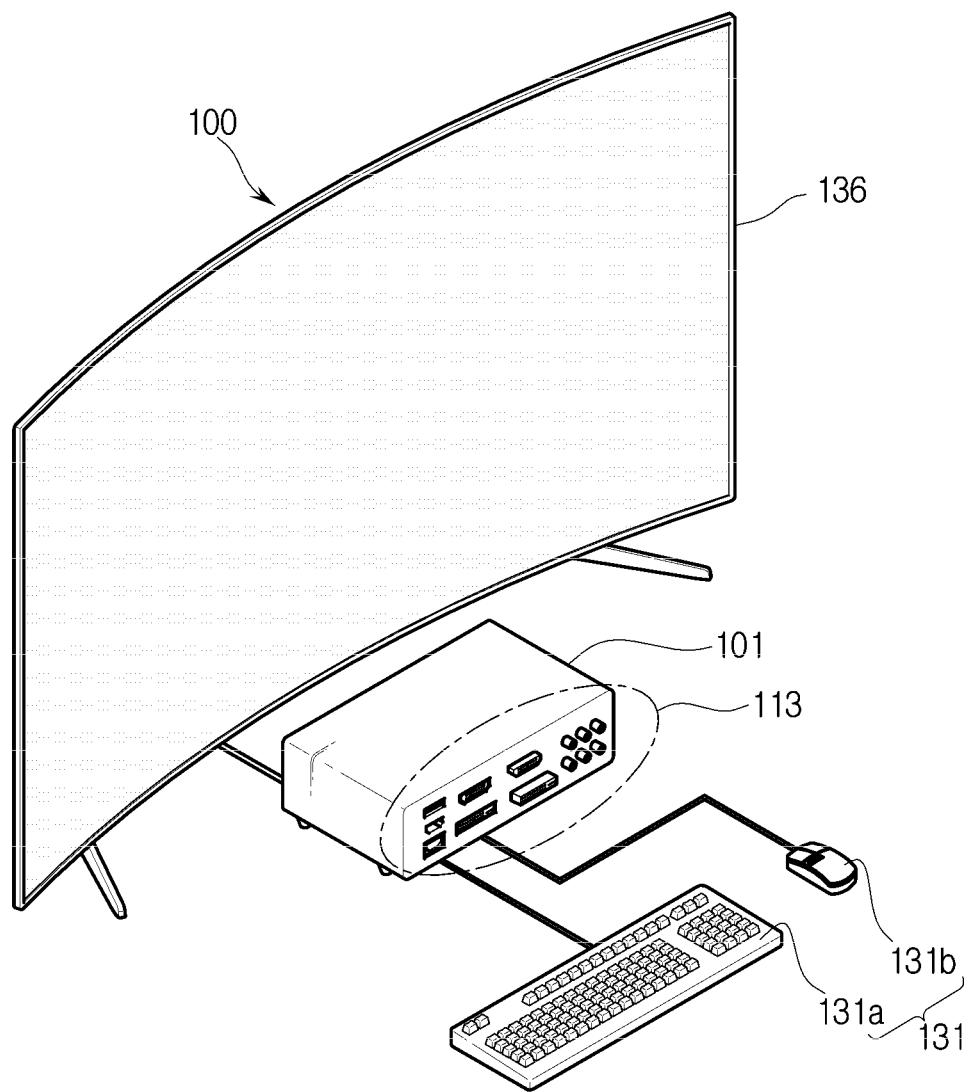
FIG. 3 is a perspective view of a medical device diagnostic apparatus according to another exemplary embodiment.

FIG. 1 is a block diagram of a medical device diagnostic apparatus according to an exemplary embodiment, FIG. 2 is a perspective view of a medical device diagnostic apparatus according to an exemplary embodiment, and FIG. 3 is a perspective view of a medical device diagnostic apparatus according to another exemplary embodiment.

Referring to FIG. 1, a medical device diagnostic apparatus 100 may be connected to a controlled medical device 1000 to determine a failure in the controlled medical device 1000, and to detect a malfunctioning component.

The medical device diagnostic apparatus 100 may be connected to the controlled medical device 1000 through a communicator 110, and replace a component of the controlled medical device 1000 with a virtual component according to reference data to compare input and output data of the component to input and output data of the virtual component, thereby determining a failure of the controlled medical device 1000 and detecting a malfunctioning component. The medical device diagnostic apparatus 100 may function as a simulation interface to connect the controlled medical device 1000 to virtual reference data. The medical device diagnostic apparatus 100 may function as a hardware and software interface to enable connections and data exchange between hardware and software.

The medical device diagnostic apparatus 100 may include the communicator 110, a storage 120, a user interface 130, and a controller 140.

The communicator 110 may transmit and receive information, etc., to and from the controlled medical device 1000 to determine a failure of the controlled medical device 1000. The communicator 110 may receive information about input and output data of components included in the controlled medical device 1000, and transfer the received information to the controller 140. The communicator 110 may transmit and receive data to and from a reference medical device 200 corresponding to the controlled medical device 1000, and transfer the received data to the controller 140. The communicator 110 may connect to the controlled medical device 1000 by a wired connection through a cable, or wirelessly through a network 400.

The communicator 110 may connect to the network 400 by a wire or wirelessly to transmit and receive data to and from the controlled medical device 1000, the reference medical device 200, a server 410, or another user interface 420. For example, the communicator 110 may transmit and receive data to and from the controlled medical device 1000, etc., through a Controller Area Network (CAN), a Peripheral Component Interconnect (PCI), or the Ethernet. The communicator 110 may connect to an external device or the network 400 by various communication methods.

The communicator 110 may include one or more components that communicate with the network 400. For example, the communicator 110 may include a wireless communicator 116 and a wired communicator 111.

The wireless communicator 116 may connect to the network 400 wirelessly to transfer input signals to a plurality of components included in the controlled medical device 1000 or the reference medical device 200 and to receive output signals from the plurality of components. The wireless communicator 116 may include a wireless communication port 118 and a wireless communication module 117.

The wireless communication port 118 may provide a path to a communicator 110 to transfer data from the wireless communication module 117 to the controlled medical device 1000.

The wireless communicator 117 may be paired with the communicator of the controlled medical device 1000 to transmit and receive information for identifying and setting a model number, a serial number, and/or a device Internet Protocol (IP) of the controlled medical device 1000. The wireless communication module 117 may include an antenna system, a radio frequency (RF) transceiver, at least one amplifier, a tuner, at least one oscillator, a digital signal processor, a CODEC chipset, a Subscriber Identity Module (SIM) card, a memory, etc., although the components of the wireless communication module 117 are not limited to these. The wireless communication module 117 may include an electric circuit for performing the functions of all or some of the above-described components.

Wireless communication methods may include Global System for Mobile Communication (GSM), Enhanced Data GSM Environment (EDGE), Wideband Code Division Multiple Access (WCDMA), Code Division Multiple Access (CDMA), Time Division Multiple Access (TDMA), Bluetooth, Bluetooth Low Energy (BLE), Near Field Communication (NFC), Zigbee, Wireless Fidelity (Wi-Fi, for example IEEE802.11a, IEEE802.11b, IEEE802.11g, and/or IEEE802.11n), Voice over Internet Protocol (VoIP), Wi-MAX, Wi-Fi Direct (WFD), Ultra Wide Band (UWB), Infrared Data Association (IrDA), E-mail, instant messaging, and/or proper communication protocols such as a protocol for Short Message Service (SMS), although this is not limiting.

The wired communicator 111 may connect to the network 400 by wire to transfer input signals to the plurality of components included in the controlled medical device 1000 or the reference medical device 200 and to receive output signals from the plurality of components. The wired communicator 111 may include a wired communication port 113 and a wired communication module 112.

The wired communication port 113 may provide a path to transfer data from the wired communication module 112 to the controlled medical device 1000. That is, the wired communication port 113 may connect to the controlled medical device 1000 through a communication cable to transmit and receive data to and from the controlled medical device 1000.

The wired communication port 113 may be connected to various communication cables. The wired communication port 113 may be a High-Definition Multimedia Interface (HDMI) port, a Digital Video Interface (DVI) port, a D-sub-miniature (D-sub) port, an Unshielded Twisted Pair (UTP) cable port, or a Universal Serial Bus (USB) port. The wired communication port 113 may be one of various communication ports that can transmit and receive data about inputs/outputs to and from the plurality of components included in the controlled medical device 1000 or the reference medical device 200.

The wired communication module 112 may exchange data with the controlled medical device 1000, the reference medical device 200, the server 410, or another user interface 420 to which the wired communication module 112 is connected through a communication cable. The wired communication module 112 may transfer a connection signal to the network 400 or the controlled medical device 1000, and receive a response signal from the network 400 or the controlled medical device 1000 to thus establish a session.

The wired communication module 112 may be a module for communications using electrical signals or optical signals. For wired communication, a pair cable, a coaxial cable, an Ethernet cable, etc., may be used, although the wired communication technology is not limited to these.

The storage 120 may store normal input/output data 121 about inputs/outputs corresponding to the plurality of components included in the controlled medical device 1000, component order data 122 that is used to order a new component for replacing a malfunctioning one among the components of the controlled medical device 1000, and a self-replacement manual 123 for guiding a user to replace the malfunctioning component with a new one without the aid of a professional.

The normal input/output data 121 may be pre-stored data about inputs and outputs acquired when the plurality of components included in the controlled medical device 1000 operate normally. The normal input/output data 121 may be a pre-stored ratio of output to input acquired when the plurality of components included in the controlled medical device 1000 operate normally. The normal input/output data 121 may be data experimentally acquired from a medical device operating normally, or data considered upon manufacturing or designing.

The component order data 122 may be pre-set information for ordering a malfunctioning component among the plurality of components included in the controlled medical device 1000. The component order data 122 may include information about a contact number or a home page of a store that sells the corresponding component, and a contact number of a person that manufactures and distributes the corresponding component.

The self-replacement manual 123 may be data visually and/or orally representing a method of dissembling the controlled medical device 1000, replacing a malfunctioning component among the plurality of components included in the controlled medical device 1000 with a new one, and then assembling the controlled medical device 1000.

The storage 120 may be a non-volatile memory, such as Read Only Memory (ROM), high-speed Random Access Memory (RAM), a magnetic disk storage device, and a flash memory device, or a non-volatile semiconductor memory device.

For example, the storage 120 may be a semiconductor memory device, such as a Secure Digital (SD) memory card, a Secure Digital High Capacity (SDHC) memory card, a mini SD memory card, a mini SDHC memory card, a Trans Flash (TF) memory card, a micro SD memory card, a micro SDHC memory card, a memory stick, Compact Flash (CF), a Multi-Media Card (MMC), MMC micro, and an eXtreme Digital (XD) card.

The storage 120 may be a network attached storage device to which access is made through the network 400.

The user interface 130 may display various information related to operations of the medical device diagnostic apparatus 100, and receive a user's instruction for determining a failure of the controlled medical device 1000. For example, the user interface 130 may display a list of the plurality of components included in the controlled medical device 1000, and display information about the plurality of components to enable a user to select a component that is replaced with reference data. The user interface 130 may transfer, when a user selects a component among the plurality of components, the user's selection instruction to the controller 140.

The user interface 130 may include an input interface 131 and a display 136.

The input interface 131 may include a hardware input interface, such as a keyboard 131a, and/or a mouse 131b, as shown in FIG. 3. The input interface 131 may include various buttons, switches, a track-ball, various levers, a handle, or a stick, for receiving a user's inputs. Also, the input interface 131 may include a foot switch and a foot pedal.

The input interface 131 may include a Graphic User Interface (GUI) such as a touch pad, for receiving a user's inputs. The touch panel may include a Touch Screen Panel (TSP), and configure an inter-layer structure together with the display 136.

The display 136 may include a Cathode Ray Tube (CRT), a Digital Light Processing (DLP) panel, a Plasma Display Panel (PDP), a Liquid Crystal Display (LCD) panel, an Electro Luminescence (EL) panel, an Electrophoretic Display (EPD) panel, an Electrochromic Display (ECD) panel, a Light Emitting Diode (LED) panel, or an Organic LED (OLED) panel, although this is not limiting.

If the display 136 is configured with a TSP, the display 136 may be used as an input device, as well as a display device.

The controller 140 may control operations of the medical device diagnostic apparatus 100. The controller 140 may compare input and output data of the controlled medical device 1000 received through the communicator 110 to reference input and output data to determine whether the controlled medical device 1000 operates normally. The controller 140 may select a component among the plurality of components included in the controlled medical device 1000, and operate the controlled medical device 1000 using reference input and output data corresponding to the selected component. The controller 140 may group the plurality of components included in the controlled medical device 1000 into a plurality of groups, that is, upper groups and lower groups.

The controller 140 may include a main controller 150, a grouper 142, a component replacer 144, an input/output comparator 146, and a malfunctioning component determiner 148.

The main controller 150 may control operations of the medical device diagnostic apparatus 100.

The main controller 150 may transfer reference data corresponding to the plurality of components included in the controlled medical device 1000 to the component replacer 144. The main controller 150 may receive data from the controlled medical device 1000, and transfer the received data to the grouper 142. The main controller 150 may load the normal input/output data 121, the component order data 122, and the self-replacement manual 123 from the storage 120 to use the loaded data to control the medical device diagnostic apparatus 100.

The main controller 150 may include an input/output interface 155 to enable data transmission/reception to and from various components included in the medical device diagnostic apparatus 100, a memory 157 to store programs and data, a graphic processor 153 to perform image processing, a main processor 151 to perform operations according to the programs and data stored in the memory 157, a simulation processor 160 to create a virtual medical device corresponding to the controlled medical device 1000, and a system bus 159 that is used as a passage for data transmission/reception between the input/output interface 155, the memory 157, the graphic processor 153, and the main processor 151.

The input/output interface 155 may receive the normal input/output data 121, the component order data 122, and the self-replacement manual 123 stored in the storage 120, a user's instructions sensed by the input interface 131, and information about a malfunctioning component determined by the malfunctioning component determiner 148, and transmit the received information to the main processor 151, the graphic processor 153, and the memory 157 through the system bus 159.

The input/output interface 155 may transfer various control signals output from the main processor 151 to the grouper 142, the component replacer 144, the input/output comparator 146, the communicator 110, the storage 120, and the user interface 130.

The memory 157 may load control programs and control data for controlling operations of the medical device diagnostic apparatus 100 from the storage 120 and store the control programs and control data. The memory 157 may temporarily store reference data generated by the simulator processor 160.

The memory 157 may be a volatile memory, such as SRAM or DRAM, although this is not limiting. In some cases, the memory 157 may be a non-volatile memory, such as flash memory, ROM, EPROM, or EEPROM.

The graphic processor 153 may create an image and a manual image corresponding to a component of the controlled medical device 1000, and change the resolution or size of the image.

The main processor 151 may process information received from the malfunctioning component determiner 148 according to the programs and data stored in the memory 157, or may perform operation for displaying a malfunctioning component.

For example, the main processor 151 may recognize a component determined as a malfunctioning component among the plurality of components included in the controlled medical device 1000, and control the display 136 to display a name and appearance of the component.

The main processor 151 may generate control signals for controlling the controller 140, the storage 120, the user interface 130, and the communicator 110, and transfer the control signals to the respective components.

Referring to FIGS. 2 and 3, the medical device diagnostic apparatus 100 may include a housing 101, and at one side of the housing 101 may be installed various kinds of wired communication ports 113 that can be connected to the controlled medical device 1000 through a cable.

The simulation processor 160 may include a program for configuring a virtual device corresponding to the controlled medical device 1000 or virtual components corresponding to the plurality of components included in the controlled medical device 1000. The simulation processor 160 may acquire data in which a user is interested by configuring a virtual controlled medical device 1000.

Figure 4:
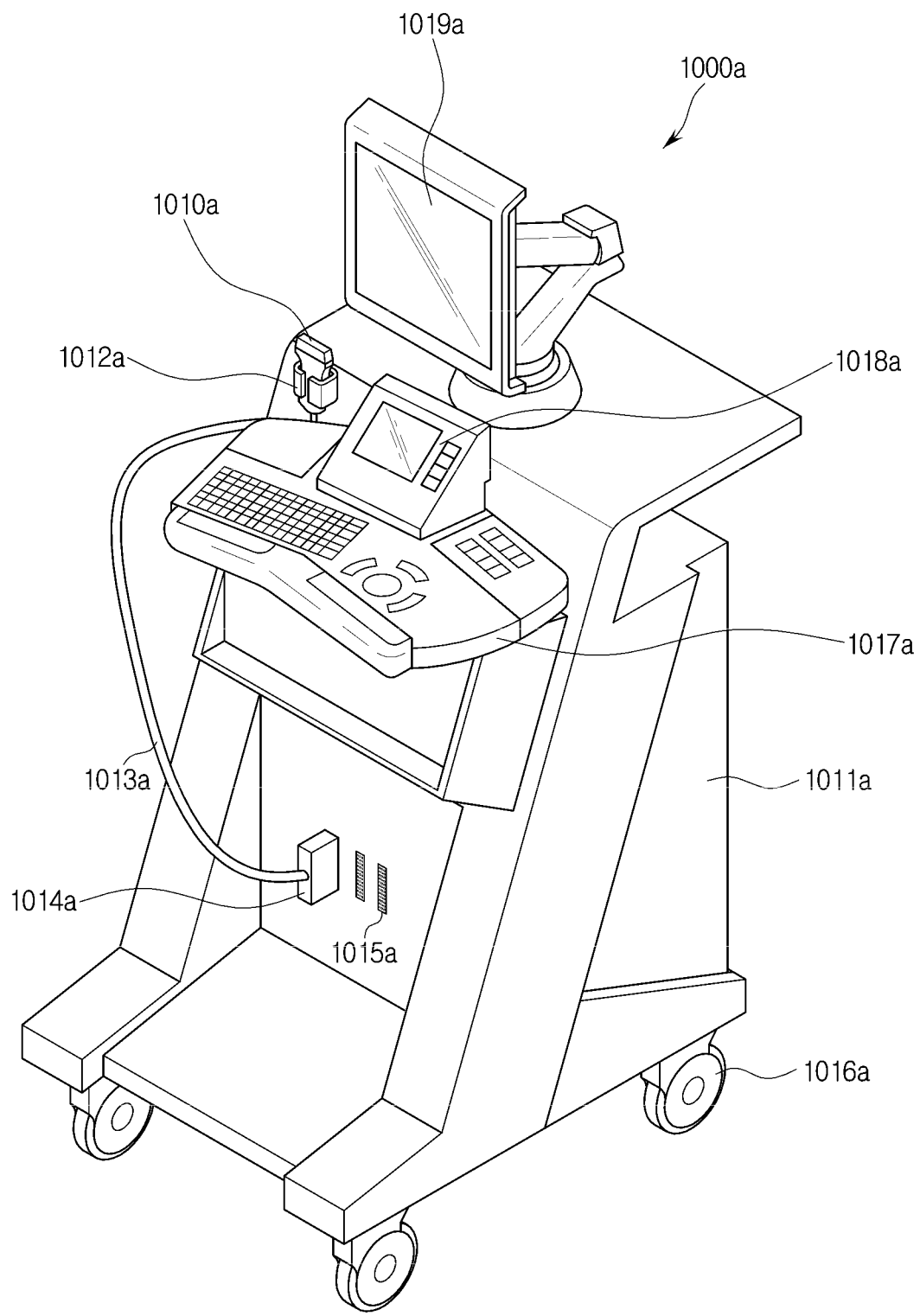
FIG. 4 is a perspective view of an ultrasonic imaging apparatus that is a controlled medical device, according to an exemplary embodiment.
Figure 5:
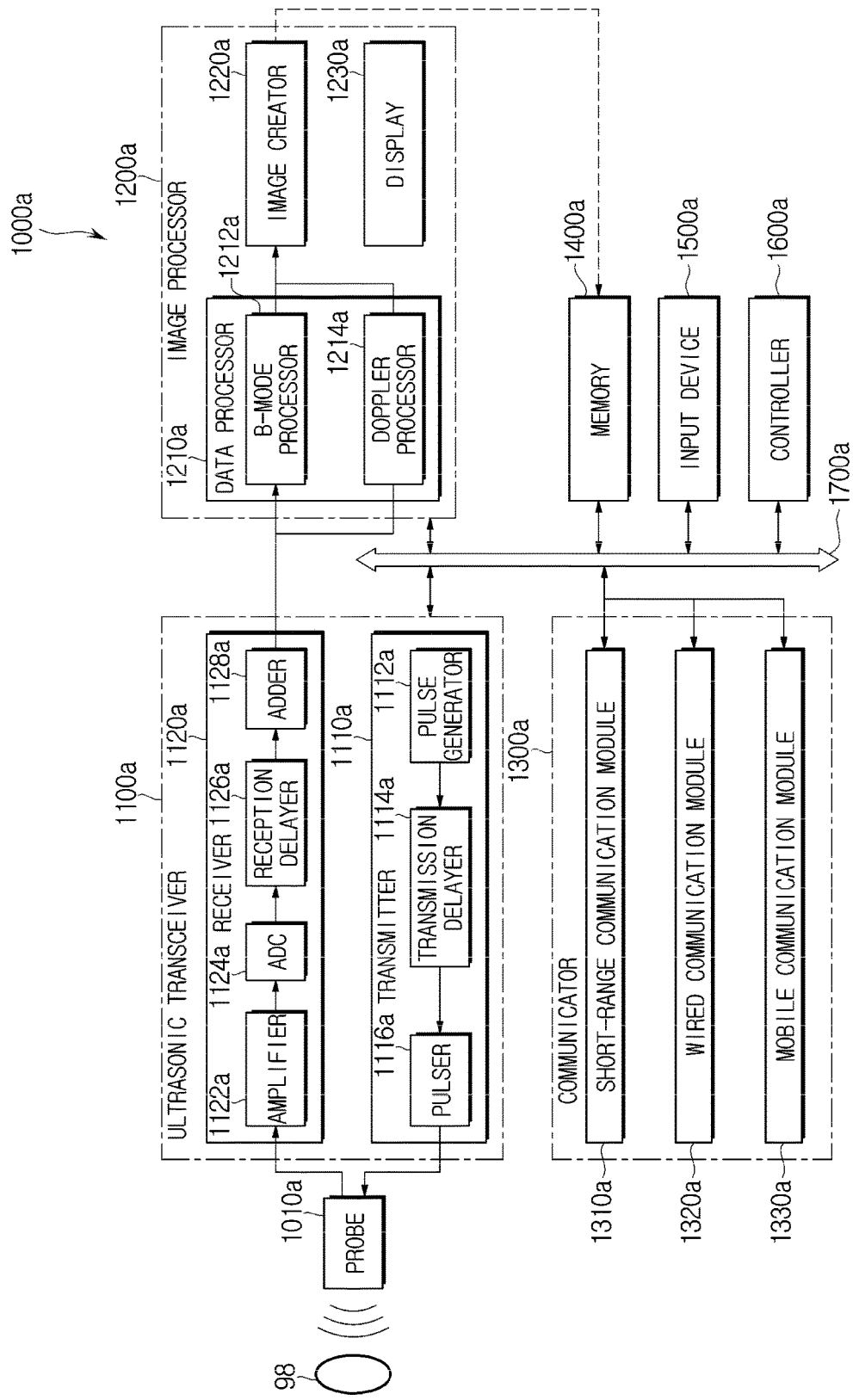
FIG. 5 is a block diagram of an ultrasonic imaging apparatus that is a controlled medical device, according to an exemplary embodiment.

For example, referring to FIGS. 4 and 5, when an ultrasonic imaging apparatus 1000a is connected as the controlled medical device 1000 to the medical device diagnostic apparatus 100, the simulation processor 160 may simulate an output from a transmitter 1110a with respect to an input received by a receiver 1120a to acquire input and output data of an ultrasonic transceiver 1100a.

Referring again to FIG. 1, the grouper 142 may group the plurality of components included in the controlled medical device 1000 to create a plurality of upper groups each including a plurality of components. The component replacer 144 may replace a component selected among the plurality of components included in the controlled medical device 1000 with reference data corresponding to the selected component. The input/output comparator 146 may compare input and output data of the component selected among the plurality of components of the controlled medical device 1000 to reference input and output data corresponding to the selected component. If it is determined that a difference between the input and output data of the selected component and the reference input and output data is greater than a predetermined value, the malfunctioning component determiner 148 may determine that the selected component operates abnormally.

Figure 6:
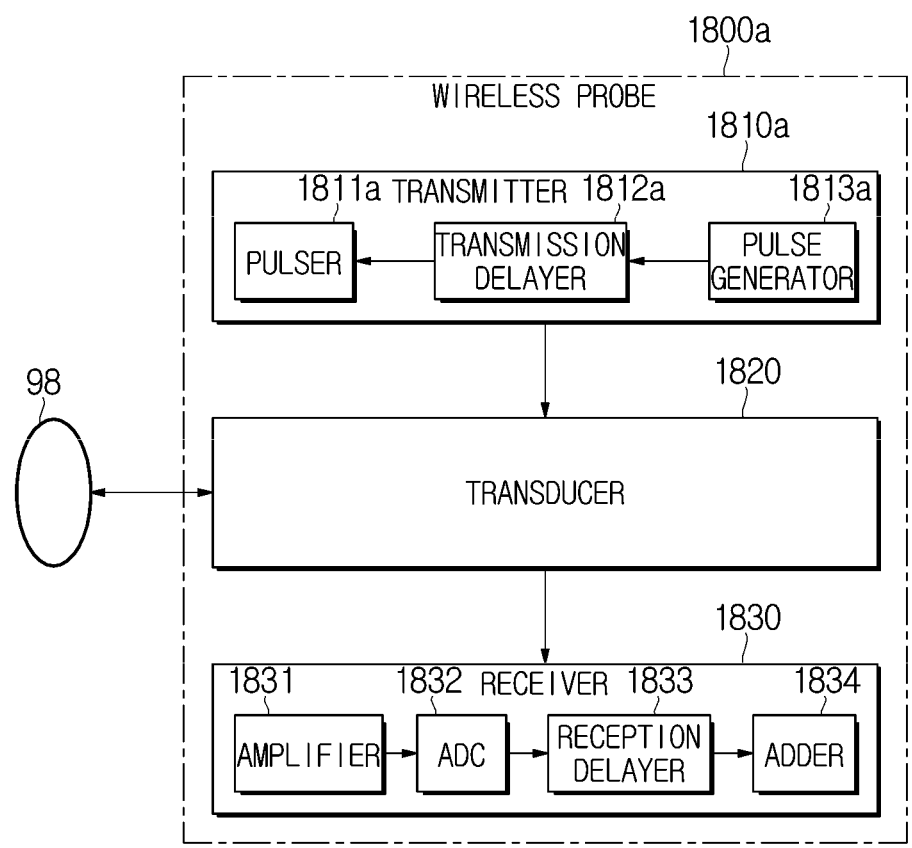
FIG. 6 is a block diagram of a wireless probe of an ultrasonic imaging apparatus that is a controlled medical device, according to an exemplary embodiment.

FIG. 4 is a perspective view of an ultrasonic imaging apparatus that is a controlled medical device, according to an exemplary embodiment. FIG. 5 is a block diagram of an ultrasonic imaging apparatus that is a controlled medical device, according to an exemplary embodiment. FIG. 6 is a block diagram of a wireless probe of an ultrasonic imaging apparatus that is a controlled medical device, according to an exemplary embodiment.

Referring to FIG. 4, the ultrasonic imaging apparatus 1000a may include a main body 1011a, an ultrasound probe 1010a, an input interface 1017a, a sub display 1018a, and a main display 1019a.

The main body 1011a may accommodate a transmission signal generator of the ultrasonic imaging apparatus 1000a. If a user inputs an ultrasonic diagnosis command, the transmission signal generator may generate a transmission signal, and transmit the transmission signal to the ultrasound probe 1010a.

At one side of the main body 1011a may be disposed one or more female connectors 1015a. A male connector 1014a connected to a cable 1013a may be physically coupled with one of the female connectors 1015a. The transmission signal generated by the transmission signal generator may be transferred to the ultrasound probe 1010a via the male connector 1014a connected to the female connector 1015a and the cable 1013a.

A plurality of castors 1016a for moving the ultrasonic imaging apparatus 1000a may be provided at the bottom of the main body 1011a. The plurality of castors 1016a may fix the ultrasonic imaging apparatus 1000a at a location, or move the ultrasonic imaging apparatus 1000a in a direction.

The ultrasound probe 1010a may contact an object to transmit or receive ultrasonic waves. The ultrasound probe 1010a may convert signals received from the main body 1011a into ultrasonic signals, irradiate the converted ultrasonic signals to an object 98, receive ultrasonic echo signals reflected from a part of the object 98, and then transmit the received ultrasonic echo signals to the main body 1011a.

To perform the operation, a plurality of acoustic modules for generating ultrasonic waves according to electrical signals may be installed at one end of the ultrasound probe 1010a.

The acoustic modules may generate ultrasonic waves according to an applied alternating current (AC) voltage. The acoustic modules may receive the AC voltage from an external power supply or an internal battery. Transducers included in the acoustic modules may vibrate according to the applied AC voltage to generate ultrasonic waves.

The plurality of acoustic modules may be arranged in an array, for example, in a linear array, or in a convex array. The plurality of acoustic modules may be arranged in a phased array, or in a concave array. Also, a cover for covering the acoustic modules may be provided.

The cable 1013a may be connected to the other end of the ultrasound probe 1010a, and the other end of the cable 1013a may be connected to the male connector 1014a. The male connector 1014a may be physically coupled with one of the female connectors 1015a of the main body 1011a.

The input interface 1017a allows a user to input commands related to operations of the ultrasonic imaging apparatus 1000a. For example, a user may use the input interface 1017a to input a mode selection command, a ultrasonic diagnosis start command, and so on, wherein modes for ultrasound images may include an amplitude mode (A-mode), a brightness mode (B-mode), a Doppler mode (D-mode), a motion mode (M-mode), and a three-dimensional (3D) mode. The commands input through the input interface 1017a may be transmitted to the main body 1011a through wired and/or wireless communication.

The input interface 1017a may include at least one of, for example, a touch pad, a keyboard, a foot switch, and a foot pedal. The touch pad or the keyboard may be implemented as hardware, and mounted on the upper portion of the main body 1011a. The keyboard may include at least one of a switch, a key, a wheel, a joystick, a trackball, and a knob. As another example, the keyboard may be implemented as software, e.g., a graphical user interface (GUI). In this case, the keyboard may be displayed through the sub display 1018a or the main display 1019a. The foot switch or the foot pedal may be provided in the lower portion of the main body 1011a, and an operator may control operations of the ultrasonic imaging apparatus 1000a using the foot switch or the foot pedal.

A probe holder 1012a for accommodating the ultrasound probe 1010a may be provided around the input interface 1017a. The operator may put the ultrasound probe 1010a into the probe holder 1012a to safely keep the ultrasound probe 1010a when the ultrasonic imaging apparatus 1000a is not in use. In FIG. 4, one probe holder 1012a is provided around the input interface 1017a, however, the probe holder 1012a may be placed at a different location, or a plurality of probe holders may be provided.

The sub display 1018a may be mounted on the main body 1011a. In FIG. 4, the sub display 1018a is provided above the input interface 1017a. The sub display 1018a may be, for example, a CRT or an LCD. The sub display 1018a may display menus or guidance for ultrasonic diagnosis.

The main display 1019a may be also mounted on the main body 1011a. In FIG. 4, the main display 1019a is positioned above the sub display 1018a. The main display 1019a may also be, for example, a CRT or a LCD. The main display 1019a may display ultrasonic images acquired during ultrasonic diagnosis. Ultrasonic images that are displayed through the main display 1019a may include at least one of a two-dimensional (2D) monochrome ultrasonic image, a 2D color ultrasonic image, a 3D monochrome ultrasonic image, and a 3D color ultrasonic image.

In FIG. 4, the ultrasonic imaging apparatus 1000a includes both the main display 1019a and the sub display 1018a, however, the sub display 1018a may be omitted, and in this case, applications or menus that are displayed through the sub display 1018a may be displayed through the main display 1019a.

Also, at least one of the sub display 1018a and the main display 1019a may be removably connected to the main body 1011a.

Referring to FIG. 5, the ultrasonic imaging apparatus 1000a may include the ultrasound probe 1010a, the ultrasonic transceiver 1100a, an image processor 1200a, a communicator 1300a, a memory 1400a, an input device 1500a, and a controller 1600a, which are connected to each other through a bus 1700a.

The ultrasonic imaging apparatus 1000a may be a cart type or a portable type. Examples of a portable-type ultrasonic imaging apparatus may include a Picture Archiving and Communication System (PACS) viewer, a smart phone, a laptop computer, personal digital assistant (PDA), and a tablet PC, although this is not limiting.

The probe 1010a may transmit ultrasonic signals to an object 98 according to a driving signal received by the ultrasonic transceiver 1100a, and receive echo signals from the object 98. The probe 1010a may include a plurality of transducers, and the plurality of transducers may vibrate according to a received electrical signal to generate ultrasonic waves that are acoustic energy. The probe 1010a may be connected to the main body 1011a of the ultrasonic imaging apparatus 1000a by a wire or wirelessly, and the ultrasonic imaging apparatus 1000a may include a plurality of probes 1010a according to its implementation type.

The ultrasonic transceiver 1110a may supply a driving signal to the probe 1010a, and may include a pulse generator 1112a, a transmission delayer 1114a, and a pulser 1116a. The pulse generator 1112a may generate pulses for forming transmission ultrasonic waves according to a predetermined Pulse Repetition Frequency (PRF), and the transmission delayer 1114a may apply delay times for deciding transmission directionality to the pulses. The respective pulses to which the delay times have been applied may correspond to a plurality of piezoelectric vibrators included in the probe 1010a, respectively. The pulser 1116a may apply driving signals (or driving pulses) which are timings corresponding to the respective pulses to which the delay times have been applied, to the probe 1010a.

The receiver 1120a may process echo signals received by the probe 1010a to generate ultrasonic data, and may include an amplifier 1122a, an Analog-to-Digital Converter (ADC) 1124a, a reception delayer 1126a, and a adder 1128a. The amplifier 1122a may amplify the echo signals for each channel, and the ADC 1124A may convert the amplified echo signals that are analog signals into digital signals. The reception delayer 1126a may apply delay times for deciding reception directionality to the digital echo signals, and the adder 1128a may sum the echo signals processed by the reception delayer 1126a to generate ultrasonic data. The receiver 1120a may not include any amplifier according to its implementation type. That is, if the probe 1010a has high sensitivity, or the ADC 1124a can process a large number of bits, the amplifier 1122a may be omitted.

The image processor 1200a may perform scan conversion on the ultrasonic data generated by the ultrasonic transceiver 1100a to generate and display an ultrasound image. The ultrasound image may be a gray scale image acquired by scanning the object 98 in the A mode, the B mode, or the M mode, or a Doppler image that represents a moving object 98 using the Doppler effect. The Doppler image may include a blood flow Doppler image (or called a color Doppler image) showing flow of blood, a tissue Doppler image showing movement of a tissue, and a spectral Doppler image showing moving speed of an object as a waveform.

The image processor 1200a may include a data processor 1210a, an image creator 1220a, and a display 1230a, and the data processor 1210a may include a B-mode processor 1212a and a Doppler processor 1214a.

The B-mode processor 1212a may extract B-mode components from the ultrasonic data. The image creator 1220a may create an ultrasound image in which signal intensities are represented by brightness levels, based on the B-mode components extracted by the B-mode processor 1212a.

Likewise, the Doppler processor 1214a may extract Doppler components from the ultrasonic data, and the image creator 1220a may create a Doppler image in which movement of an object is represented as a color or waveform, based on the Doppler components.

According to an exemplary embodiment, the image creator 1220a may perform volume rendering on volume data to create a 3D ultrasound image, or create an elastic image resulting from imaging a degree of deformation of an object according to pressure. In addition, the image creator 1220a may represent various additional information as text or graphics on the ultrasound image. The created ultrasound image may be stored in the memory 1400a.

The display 1230a may display the created ultrasound image. The display 1230a may display ultrasound images and various information that is processed by the ultrasonic imaging apparatus 1000a on a screen through a GUI. The ultrasonic imaging apparatus 1000a may include two displays or more according to its implementation type.

The communicator 1300a may be connected to a network by a wire or wirelessly to communicate with an external device or a server. The communicator 1300a may receive/transmit data from/to a hospital server or other medical apparatuses in a hospital, connected through PACS. The communicator 1300a may perform data communication according to a Digital Imaging and Communications in Medicine (DICOM) standard.

The communicator 1300a may transmit and receive data related to diagnosis of an object, such as an ultrasound image, ultrasonic data, and Doppler data of the object, through the network. The communicator 1300a may transmit and receive medical images photographed by another medical apparatus, such as a CT scanner, an MRI apparatus, an X-ray apparatus, etc., through the network. In addition, the communicator 1300a may receive information about a patient's diagnosis history, therapeutic schedule, etc., from a server, and use the information for diagnosis of an object. Furthermore, the communicator 1300a may perform data communication with a doctor's or patient's mobile terminal, as well as a server or a medical apparatus in a hospital.

The communicator 1300a may connect to the network by a wire or wirelessly to receive/transmit data from/to a server, a medical apparatus, or a mobile terminal. The communicator 1300a may include one or more components to enable communications with external devices. For example, the communicator 1300a may include a short-range communication module 1310a, a wired communication module 1320a, and a mobile communication module 1330a.

The short-range communication module 1310a may be a module for short-range communication within a predetermined distance. The short-range communication may be Wireless LAN (WLAN), Wireless-Fidelity (Wi-Fi), Bluetooth, Zigbee, Wi-Fi Direct (WFD), Ultra Wideband (UWB), Infrared Data Association (IrDA), Bluetooth Low Energy (BLE), or Near Field Communication (NFC), although this is not limiting.

The wired communication module 1320a may be a module for communication based on electrical signals or optical signals. For example, the wired communication module 1320a may be a pair cable, a coaxial cable, an optical fiber cable, or an Ethernet cable.

The mobile communication module 1330a may transmit and receive radio signals from/to at least one of a base station, an external terminal, and a server over a mobile communication network. The radio signals may include voice call signals, video call signals, or various kinds of data according to text/multimedia message transmission/reception.

The memory 1400a may store various information that is processed by the ultrasonic imaging apparatus 1000a. For example, the memory 1400a may store input/output ultrasonic data, medical data such as ultrasound images related to diagnosis of the object 98, and algorithms or programs that are executed on the ultrasonic imaging apparatus 1000a.

The memory 1400a may be one of various kinds of storage medium, such as a flash memory, a hard disk, and EEPROM. The ultrasonic imaging apparatus 1000a may operate a web storage or a cloud server that performs a storage function of the memory 1400a on the web.

The input device 1500a may receive data for controlling the ultrasonic imaging apparatus 1000a from a user. The input device 1500a may be a hardware configuration, such as a keypad, a mouse, a touch panel, a touch screen, a trackball, and a jog switch, although this is not limiting. The input device 1500a may further include various kinds of input devices, such as an electrocardiogram (ECG) measuring module, a respiration measuring module, a speech recognition sensor, a gesture recognition sensor, a fingerprint recognition sensor, an iris recognition sensor, a depth sensor, and a distance sensor.

The controller 1600a may control operations of the ultrasonic imaging apparatus 1000a. That is, the controller 1600a may control operations between the probe 1010a, the ultrasonic transceiver 1100a, the image processor 1200a, the communicator 1300a, the memory 1400a, and the input device 1500a.

The entire or a part of the probe 1010a, the ultrasonic transceiver 1100a, the image processor 1200a, the communicator 1300a, the memory 1400a, the input device 1500a, and the controller 1600a may operate by a software module, however, a part of the above-mentioned components may operate by hardware. Also, at least one of the ultrasonic transceiver 1100a, the image processor 1200a, and the communicator 1300a may be included in the controller 1600a.

Referring to FIG. 6, a wireless probe 1800a may include at least one transducer 1820, as described above with reference to FIG. 5, and may include the entire or a part of components of the ultrasonic transceiver 1100a of FIG. 5 according to its implementation type.

Referring to FIG. 6, the wireless probe 1800a may include a transmitter 1810a, the transducer 1820, and a receiver 1830. The transmitter 1810a, the transducer 1820, and the receiver 1830 have been described above with reference to FIG. 5, and accordingly, detailed descriptions thereof will be omitted. The wireless probe 1800a may selectively include a pulser 1811a, a transmission delayer 1812a, a pulse generator 1813a, an amplifier 1831, an ADC 1832, a reception delayer 1833, and an adder 1834, according to an implementation type.

The wireless probe 1800a may transmit ultrasonic signals to the object 98, receive echo signals, create ultrasound data, and transmit the ultrasound data to the ultrasonic imaging apparatus 1000a of FIG. 5 wirelessly.

Figure 7:
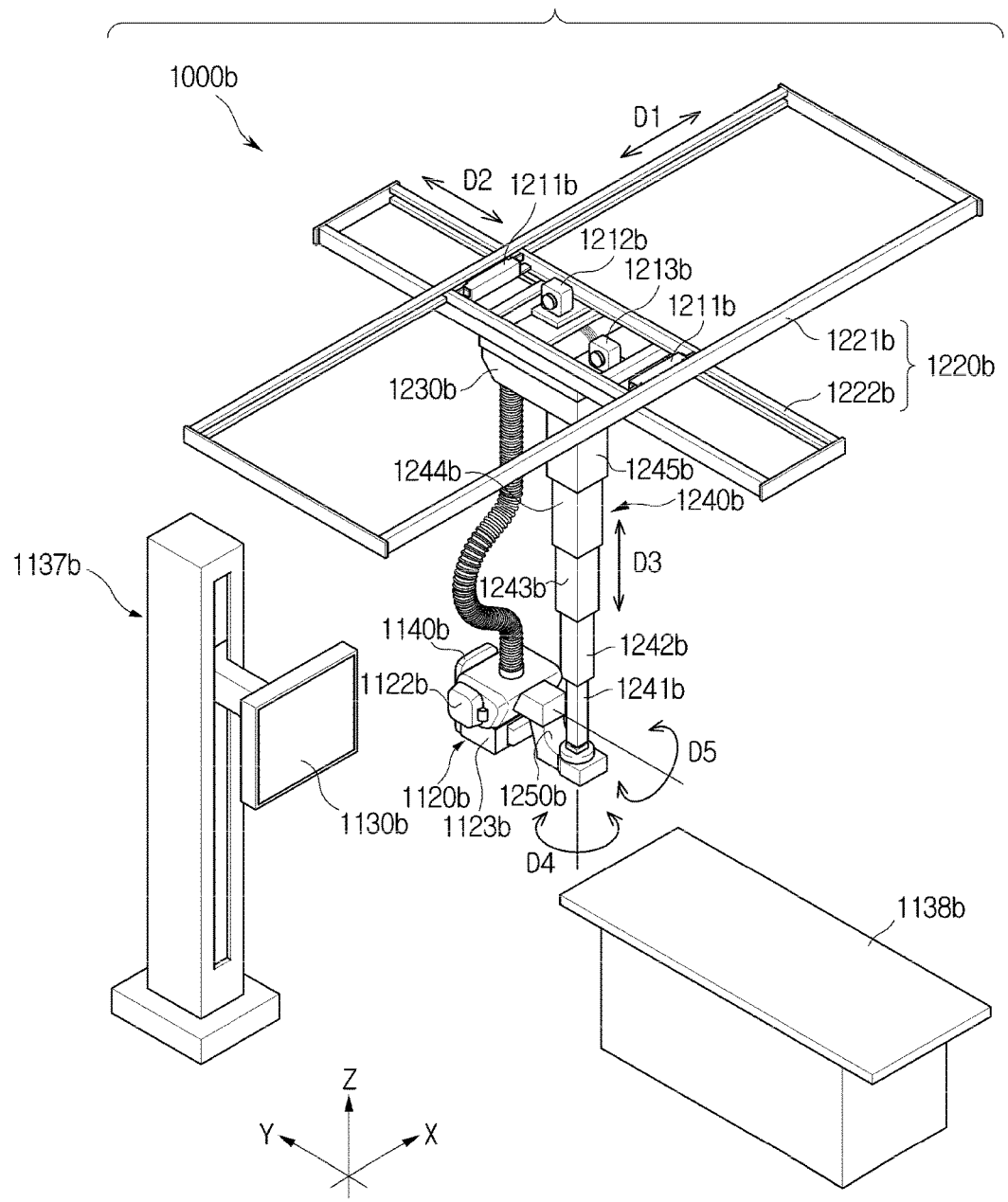
FIG. 7 is a perspective view of an X-ray imaging apparatus that is a controlled medical device, according to another exemplary embodiment.
Figure 8:
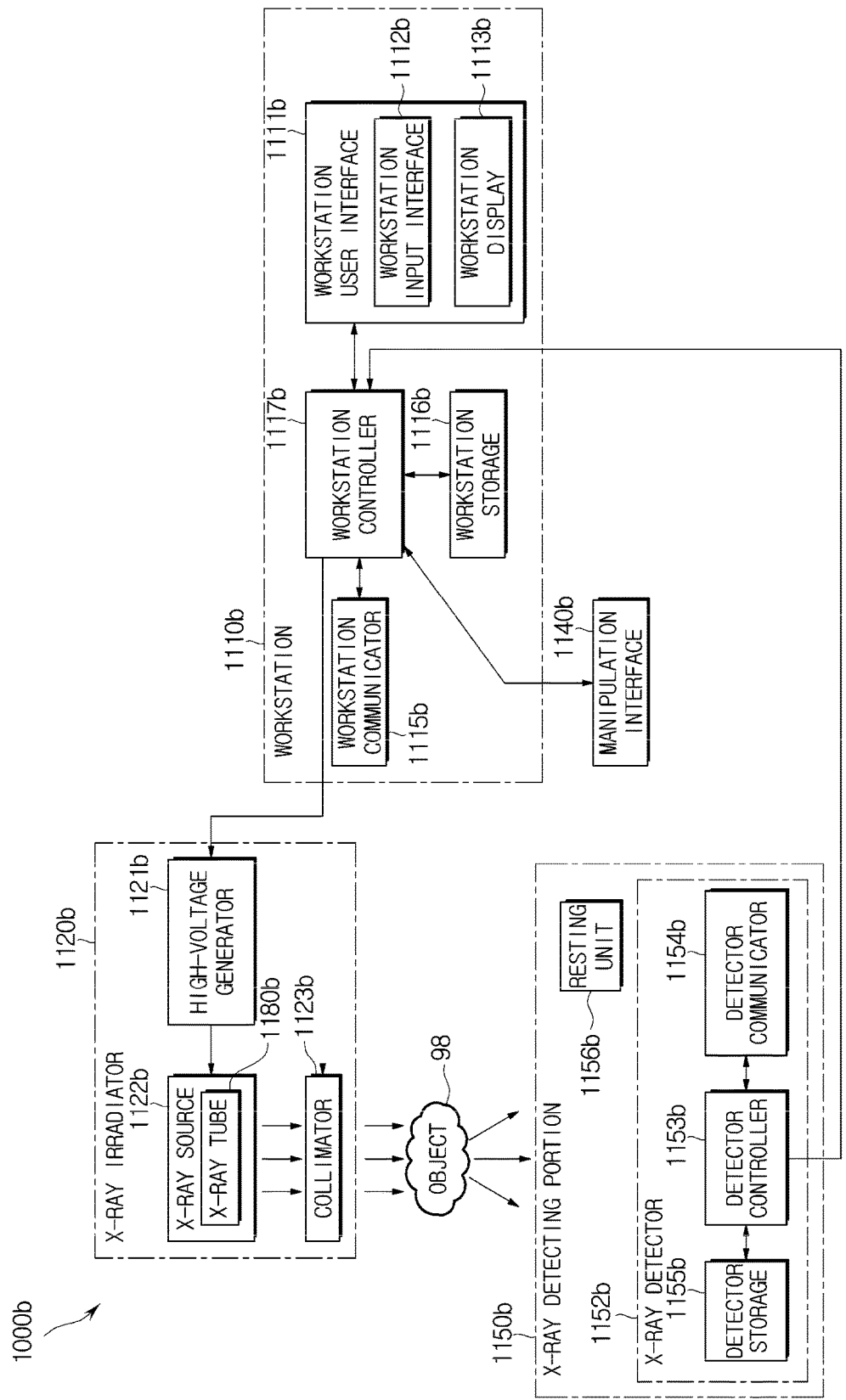
FIG. 8 is a block diagram of an X-ray imaging apparatus that is a controlled medical device, according to another exemplary embodiment.
Figure 9:
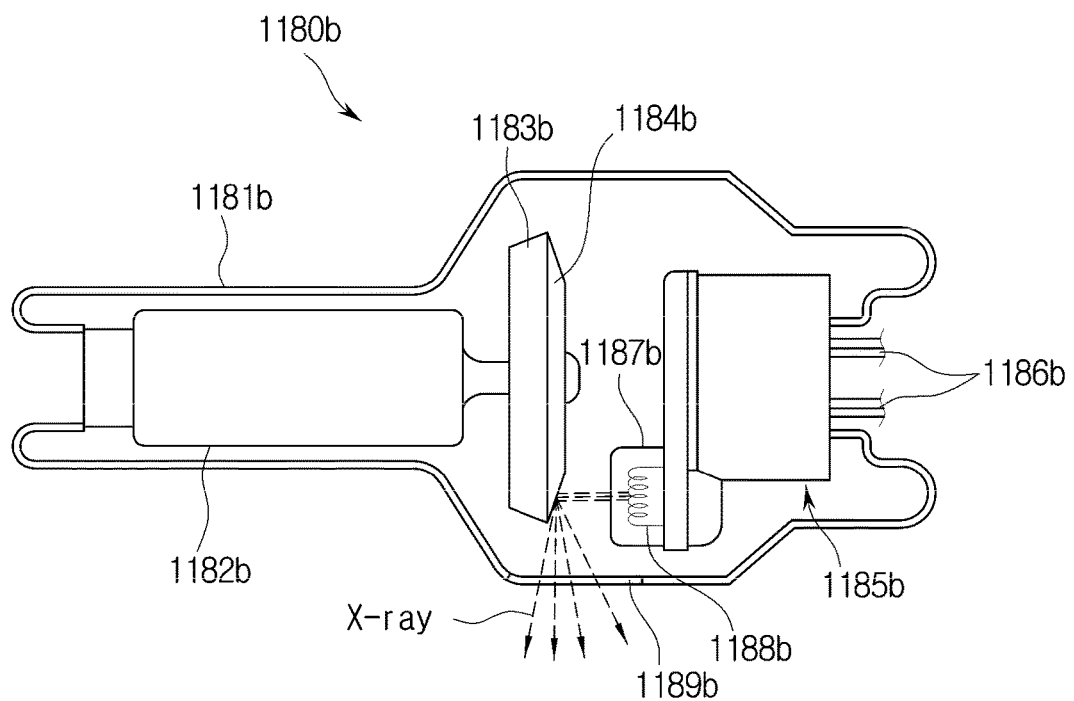
FIG. 9 is a perspective view of an X-ray tube of an X-ray imaging apparatus that is a controlled medical device, according to another exemplary embodiment.
Figure 10:
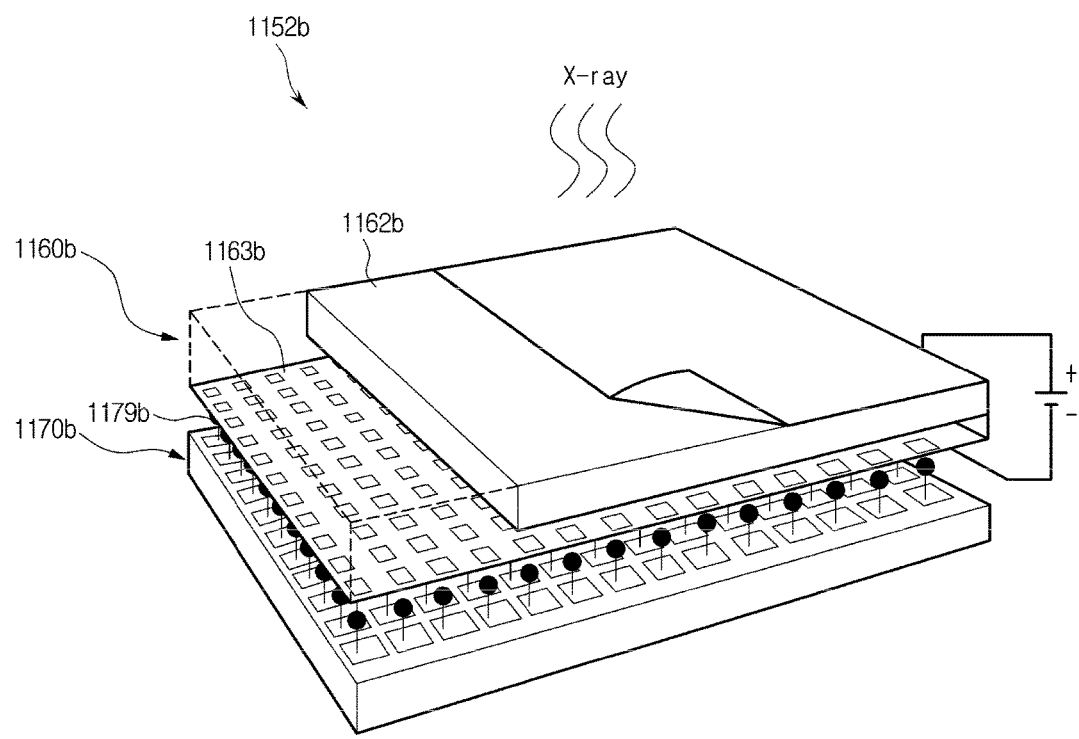
FIG. 10 is a perspective view of an X-ray detector of an X-ray imaging apparatus that is a controlled medical device, according to another exemplary embodiment.
Figure 11:
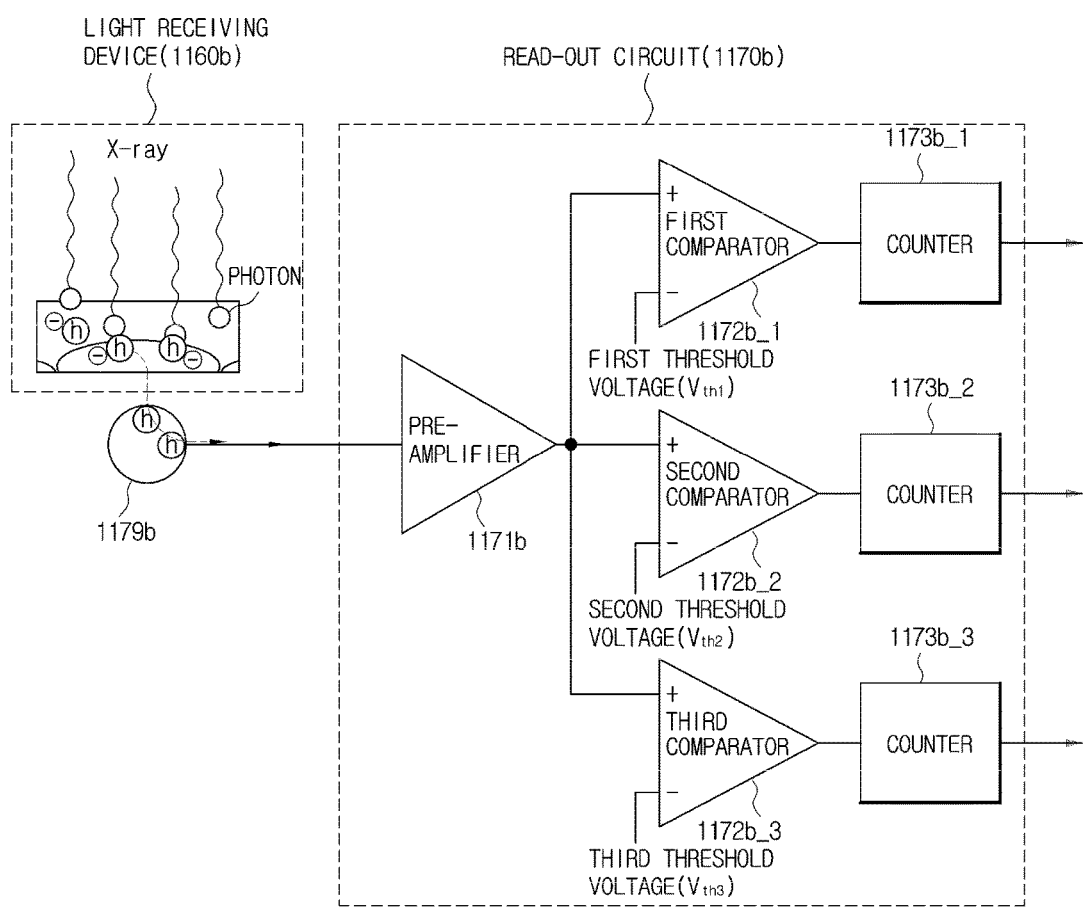
FIG. 11 is a circuit diagram of an X-ray detector of an X-ray imaging apparatus that is a controlled medical device, according to another exemplary embodiment.

FIG. 7 is a perspective view of an X-ray imaging apparatus that is a controlled medical device, according to another exemplary embodiment. FIG. 8 is a block diagram of an X-ray imaging apparatus that is a controlled medical device, according to another exemplary embodiment. FIG. 9 is a perspective view of an X-ray tube of an X-ray imaging apparatus that is a controlled medical device, according to another exemplary embodiment. FIG. 10 is a perspective view of an X-ray detector of an X-ray imaging apparatus that is a controlled medical device, according to another exemplary embodiment. FIG. 11 is a circuit diagram of an X-ray detector of an X-ray imaging apparatus that is a controlled medical device, according to another exemplary embodiment.

Referring to FIGS. 7 and 8, an X-ray imaging apparatus 1000b may include a manipulation interface 1140b that provides an interface for allowing a user to manipulate the X-ray imaging apparatus 1000b and includes a speaker to output sound upon irradiation of X-rays, an X-ray irradiator 1120b to irradiate X-rays to the object 98, an input interface 1130b, an X-ray detecting portion 1150b to detect X-rays transmitted through the object 98, a plurality of motors (also, referred to as a first motor 1211b, a second motor 1212b, and a third motor 1213b) to provide a driving force for moving the X-ray irradiator 1120b, and one or more guide rails 1220b, a movement carriage 1230b, and a post frame 1240b to move the X-ray irradiator 1120b by the driving force of the first, second, and third motors 1211b, 1212b, and 1213b.

The guide rails 1220b may include a first guide rail 1221b, and a second guide rail 1222b disposed at a predetermined angle with respect to the first guide rail 1221b. The first guide rail 1221b may extend to cross at right angles to the second guide rail 1222b.

The first guide rail 1221b may be mounted on the ceiling of an examination room where the X-ray imaging apparatus 1000b is placed.

The second guide rail 1222b may be disposed beneath the first guide rail 1221b, and slide with respect to the first guide rail 1221b. The first guide rail 1221b may include a plurality of rollers that are movable along the first guide rail 1221b. The second guide rail 1222b may connect to the rollers and move along the first guide rail 1221b.

A direction in which the first guide rail 1221b extends is defined as a first direction D1, and a direction in which the second guide rail 1222b extends is defined as a second direction D2. Accordingly, the first direction D1 may be orthogonal to the second direction D2, and the first and second directions D1 and D2 may be parallel to the ceiling of the examination room.

The movement carriage 1230b may be disposed beneath the second guide rail 1222b, and move along the second guide rail 1222b. The movement carriage 1230b may include a plurality of rollers to move along the second guide rail 1222b.

Accordingly, the movement carriage 1230b may be movable in the first direction D1 together with the second guide rail 1222b, and movable in the second direction D2 along the second guide rail 1222b.

The post frame 1240b may be fixed on the movement carriage 1230b and disposed below the movement carriage 1230b. The post frame 1240b may include a plurality of posts 1241b, 1242b, 1243b, 1244b, and 1245b.

The posts 1241b, 1242b, 1243b, 1244b, and 1245b may connect to each other such that they can be folded with each other. The length of the post frame 1240b fixed on the movement carriage 1230b may increase or decrease in the elevation direction of the examination room.

A direction in which the length of the post frame 1240b increases or decreases is defined as a third direction D3. Accordingly, the third direction D3 may be orthogonal to the first direction D1 and the second direction D2.

The X-ray irradiator 1120b may include an X-ray source 1122b to generate X-rays, and a collimator 1123b to adjust an irradiation range of X-rays generated by the X-ray source 1122b. The X-ray source 1122b may include an X-ray tube 1180b.

A high-voltage generator 1121b may be included in the X-ray source 1122b, as described above, however, the high-voltage generator 1121b may be included in another component of the X-ray imaging apparatus 1000b.

The X-ray detecting portion 1150b, which is a digital detector, may detect X-rays transmitted through the object 98, and may be a table type 1138b or a stand type 1137b. The X-ray detecting portion 1150b may include Thin Film Transistors (TFTs) or charge-coupled devices (CCDs).

A revolute joint 1250b may be disposed between the X-ray irradiator 1120b and the post frame 1240b. The revolute joint 1250b may connect the X-ray irradiator 1120b to the post frame 1240b, and support load that is applied to the X-ray irradiator 1120b.

The X-ray irradiator 1120b connected to the revolute joint 1250b may rotate on a plane that is perpendicular to the third direction D3. The rotation direction of the X-ray irradiator 1120b is defined as a fourth direction D4.

The X-ray irradiator 1120b is rotatable on a plane that is perpendicular to the ceiling of the examination room. Accordingly, the X-ray irradiator 1120b may rotate in a fifth direction D5 which is a rotation direction on an axis parallel to the first direction D1 or the second direction D2 with respect to the revolute joint 1250b.

To move the X-ray irradiator 1120b in the first direction D1, the second direction D2, and the third direction D3, the first, second, and third motors 1211b, 1212b, and 1213b may be provided. The first, second, and third motors 1211b, 1212b, and 1213b may be electrically driven, and may include encoders.

The first, second, and third motors 1211b, 1212b, and 1213b may be arranged at appropriate locations in consideration of convenience of design. For example, the first motor 1211b that is used to move the second guide rail 1222b in the first direction D1 may be disposed around the first guide rail 1221b, the second motor 1212b that is used to move the movement carriage 1230b in the second direction D2 may be disposed around the second guide rail 1222b, and the third motor 1213b that is used to increase or decrease the length of the post frame 1240b in the third direction D3 may be disposed in the movement carriage 1230b. As another example, the first, second, and third motors 1211b, 1212b, and 1213b may be connected to a power transfer device to linearly move the X-ray irradiator 1120b in the first to fifth directions D1 to D5. The power transfer device may be a belt and a pulley, a chain and a sprocket, a shaft, and the like.

As still another example, the first, second, and third motors 1211b, 1212b, and 1213b may be disposed between the revolute joint 1250b and the post frame 1240b and between the revolution joint 1250b and the X-ray irradiator 1120b, to rotate the X-ray irradiator 1120b in the fourth and fifth directions D4 and D5.

At a part of the X-ray irradiator 1120b may be provided the manipulation interface 1140b that provides an interface for allowing a user to input various information related to an X-ray examination and to manipulate the individual components of the X-ray imaging apparatus 1000b.

In FIG. 7, a fixed-type X-ray imaging apparatus connected to the ceiling of an examination room is shown, however, the X-ray imaging apparatus 1000b according to an exemplary embodiment may include, as well as the fixed-type X-ray imaging apparatus shown in FIG. 7, various kinds of X-ray apparatuses, such as a C-arm type X-ray apparatus and an angiography X-ray apparatus, which can be considered by one of ordinary skill in the art.

Referring to FIG. 8, the X-ray imaging apparatus 1000b may include the X-ray irradiator 1120b, the X-ray detecting portion 1150b, a workstation 1110b, and the manipulation interface 1140b.

The X-ray irradiator 1120b, which is used to generate X-rays and to irradiate the X-rays to the object 98, may include the high-voltage generator 1121b, the X-ray source 1122b, and the collimator 1123b.

The high-voltage generator 1121b may receive a control signal from the workstation 1110b, and generate a high voltage for generating X-rays.

The high-voltage generator 1121b may receive a preparation signal from the manipulation interface 1140b to start preheating, and when preheating is completed, the high-voltage generator 1121b may output a ready signal to the workstation 1110b. The X-ray detecting portion 1150b may prepare for X-ray detection. If the high-voltage generator 1121b receives a preparation signal from the manipulation interface 1140b, the high-voltage generator 1121b may start preheating, and simultaneously output the preparation signal to the X-ray detecting portion 1150b so that the X-ray detecting portion 1150b can prepare to detect X-rays transmitted through the object 98. If the X-ray detecting portion 1150b receives the preparation signal, the X-ray detecting portion 1150b may prepare to detect X-rays. After the X-ray detecting portion 1150b completes preparation for detecting X-rays, the X-ray detecting portion 1150b may output a detection ready signal to the high-voltage generator 1121b and the workstation 1110b.

If the high-voltage generator 1121b completes preheating, the X-ray detecting portion 1150b completes preparation for X-ray detection, and an irradiation signal is output from the manipulation interface 1140b to the high-voltage generator 1121b, the high-voltage generator 1121b may generate a high voltage and apply the high voltage to the X-ray source 1122b, and the X-ray source 1122b may irradiate X-rays.

The X-ray source 1122b may receive the high voltage generated by the high-voltage generator 1121b, generate X-rays, and irradiate the X-rays. The collimator 1123b may guide an irradiation path of the X-rays irradiated from the X-ray source 1122b.

Referring to FIG. 9, the X-ray source 1122b may include an X-ray tube 1180b which may be embodied as a two-electrode vacuum tube including an anode 1183b and a cathode 1185b. The body of the two-electrode vacuum tube may be a glass tube 1181b made of silica (hard) glass or the like.

The cathode 1185b includes a filament 1188b and a focusing electrode 1187b for focusing electrons, and the focusing electrode 1187b is also called a focusing cup. The inside of the glass tube 1181b is evacuated to a high vacuum state of about 10 mmHg, and the filament 1188b of the cathode 1185b is heated to a high temperature, thereby generating thermoelectrons. The filament 1188b may be a tungsten filament, and the filament 1188*b* may be heated by applying current to electrical leads 1186*b* connected to the filament 1188*b*. However, instead of the filament 1188*b*, a carbon nano-tube capable of being driven with high-speed pulses may be used as the cathode 1185*b*.

The anode 1183*b* may be made of copper, and a target material 1184*b* is applied on the surface of the anode 1183*b* facing the cathode 1185*b*, wherein the target material 1184*b* may be a high-resistance material, e.g., Cr, Fe, Co, Ni, W, or Mo. The higher the melting point of the target material 1184*b*, the smaller the focal spot size.

When a high voltage is applied between the cathode 1185*b* and the anode 1183*b*, thermoelectrons may be accelerated and collide with the target material 1184*b* of the anode 1183*b*, thereby generating X-rays. The X-rays may be irradiated to the outside through a window 1189*b*. The window 1189*b* may be a Beryllium (Be) thin film. A filter may be provided on the front or rear side of the window 1189*b* to filter an energy band of X-rays.

The target material 1184*b* may be rotated by a rotor 1182*b*. When the target material 1184*b* rotates, the heat accumulation rate may increase 10 times or more per unit region and the focal spot size may be reduced, compared to when the target material 1184*b* is fixed.

The voltage that is applied between the cathode 1185*b* and the anode 1183*b* of the X-ray tube 1180*b* is called a tube voltage. The magnitude of a tube voltage may be expressed as a crest value (kVp).

When the tube voltage increases, velocity of thermoelectrons increases accordingly. Then, energy (energy of photons) of X-rays that are generated when the thermoelectrons collide with the target material 1184*b* also increases. And, as the energy of X-rays increases, a larger amount of X-rays comes to be transmitted through the object 98. Accordingly, the X-ray detecting portion 1150*b* also will detect a large amount of X-rays. As a result, an X-ray image having a high Signal-to-Noise Ratio (SNR), that is, an X-ray image having high quality can be obtained.

On the contrary, when the tube voltage decreases, velocity of thermoelectrons decreases accordingly. Then, energy (energy of photons) of X-rays that are generated when the thermoelectrons collide with the target material 1184*b* also decreases. And, as the energy of X-rays decreases, a larger amount of X-rays comes to be absorbed in the object 98. Accordingly, the X-ray detecting portion 1150*b* will detect a small amount of X-rays. As a result, an X-ray image having a low SNR, that is, an X-ray image having low quality will be obtained.

Current flowing through the X-ray tube 1180*b* is called tube current, and can be expressed as an average value (mA). When tube current increases, a dose of X-rays (that is, the number of X-ray photons) increases, and an X-ray image having a high SNR can be obtained. On the contrary, when tube current decrease, a dose of X-rays (that is, the number of X-ray photons) decreases, and an X-ray image having a low SNR may be obtained.

In summary, an energy level of X-rays can be controlled by adjusting a tube voltage. Also, a dose or intensity of X-rays can be controlled by adjusting tube current and an X-ray exposure time. In other words, by controlling a tube voltage or tube current according to the kind or properties of an object, an energy or dose of X-rays to be irradiated can be controlled.

Referring again to FIG. 8, X-rays that are irradiated from the X-ray source 1122*b* have an energy band that is defined by upper and lower limits. The upper limit of the energy band, that is, maximum energy of X-rays to be irradiated may be adjusted by the magnitude of a tube voltage. The lower limit of the energy band, that is, minimum energy of X-rays to be irradiated may be adjusted by a filter included in the X-ray source 1122*b*. By filtering out X-rays having a low energy band using the filter, average energy of X-rays to be irradiated can be increased. Energy of X-rays to be irradiated may be expressed as maximum energy or average energy.

The X-ray source 1122*b* and the collimator 1123*b* may be the same as or different from the X-ray source 1122*b* and the collimator 1123*b* of FIG. 7.

The X-ray detecting portion 1150*b* may sense X-rays passing through the object 98, and convert the X-rays into image signals. The X-ray detecting portion 1150*b* may include a resting unit 1156*b* and an X-ray detector 1152*b*.

The resting unit 1156*b* may be a support to provide space on which the X-ray detector 1152*b* is rested. The resting unit 1156*b* may accommodate the X-ray detector 1152*b* therein, and fix the X-ray detector 1152*b* to enable the X-ray detector 1152*b* to photograph X-ray images.

The X-ray detector 1152*b* may detect X-rays irradiated by the X-ray source 1122*b* and then transmitted through the object 98. The X-rays may be detected by the sensing panel installed in the X-ray detector 1152*b*. The sensing panel may convert the detected X-rays into electrical signals, and acquire an image about the object.

The sensing panel can be classified according to its material configuration, a method of converting detected X-rays into electrical signals, and a method of acquiring image signals.

The sensing panel is classified into a mono type device or a hybrid type device according to its material configuration.

If the sensing panel is a mono type device, a part of detecting X-rays and generating electrical signals, and a part of reading and processing the electrical signals may be semiconductors made of the same material, or may be manufactured by one process. In this case, the sensing panel may be a CCD or a Complementary Metal Oxide Semiconductor (CMOS) which is a light receiving device 1160*b* (see FIG. 10).

If the sensing panel is a hybrid type device, a part of detecting X-rays and generating electrical signals, and a part of reading and processing the electrical signals may be made of different materials, or may be manufactured by different processes. For example, there are cases of detecting X-rays using a light receiving device 1160*b*, such as a photodiode, a CCD, or CdZnTe, and reading and processing electrical signals using a CMOS Read Out Integrated Circuit (CMOS ROIC), of detecting X-rays using a strip detector, and reading and processing electrical signals using a CMOS ROIC, and of using an a-Si or a-Se flat panel system.

The sensing panel may use a direct conversion mode and an indirect conversion mode according to a method of converting X-rays into electrical signals.

In the direct conversion mode, if X-rays are irradiated, electron-hole pairs are temporarily generated in the light receiving device 1160*b*, electrons move to the anode 1183*b*, and holes move to the cathode 1185*b* by an electric field applied to both terminals of the light receiving device 1160*b*. The sensing panel converts the movements of the electrons and holes into electrical signals. The light receiving device 1160*b* may be made of a-Se, CdZnTe, HgI2, or PbI2.

In the indirect conversion mode, if X-rays irradiated from the X-ray source 1122*b* react with a scintillator to emit photons having a wavelength of a visible light region, the light receiving device 1160*b* detects the photons, and converts the photons into electrical signals. The light receiving device 1160b may be made of a-Si, and the scintillator may be a GADOX scintillator of a thin film type, or a CSI (TI) of a micro pillar type or a needle type.

The sensing panel may use a Charge Integration Mode (CIM) of storing charges for a predetermined time period and then acquiring a signal from the stored charges, or a Photon Counting Mode (PCM) of counting the number of photons having energy higher than threshold energy whenever a signal is generated by single X-ray photons, according to a method of acquiring image signals.

The material configuration of the sensing panel and the signal conversion method of the sensing panel are not limited, however, for convenience of description, in an exemplary embodiment, the sensing panel uses the direct conversion mode of acquiring electrical signals directly from X-rays and the PCM, and the sensing panel is a hybrid type in which a sensor chip for detecting X-rays is integrated with a read-out circuit 1170b (see FIG. 10).

The sensing panel of the X-ray detector 1152b may have a 2D array structure including a plurality of pixels, as illustrated in FIG. 10.

Referring to FIG. 10, the sensing panel of the X-ray detector 1152b may include the light receiving device 1160b to detect X-rays and convert the X-rays into electrical signals, and the read-out circuit 1170b to read out the electrical signals.

The light receiving device 1160b may be made of a single crystal semiconductor material to ensure high resolution, high response speed, and a high dynamic area even under conditions of low energy and a small dose of X-rays. The single crystal semiconductor material may be Ge, CdTe, CdZnTe, or GaAs.

The light receiving device 1160b may be a PIN photodiode. The PIN photodiode may be fabricated by bonding a p-type semiconductor substrate 1163b as a 2D pixel array on the lower surface of a n-type semiconductor substrate 1162b having high resistance.

The read-out circuit 1170b, which is fabricated according to a Complementary Metal Oxide Semiconductor (CMOS) process, may form a 2D array structure, and may be coupled with the p-type substrate of the light receiving device 1160b in units of pixels. The read-out circuit 1170b and the light receiving device 1160b may be coupled by a Flip-Chip Bonding (FCB) method. The read-out circuit 1170b and the light receiving device 1160b may be coupled by forming bumps 1179b with PbSn, In, or the like, reflowing, applying heat, and then compressing.

Referring to FIG. 11, if photons of X-rays are incident to the light receiving device 1160B, electrons existing in a valance band may receive the energy of the photons to be excited to a conduction band over an energy gap of a band gap. Thereby, electron-hole pairs may be generated in a depletion region where neither electrons nor holes exist.

If a reverse bias is applied after metal electrodes are respectively formed on the p-type layer and the n-type substrate of the light receiving device 1160b, electrons in the electron-hole pairs generated in the depletion region may move to the n-type region, and holes in the electron-hole pairs may move to the p-type region. The holes moved to the p-type region may be input to the read-out circuit 1170b through the bumps 1179b.

Charges input to the read-out circuit 1170b may be transferred to a pre-amplifier 1171b, and the pre-amplifier 1171b may output a voltage signal corresponding to the charges.

The voltage signal output from the pre-amplifier 1171b may be transferred to a comparator 1172b. The comparator 1172b may compare the voltage signal to a predetermined threshold voltage that can be controlled by an external device, to output a pulse signal of "1" or "0" as the result of the comparison. If a voltage of the voltage signal is greater than the predetermined threshold voltage, the comparator 1172b may output a signal of "1," and if the voltage of the voltage signal is smaller than the predetermined threshold voltage, the comparator 1172b may output a signal of "0." The counter 1173b may count the number of times a signal of "1" has been generated, and output the count value as digital data.

To enhance the contrast of internal tissues of the object 98, a plurality of X-ray images of a plurality of different energy bands may be acquired to produce a multi-energy X-ray image. To acquire a plurality of X-ray images of a plurality of different energy bands, X-rays having different energy bands are irradiated several times. However, because the X-ray detecting portion 1150b of the X-ray imaging apparatus 1000b is implemented as a PCD, the X-ray generator may irradiate X-rays one time, and the X-ray detecting portion 1150b may divide detected X-rays according to a plurality of energy bands.

To do this, as illustrated in FIG. 11, a plurality of comparators (that is, first, second, and third comparators 1172b_1, 1172b_2, and 1172b_3) and a plurality of counters (that is, first, second, and third counters 1173b_1, 1173b_2, and 1173b_3) may be provided to count the number of photons for each energy band. In FIG. 11, an example in which three comparators are provided is shown, however, a different number of comparators may be provided according to the number of energy bands to be divided.

Referring to FIG. 11, if an electron or a hole generated by a single photon is input to the pre-amplifier 1171b and then output as a voltage signal, the voltage signal is input to the three comparators 1172b_1, 1172b_2, and 1172b_3. Then, first, second, and third threshold voltages $V_{th1}$, $V_{th2}$, and $V_{th3}$ are applied to the respective comparators 1172b_1, 1172b_2, and 1172b_3. The first comparator 1172b_1 compares the voltage signal to the first threshold voltage $V_{th1}$, and the first counter 1173b_1 counts the number of photons that have generated a higher voltage than the first threshold voltage $V_{th1}$. In the same way, the second counter 1173b_2 counts the number of photons that have generated a higher voltage than the second threshold voltage $V_{th2}$, and the third counter 1173b_3 counts the number of photons that have generated a higher voltage than the third threshold voltage $V_{th3}$.

Referring again to FIG. 8, the X-ray detector 1152b may include a detector storage 1155b, a detector communicator 1154b, and a detector controller 1153b.

The X-ray storage 1155b may store detector identification information that specifies a kind of the corresponding X-ray detector 1152b.

The detector identification information is information to identify the X-ray detector 1152b among a plurality of X-ray detectors. The detector identification information may include a detector model, a serial number, and a detector Internet Protocol (IP). The detector model may be a model name of a detector manufactured by a manufacturing company. The serial number may be information to identify each of a plurality of detectors belonging to the same detector model, and may be a manufactured date or a serial number of the corresponding detector. The detector IP may be information to detect each of a plurality of detectors belonging to the same detector model and having the same serial number, and may be a protocol set to communicate with the workstation 1110b.

The detector communicator 1154*b* may transmit and receive information for identifying and setting the corresponding X-ray detector 1152*b* to and from the workstation 1110. The detector communicator 1154*b* may transmit the detector identification information stored in the detector storage 1155*b* to the workstation 1110*b*, and receive setting information of the corresponding X-ray detector 1152*b* from the workstation 1110*b*. The detector communicator 1154*b* may transfer electrical signals received and converted by the X-ray detector 1152*b* to the workstation 111*b*. The detector communicator 1154*b* may transfer a protocol set to communicate with a network to the workstation 1110*b*, and enable the workstation 1110*b* to recognize an examination room where the corresponding X-ray detector 1152B is placed. The detector communicator 1154*b* may connect to the network by a wire or wirelessly to communicate with an external server, another user interface, another medical device, or a network hub. The detector communicator 1154*b* may perform data communication according to a predetermined communication standard.

The detector communicator 1154*b* may transmit and receive data related to remote control, and information about operations of another medical device, through the network. The detector communicator 1154*b* may receive information about corrected errors of detector models from a server, and use the received information for operations of the X-ray imaging apparatus 1000*b*.

The detector communicator 1154*b* may connect to the network by a wire or wirelessly, and transmit and receive data to and from a server, another user interface, another medical device, or a network hub.

The detector controller 1153*b* may control operations of the X-ray detector 1152*b*. The detector controller 1153*b* may receive the detector identification information from the detector storage 1155*b* to transfer the detector identification information to the workstation 1110*b*, and receive setting information from the workstation 1110*b* to set scanning conditions of the X-ray detector 1152*b* and to set information according to the properties of an installation unit in which the corresponding X-ray detector 1152*b* is installed. The detector controller 1153*b* may control the detector communicator 1154*b* to transfer location information of the corresponding X-ray detector 1152*b* sensed by a detector sensor to the workstation 1110*b*, and to transfer a protocol of the corresponding X-ray detector 1152*b* to the workstation 1110*b*. The detector controller 1153*b* may convert received X-rays into electrical signals to generate image signals.

The workstation 1110*b* may connect to a plurality of X-ray detectors 1152*b* to control the X-ray detectors 1152*b*, and receive image signals to display images. The workstation 1110*b* may include a workstation storage 1116*b*, a workstation communicator 1115*b*, a workstation user interface 1111*b*, and a workstation controller 1117*b*.

The workstation storage 1116*b* may store various data for controlling and operating the workstation 1110*b*, and transfer the stored data to the workstation controller 1117*b*.

The workstation communicator 1115*b* may receive detector identification information from the X-ray detector 1152*b*, and transfer setting information of the X-ray detector 1152*b*, control signals for the X-ray detector 1152*b*, etc., to the X-ray detector 1152*b*.

The workstation user interface 1111*b* may include a workstation input interface 1112*b* and a workstation display 1113*b*. The workstation display 1113*b* may display X-ray images and a graphic user interface for settings of the X-ray detector 1152*b*, and the workstation input interface 1112*b* may receive control commands for acquiring X-ray images, commands for setting the X-ray detector 1152*b*, etc.

The workstation controller 1117*b* may control operations of the workstation 1110*b*. The workstation controller 1117*b* may receive a plurality of detector identification information, and compare the detector identification information to a list of detectors to search for information that is identical to the detector identification information from the list of detectors. The workstation controller 1117*b* may search for X-ray detectors 1152*b* that can be connected to the workstation 1110*b*, and arrange and display information about the X-ray detectors 1152*b* as a GUI. The workstation controller 1117*b* may select an X-ray detector 1152*b* among the X-ray detectors 1152*b* to which the workstation 1110*b* can connect, store setting information of the X-ray detector 1152*b*, and transfer the stored setting information to the X-ray detector 1152*b*. The workstation controller 1117*b* may transfer a control signal to the X-ray irradiator 1120*b* to enable the X-ray irradiator 1120*b* to generate X-rays and irradiate the X-rays to the object 98. The workstation controller 1117*b* may receive image signals from the X-ray detecting portion 1150*b*.

The manipulation interface 1140*b* may receive a user's command for enabling the X-ray imaging apparatus 1000*b* to acquire an X-ray image of the object 98.

Figure 12:
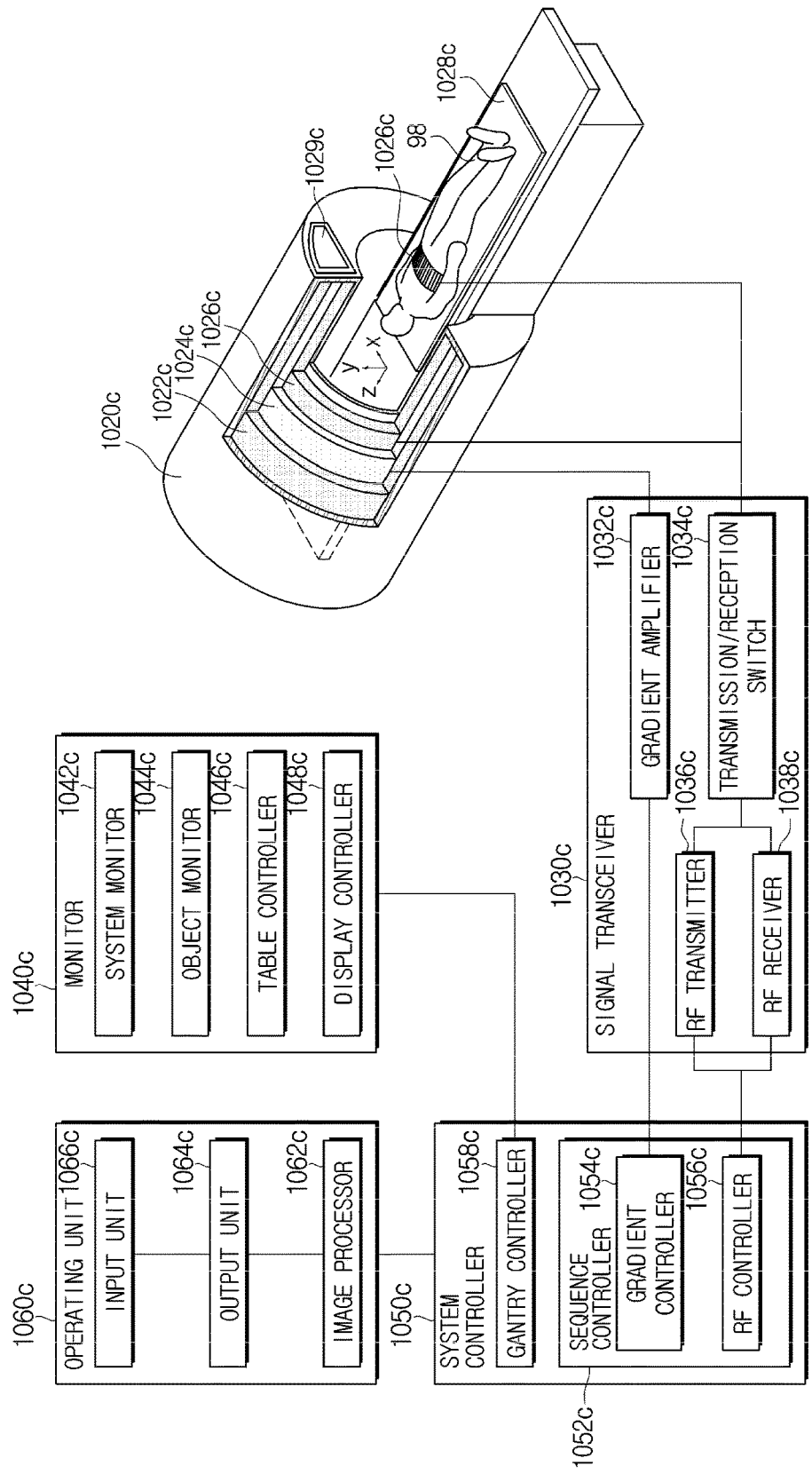
FIG. 12 is a perspective view of an MRI apparatus that is a controlled medical device, according to another exemplary embodiment.

FIG. 12 is a perspective view of a MRI apparatus that is a controlled medical device, according to another exemplary embodiment.

Referring to FIG. 12, a MRI apparatus may include a gantry 1020*c*, a signal transceiver 1030*c*, a monitor 1040*c*, a system controller 1050*c*, and an operating controller 1060*c*.

The gantry 1020*c* may prevent electronic waves generated by a main magnet 1022*c*, a gradient coil 1024*c*, an RF coil 1026*c*, etc., from leaking out. Inside the bore of the gantry 1020*c*, a static magnetic field and a gradient magnetic field may be formed, and RF signals may be irradiated toward the object 98.

The main magnet 1022*c*, the gradient coil 1024*c*, and the RF coil 1026*c* may be disposed in a predetermined direction in which the gantry 1020*c* extends. The predetermined direction may be a coaxial direction of the cylindrical structure of the gantry 1020*c*. The object 98 may be placed on a table 1028*c* that can be inserted into the cylindrical structure along the horizontal axis of the cylindrical structure.

The main magnet 1022*c* may form a magnetostatic field or a static magnetic field to align the magnetic dipole moment of atomic nuclei included in the object 98 in a direction. As a magnetic field formed by the main magnet 1022*c* is stronger or more uniform, the more accurate Magnetic Resonance (MR) image for the object 98 can be acquired.

The gradient coil 1024*c* may include X, Y, and Z coils to generate gradient magnetic fields in X-, Y-, and Z-axis directions that are at right angles with respect to each other. The gradient coil 1024*c* may induce different resonance frequencies according to different parts of the object 98 to provide location information for each part of the object 98.

The RF coil 1026*c* may irradiate RF signals to a patient, and receive MR signals emitted from the patient. The RF coil 1026*c* may transmit RF signals of the same frequency as that of precession toward atomic nuclei that performs precession, to a patient, then stop transmitting the RF signals, and then receive MR signals emitted from the patient.

For example, to change atomic nucleus from a low energy state to a high energy state, the RF coil 1026c may generate electronic wave signals (for example, RF signals) of a radio frequency corresponding to the kind of the atomic nucleus, and apply the electronic wave signals to the object 98. If the electronic wave signals generated by the RF coil 1026c are applied to the atomic nucleus, the atomic nucleus may change from a low energy state to a high energy state. Thereafter, if the electronic wave signals generated by the RF coil 1026c disappear, the atomic nucleus to which the electronic wave signals have been applied may return to the low energy state from the high energy state to emit electronic waves having the Larmor frequency. In other words, if the electronic wave signals are no longer applied to the atomic nucleus, a change in energy level from high energy to low energy occurs so that electronic waves having the Larmor frequency may be emitted. The RF coil 1026c may receive electronic wave signals emitted from atomic nuclei in the object 98.

The RF coil 1026c may be embodied as an RF transmission/reception coil having both a function of generating electronic waves having an RF frequency corresponding to the kind of atomic nuclei and a function of receiving electronic waves emitted from atomic nuclei. The RF coil 1026c may be embodied as a transmission RF coil having a function of generating electronic waves having an RF frequency corresponding to the kind of atomic nuclei, and a reception RF coil having a function of receiving electronic waves emitted from atomic nuclei.

The RF coil 1026c may be fixed at the gantry 1020c, or detachably attached on the gantry 1020c. The RF coil 1026c which can be detachably attached on the gantry 1020c may include a plurality of RF coils for various parts of the object 98, including a head RF coil, a chest RF coil, a leg RF coil, a neck RF coil, a shoulder RF coil, a wrist RF coil, and an ankle RF coil.

The RF coil 1026c may communicate with an external device by a wire or wirelessly including optical fibers.

The RF coil 1026c may be a dual tune coil or a multi tune coil that can transmit and receive two or more resonance frequencies to receive MR signals for two or more atomic nuclei.

The RF coil 1026c may be a birdcage coil, a surface coil, or a Traverse Electro Magnetic (TEM) coil, according to the structure of the coil.

The RF coil 1026c may be a transmission-dedicated coil, a reception-dedicated coil, or a transceiver coil, according to a method of transmitting and receiving RF signals.

The RF coil 1026c may be a RF coil of various channels, such as 16 channels, 32 channels, 72 channels, and 144 channels.

The gantry 1020c may further include a display 1029c disposed outside, and a display 1029c disposed inside. Through the displays 1029c located outside and inside the gantry 1020c, predetermined information may be provided to a user or the object 98.

The signal transceiver 1030c may control a gradient magnetic field formed inside the gantry 1020c, that is, in the bore, according to a predetermined MR sequence, and control transmission/reception of RF signals and MR signals.

The signal transceiver 1030c may include a gradient amplifier 1032c, a transmission/reception switch 1034c, an RF transmitter 1036c, and an RF receiver 1038c.

The magnetic amplifier 1032c may drive the gradient coil 1024c included in the gantry 1020c, and supply pulse signals for forming a gradient field to the gradient coil 1024c under the control of the gradient controller 1054c. By controlling pulse signals that are supplied from the gradient amplifier 1032c to the gradient coil 1024c, a gradient field may be formed in X-, Y-, and Z-axis directions.

The RF transmitter 1036c and the RF receiver 1038c may drive the RF coil 1026c. The RF transmitter 1036c may supply RF pulses of the Larmor frequency to the RF coil 1026c, and the RF receiver 1038c may receive MR signals received by the RF coil 1026c.

The transmission/reception switch 1034c may adjust a direction in which RF signals and MR signals are transmitted or received. For example, in a transmission mode, the transmission/reception switch 1034c may cause RF signals to be irradiated to the object 98 through the RF coil 1026c, and in a reception mode, the transmission/reception switch 1034c may cause MR signals to be received from the object 98 through the RF coil 1026c. The transmission/reception switch 1034c may be controlled according to a control signal from the RF controller 1056c.

The monitor 1040c may monitor or control the gantry 1020c or components included in the gantry 1020c. The monitor 1040c may include a system monitor 1042c, an object monitor 1044c, a table controller 1046c, and a display controller 1048c

The system monitor 1042c may monitor and control a static magnetic field, a gradient magnetic field, RF signals, the state of the RF coil 1026c, the state of the table 1028c, the state of a device to measure body information of the object 98, a power supply state, the state of a heat exchanger, the state of a compressor, etc.

The object monitor 1044c may monitor the object 98. The object monitor 1044c may include a camera to observe a movement or location of the object 98, a respirometer for measuring the breath of the object 98, an electrocardiogram (ECG) measuring instrument for measuring the ECG of the object 98, and a thermometer for measuring the temperature of the object 98.

The table controller 1046c may control movement of the table 1028c on which the object 98 is placed. The table controller 1046c may control movement of the table 1028c according to a sequence control by a sequence controller 1052c. For example, upon moving imaging of the object 98, the table controller 1046c may move the table 1028c successively or intermittently according to a sequence control by the sequence controller 1052c, and accordingly, the object 98 may be photographed with Field of View (FOC) that is greater than that of the gantry 1020c.

The display controller 1048c may control the displays 1029c disposed outside and inside the gantry 1020c. The display controller 1048c may turn on/off the displays 1029c disposed outside or inside the gantry 1020c, or control screens that are to be displayed on the displays 1029c. Also, if a speaker is provided inside or outside the gantry 1020c, the display controller 1048c may turn on/off the speaker or adjust sound that is to be output through the speaker.

The system controller 1050c may include the sequence controller 1052c to control a sequence of signals formed inside the gantry 1020c, and a gantry controller 1058c to control the gantry 1020c and components included in the gantry 1020c.

The sequence controller 1052c may include a gradient controller 1054c to control the gradient amplifier 1032c, and a RF controller 1056c to control the RF transmitter 1036c, the RF receiver 1038c, and the transmission/reception switch 1034c. The sequence controller 1052c may control the gradient amplifier 1032c, the RF transmitter 1036c, the RF receiver 1038c, and the transceiver switch 1034c according to a pulse sequence received from the operating controller 1060c. Here, the pulse sequence may include all information to be used to control the gradient amplifier 1032c, the RF transmitter 1036c, the RF receiver 1038c, and the transmission/reception switch 1034c. For example, the pulse sequence may include information about the intensity of a pulse signal that is applied to the gradient coil 1024c, an application time period of the pulse signal, an application timing of the pulse signal, etc.

The operating controller 1060c may control operations of the MRI apparatus, and transmit pulse sequence information to the system controller 1050c.

The operating controller 1060c may include an image processor 1062c to process MR signals received from the RF receiver 1038c, an output interface 1064c, and an input interface 1066c.

The image processor 1062c may process MR signals received from the RF receiver 1038c, and generate MR image data for the object 98.

The image processor 1062c may perform various signal processing, such as amplification, frequency conversion, phase detection, low-frequency amplification, and filtering, on MR signals received from the RF receiver 1038c.

The image processor 1062c may locate digital data in k-th space (for example, also referred to as Fourier space or frequency space) of a memory, and perform 2D/3D Fourier transform on the digital data to reconfigure it as image data.

The image processor 1062c may perform synthesizing and operation of difference on the image data. The synthesizing may include addition processing or Maximum Intensity Projection (MIP) processing on pixels. The image processor 1062c may store, as well as reconfigured image data, image data subject to synthesizing or operation of difference, in a memory or an external server.

Also, various signal processing applied to MR signals by the image processor 1062c may be performed in parallel. For example, by applying signal processing in parallel to a plurality of MR signals that are received by a multi-channel RF coil 1026c, the plurality of MR signals may be reconfigured as image data.

The output interface 1064c may output image data or reconfigured image data created by the image processor 1062c to a user. The output interface 1064c may output information, such as User Interface (UI), user information, object information, etc., for manipulating the MRI apparatus. The output interface 1064c may be a speaker, a printer, a CRT display, a LCD, a PDP display, an OLED display, a Field Emission Display (FED) display, a LED display, a Variable Frequency Drive (VFD) display, a DLP display, a PFD display, a 3D display, or a transparent display. However, the output interface 1064c is not limited to these, and may be any other output interface that can be considered by one of ordinary skill in the art.

A user may use the input interface 1066c to input information about the object 98, parameter information, scan conditions, a pulse sequence, or information about image synthesizing or operation of difference. The input interface 1066c may include a keyboard, a mouse, a trackball, a voice recognizer, a gesture recognizer, a touch screen, etc., and may also include various input devices that can be considered by one of ordinary skill in the art.

In FIG. 12, the signal transceiver 1030c, the monitor 1040c, the system controller 1050c, and the operating controller 1060c are shown as separate units, however, the functions that are performed by signal transceiver 1030c, the monitor 1040c, the system controller 1050c, and the operating controller 1060c may be performed by another device. For example, the image processor 1062c may convert MR signals received by the RF receiver 1038c into digital signals, however, conversion of MR signals into digital signals may be performed by the RF receiver 1038c or the RF coil 1026c.

The gantry 1020c, the RF coil 1026c, the signal transceiver 1030c, the monitor 1040c, the system controller 1050c, and the operating controller 1060c may be connected to each other by a wire or wirelessly. If the gantry 1020c, the RF coil 1026c, the signal transceiver 1030c, the monitor 1040c, the system controller 1050c, and the operating controller 1060c are connected to each other wirelessly, a unit for synchronizing clocks between the gantry 1020c, the RF coil 1026c, the signal transceiver 1030c, the monitor 1040c, the system controller 1050c, and the operating controller 1060c may be further provided. Communication between the gantry 1020c, the RF coil 1026c, the signal transceiver 1030c, the monitor 1040c, the system controller 1050c, and the operating controller 1060c may be performed using a high speed digital interface (for example, low voltage differential signaling (LVDS)), asynchronous serial communication (for example, a universal asynchronous receiver transmitter (UART)), a low latency network protocol (for example, error synchronous serial communication or a controller area network (CAN)), optical communication, or any of other various communication methods that are well known to one of ordinary skill in the art.

Figure 13:
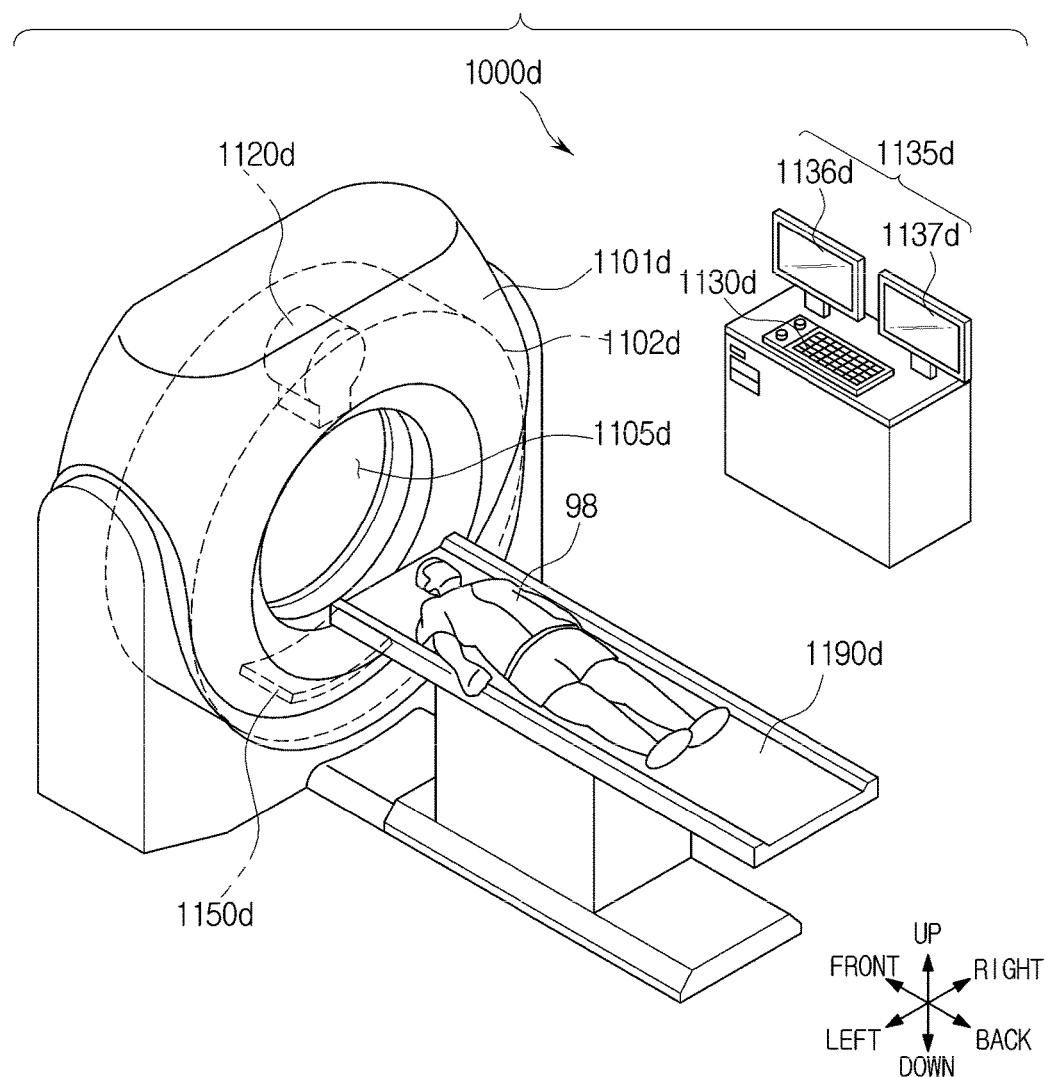
FIG. 13 is a perspective view of a CT apparatus that is a controlled medical device, according to another exemplary embodiment.
Figure 14:
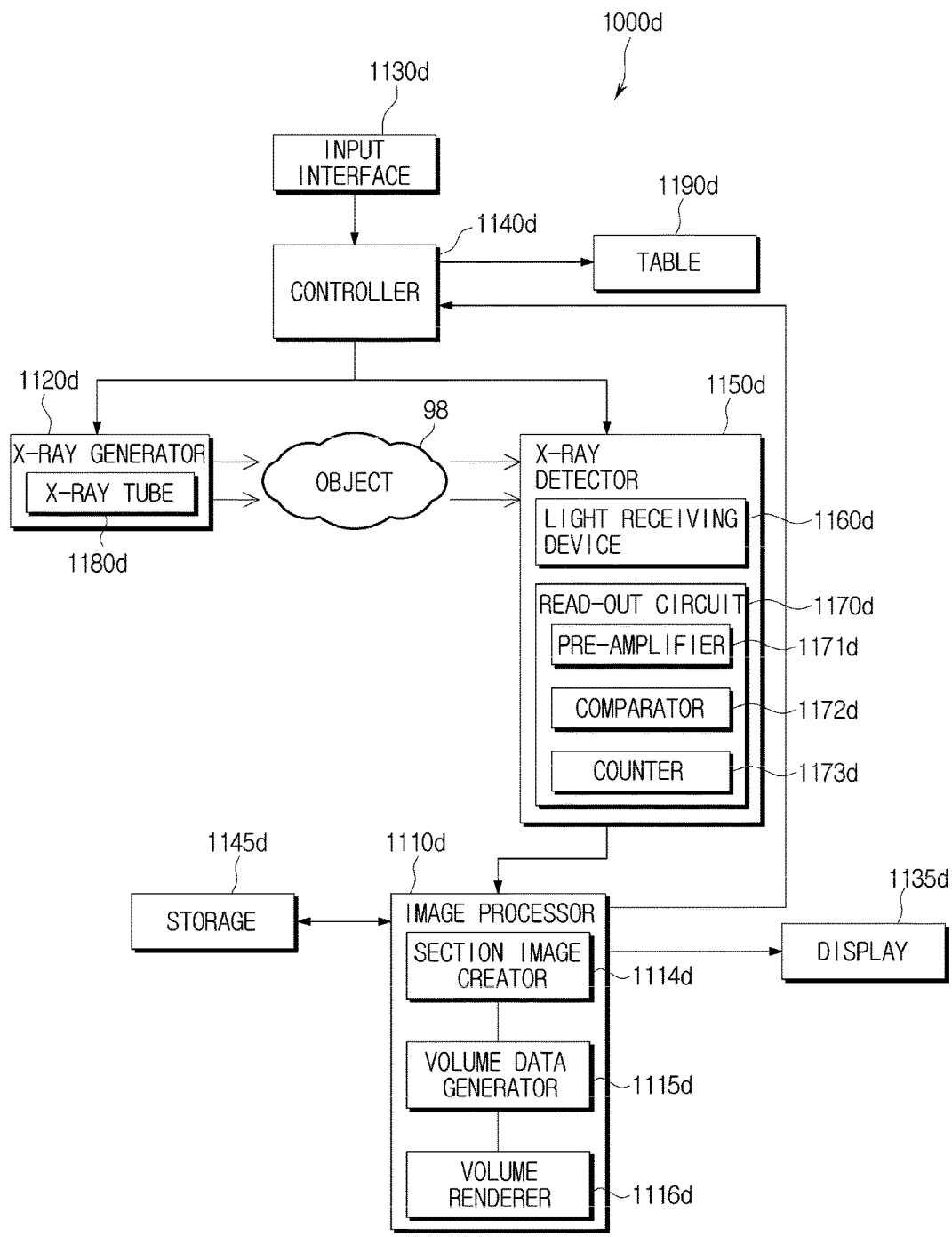
FIG. 14 is a block diagram of a CT apparatus that is a controlled medical device, according to another exemplary embodiment.

FIG. 13 is a perspective view of a CT apparatus that is a controlled medical device, according to another exemplary embodiment. FIG. 14 is a block diagram of a CT apparatus that is a controlled medical device, according to another exemplary embodiment.

Referring to FIG. 13, a CT apparatus 1000d may include a housing 1101d, a table 1190d, an input interface 1130d, and a display 1135d.

A gantry 1102d may be installed in the housing 1101d. In the gantry 1102d, an X-ray generator 1120d and an X-ray detector 1150d may be disposed to be opposite to each other. The gantry 1102d may rotate at an angle ranging from 180° to 360° around a bore 1105d. When the gantry 1102d rotates, the X-ray generator 1120d and the X-ray detector 1150d may rotate accordingly.

A depth camera may be provided near the X-ray generator 1120d. The depth camera may be installed in the gantry 1102d together with the X-ray generator 1120d. As another example, the depth camera may be disposed on the outer surface of the gantry 1102d at a location corresponding to the X-ray generator 1120d. As such, because the depth camera is disposed in the gantry 1102d or on the outer surface of the gantry 1102d, the depth camera may rotate when the gantry 1102d rotates.

The table 1190d may transport the object 98 to be scanned into the bore 1105d. The table 1190d may move in front-rear, up-down, and left-right directions while maintaining horizontality with respect to the ground.

The input interface 1130d may receive instructions or commands for controlling operations of the CT apparatus 1000d. To receive instructions or commands for controlling operations of the CT apparatus 1000d, the input interface 1130d may include at least one of a keyboard and a mouse.

The display 1135d may display an X-ray image of the object 98. The X-ray image may be any one of a section image, a 3D image, and a 3D stereo image of the object 98.

The 3D image of the object 98 may be acquired by performing volume rendering on 3D volume data created based on a plurality of section images with respect to a predetermined viewpoint. That is, a 3D image is a 2D projected image acquired by projecting volume data to a 2D plane with respect to a predetermined viewpoint. The 3D stereo image of the object 98 may be acquired by performing volume rendering on volume data with respect to left and right viewpoints corresponding to a human's left and right eyes to acquire a left image and a right image, and synthesizing the left image with the right image.

The display 1135d may include at least one display. FIG. 13 shows a case in which the display 1135d includes a first display 1136d and a second display 1137d. In this case, the first display 1136d and the second display 1137d may display different kinds of images. For example, the first display 1136d may display a section image, and the second display 1137d may display a 3D image or a 3D stereo image. Alternatively, the first and second displays 1136d and 1137d may display the same kind of images.

Referring to FIG. 14, the CT apparatus 1000d may include the input interface 1130d, a controller 1140d, the X-ray generator 1120d, the X-ray detector 1150d, an image processor 1110d, the display 1135d, a storage 1145d, and the table 1190d.

The input interface 1130d may receive instructions or commands for controlling operations of the CT apparatus 1000d, as described above.

The controller 1140d may calculate a movement direction and a movement distance of the table 1190d based on location information of the object 98 received from a detector of the image processor 1110d, and generate a control signal for moving the table 1190d according to the result of the calculation. The control signal may be provided to a driving unit provided in the table 1190d to move the table 1190d.

The X-ray generator 1120d may generate X-rays, and irradiate the X-rays to the object 98. The X-ray generator 1120d may include an X-ray tube 1180d to generate X-rays. The X-ray detector 1150d may detect X-rays transmitted through the object 98, convert the X-rays into image signals or electrical signals. The X-ray detector 1150d may detect X-rays transmitted through the object 98, and convert the X-rays into image signals and electrical signals. The X-ray detector 1150d may include a light receiving device 1160d and a read-out circuit 1170d. The read-out circuit 1170d may include a pre-amplifier 1171d, a comparator 1172d, and a counter 1173d.

The X-ray generator 1120d and the X-ray detector 1150d of the CT apparatus 1000d may be the same as or different from the X-ray generator 1120b and the X-ray detecting portion 1150b of the X-ray imaging apparatus 1000b.

The image processor 1110d may include a section image creator 1114d, a volume data generator 1115d, and a volume renderer 1116d.

The section image creator 1114d may create a section image based on electrical signals output from the individual pixels of the X-ray detector 1150d. The section image may be an image showing a section of the object 98. As the gantry 1102d rotates, the X-ray generator 1120d and the X-ray detector 1150d may rotate at a predetermined angle around the object 98, so that projection data about the object 98 may be acquired at different positions. The section image creator 1114d may reconstruct the projection data acquired at different positions to create a section image of the object 98.

Reconstructing projection data refers to reconstructing an object represented in a two dimension in projection data to a 3D image that looks similar to a real object. A method of reconstructing projection data includes an iterative method, a non-iterative method, a Direct Fourier (DF) method, and a back projection method.

The iterative method is a method of continuously correcting projection data until data representing a structure similar to the original structure of an object is obtained. The non-iterative method is a method of applying an inverse-transform function of a transform function used to model a 3D object to a 2D image to a plurality of pieces of projection data to reconstruct 2D images to a 3D image. An example of the non-iterative method is Filtered Back-Projection (FBP). The FBP is a method of filtering projection data to cancel blurs formed around the center portion of a projected image and then back-projecting. The DF method is a method of transforming projection data from a spatial domain to a frequency domain. The back projection method is a method of reconstructing projection data acquired at a plurality of viewpoints on a screen.

The volume data generator 1115d may generate 3D volume data about the object 98 based on a plurality of section images. For example, if the plurality of section images are cross-sectional images, volume data about the object 98 may be acquired by accumulating the plurality of section images of the object 98 in a vertical-axis direction.

The volume data may be represented with a plurality of voxels. The term "voxel" is formed from the words "volume" and "pixel." If a pixel is defined as a point on a 2D plane, a voxel is defined as a point in a 3D space. Accordingly, a pixel includes X and Y coordinates, and a voxel includes X, Y, and Z coordinates.

The volume renderer 1116d may perform volume rendering on the 3D volume data to generate a 3D image and a 3D stereoscopic image. The volume rendering can be classified into surface rendering and direct volume rendering.

The surface rendering is to extract surface information from volume data based on predetermined scalar values and amounts of spatial changes, to convert the surface information into a geometric factor, such as a polygon or a curved patch, and then to apply a rendering technique to the geometric factor. Examples of the surface rendering are a marching cubes algorithm and a dividing cubes algorithm.

The direct volume rendering is to directly render volume data without converting volume data into a geometric factor. The direct volume rendering may represent a translucent structure because it can visualize the inside of an object as it is. The direct volume rendering may be classified into an object-order method and an image-order method according to a way of approaching volume data.

The object-order method is to search for volume data in its storage order and to synthesize each voxel with the corresponding pixel value. A representative example of the object-order method is splatting.

The image-order method is to sequentially decide pixel values in the order of scan lines of an image. Examples of the image-order method are Ray-Casting and Ray-Tracing.

The Ray-Casting is to irradiate a virtual ray from a viewpoint toward a predetermined pixel of a screen of the display 1135d, and to detect voxels through which the virtual ray has been transmitted among voxels of volume data. Then, brightness values of the detected voxels are accumulated to decide a brightness value of the corresponding pixel of the display screen. Alternatively, an average value of the detected voxels may be decided as a brightness value of the corresponding pixel of the screen of the display 1135d. Also, a weighted average value of the detected voxels may be decided as a brightness value of the corresponding pixel of the screen of the display 1135d.

The Ray-Tracing is to trace a path of a ray coming to an observer's eyes. Unlike the Ray-Casting of detecting an intersection at which a ray meets volume data, the Ray- Tracing can trace an irradiated ray and thereby reflect how the ray travels, such as reflection, refraction, etc., of the ray.

The Ray-Tracing can be classified into Forward Ray-Tracing and Backward Ray-Tracing. The Forward Ray-Tracing is to model a phenomenon in which a ray irradiated from a virtual light source arrives at volume data to be reflected, scattered, or transmitted, thereby finding a ray finally coming to an observer's eyes. The Backward Ray-Tracing is to backwardly trace a path of a ray coming to an observer's eyes.

The volume renderer 1116d may perform volume rendering on 3D volume data using one of the above-described volume rendering methods to generate a 3D image or a 3D stereoscopic image. As described above, a 3D image is a 2D projected image acquired by projecting volume data to a 2D display screen with respect to a predetermined viewpoint. A 3D stereo image is acquired by performing volume rendering on volume data with respect to two viewpoints corresponding to a human's left and right eyes to acquire a left image and a right image, and synthesizing the left image with the right image.

The display 1135d may display images created by the image processor 1110d. The display 1135d may include the first display 1136d and the second display 1137d as described above.

The storage 1145d may store data and algorithms for operations of the image processor 1110d, and also store images created by the image processor 1110d. The storage 1145d may be embodied as a volatile memory device, a non-volatile memory device, a hard disk, an optical disk, or a combination thereof. However, the storage 1145d is not limited to the above-mentioned devices, and may be embodied as any storage device well-known in the art.

In the above-described exemplary embodiments, an ultrasonic imaging apparatus, an X-ray imaging apparatus, a MRI apparatus, and a CT apparatus are described as examples of the controlled medical device, however, the kinds of the controlled medical device are not limited to the above examples. For example, the controlled medical device may be a microfluidics device, a walking assistant robot, or a Brain-Machine Interface (BMI).

Hereinafter, an exemplary embodiment of a method in which a simulation processor determines an abnormal operation of a controlled medical device will be described with reference to FIGS. 15 to 21.

Figure 15:
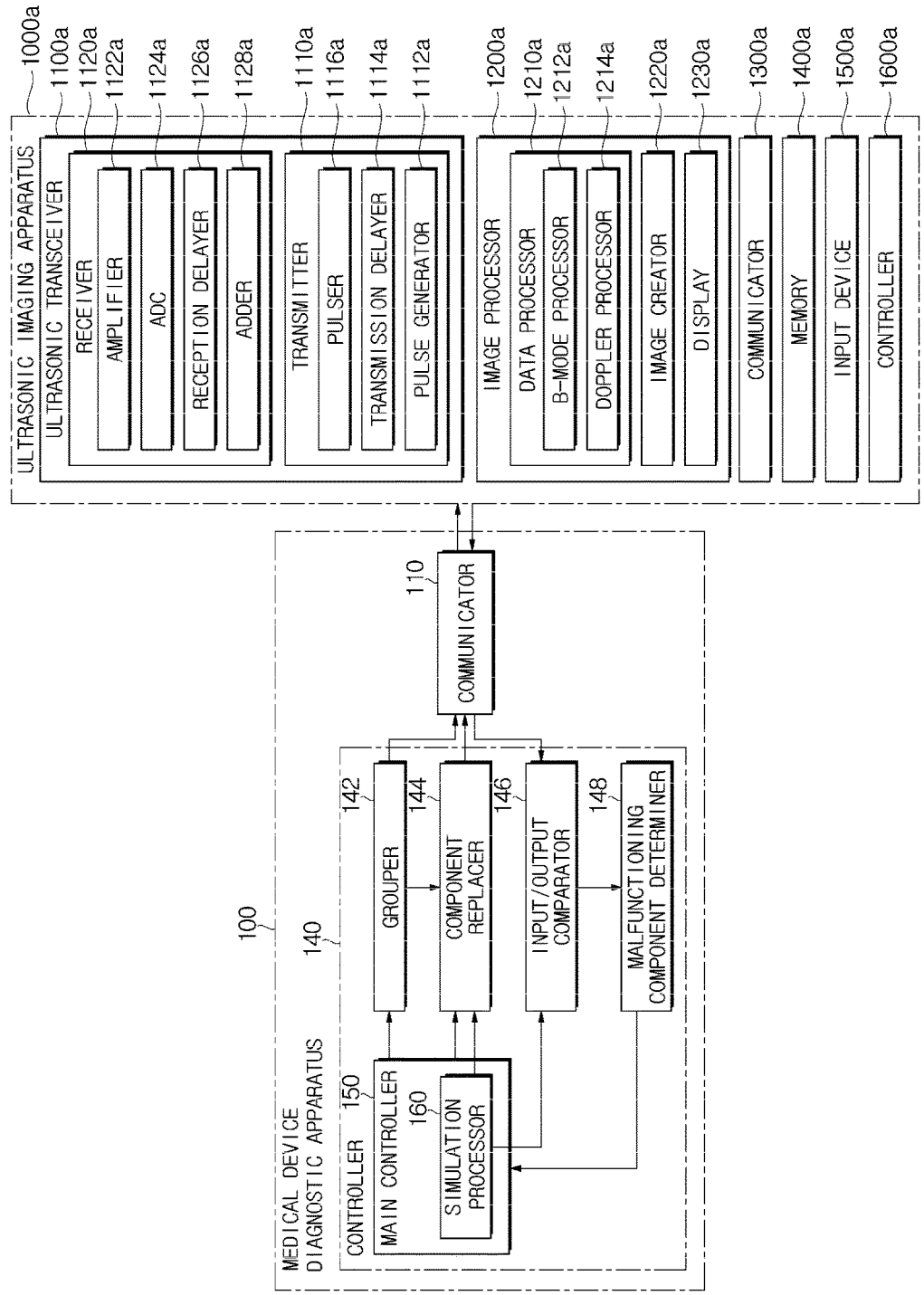
FIG. 15 is a block diagram of a medical device diagnostic apparatus when a controlled medical device is an ultrasonic imaging apparatus, according to an exemplary embodiment.
Figure 16:
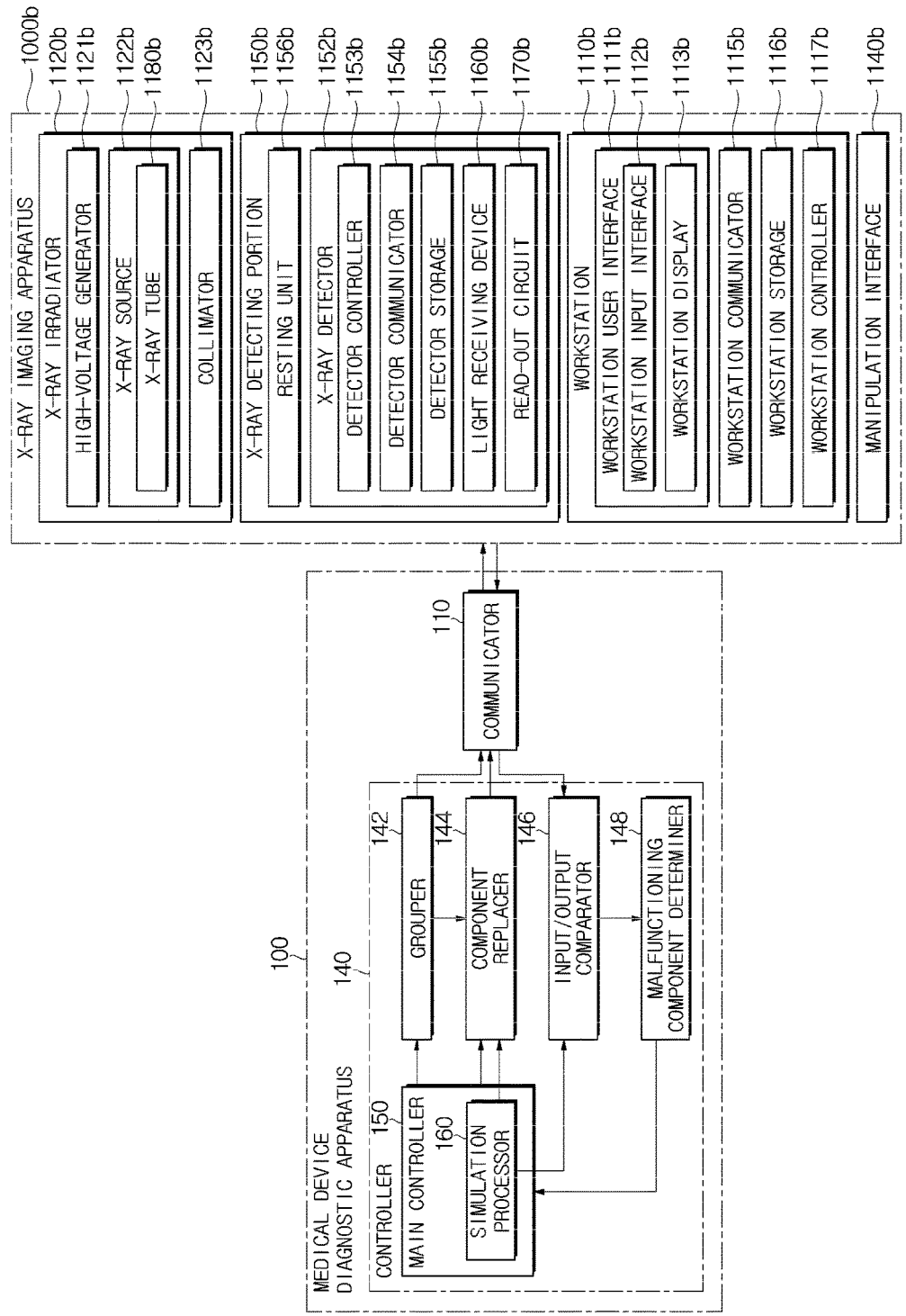
FIG. 16 is a block diagram of the medical device diagnostic apparatus when a controlled medical device is an X-ray imaging apparatus, according to an exemplary embodiment.
Figure 17:
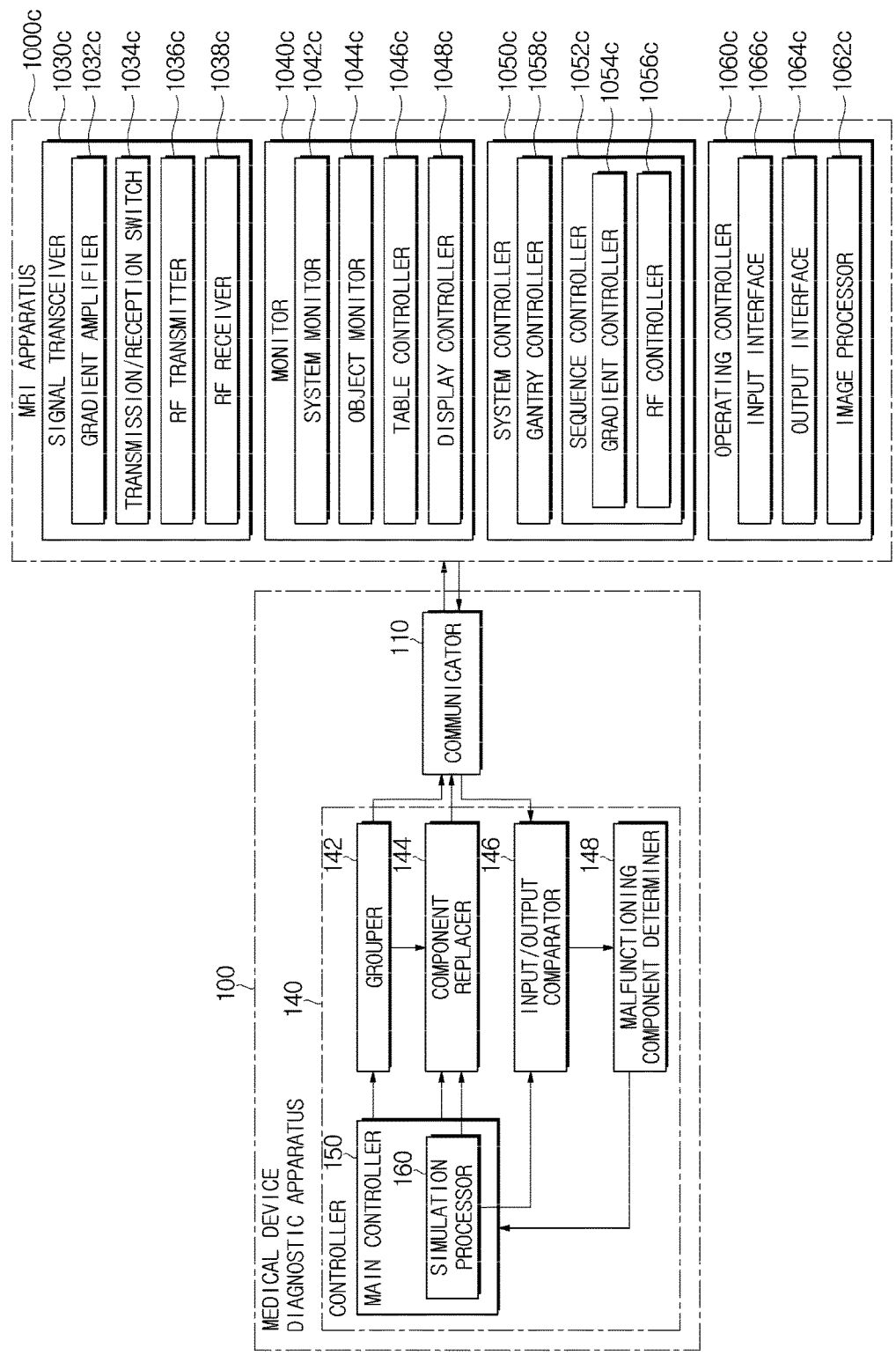
FIG. 17 is a block diagram of the medical device diagnostic apparatus when a controlled medical device is a MRI apparatus, according to an exemplary embodiment.
Figure 18:
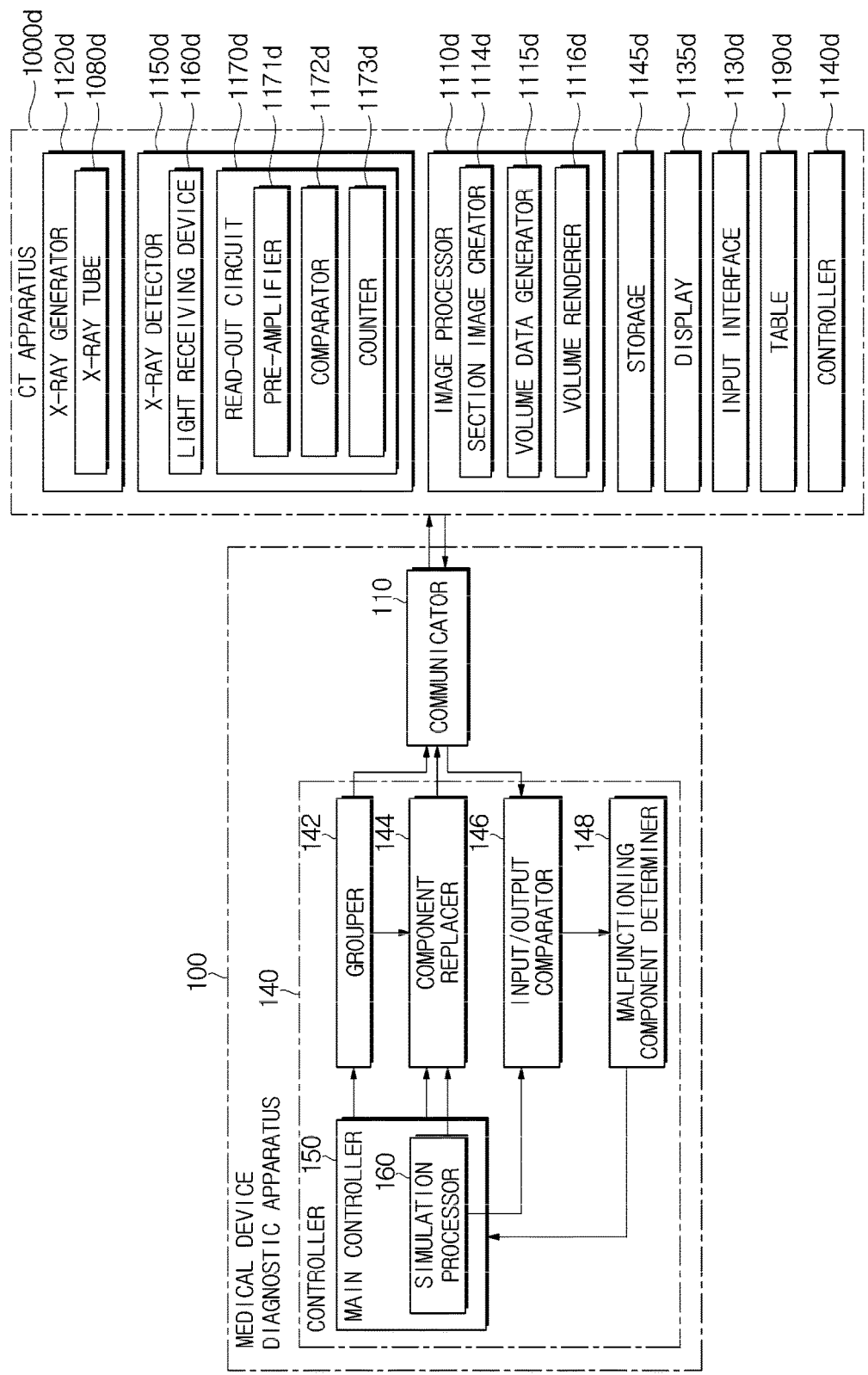
FIG. 18 is a block diagram of the medical device diagnostic apparatus when a controlled medical device is a CT apparatus, according to an exemplary embodiment.

FIG. 15 is a block diagram of the medical device diagnostic apparatus 100 when the controlled medical device 1000 is the ultrasonic imaging apparatus 1000a, FIG. 16 is a block diagram of the medical device diagnostic apparatus 100 when the controlled medical device 1000 is the X-ray imaging apparatus 1000b, FIG. 17 is a block diagram of the medical device diagnostic apparatus 100 when the controlled medical device 1000 is the MRI apparatus 1000c, and FIG. 18 is a block diagram of the medical device diagnostic apparatus 100 when the controlled medical device 1000 is the CT apparatus 1000d, according to exemplary embodiments.

Referring to FIGS. 15 to 18, the medical device diagnostic apparatus 100 may include a controller 140 and a communicator 110. The communicator 110 may be connected to the controlled medical device 1000, such as the ultrasonic imaging apparatus 1000a, the X-ray imaging apparatus 1000b, the MRI apparatus 1000c, and the CT apparatus 1000d, to perform data exchange between the medical device diagnostic apparatus 100 and the controlled medical device 1000.

The controller 140 may control operations of the medical device diagnostic apparatus 100.

Referring to FIG. 15, the ultrasonic imaging apparatus 1000a as the controlled medical device 1000 may be connected to the medical device diagnostic apparatus 100, and the ultrasonic imaging apparatus 1000a may include the ultrasonic transceiver 1100a, the image processor 1200a, the communicator 1300a, the memory 1400a, the input device 1500a, and the controller 1600a. The ultrasonic transceiver 1100a may include the receiver 1120a and the transmitter 1110a. The image processor 1200a may include the data processor 1210a, the image creator 1220a, and the display 1230a. The receiver 1120a may include the amplifier 1122a, the ADC 1124a, the reception delayer 1226a, and the adder 1128a, and the transmitter 1110a may include the pulser 1116a, the transmission delayer 1114a, and the pulse generator 1112a. The data processor 1210a may include the B-mode processor 1212a and the Doppler processor 1214a.

Referring to FIG. 16, the X-ray imaging apparatus 1000b as the controlled medical device 1000 may be connected to the medical device diagnostic apparatus 100, and the X-ray imaging apparatus 1000b may include the X-ray irradiator 1120b, the X-ray detecting portion 1150b, the workstation 1110b, and the manipulation interface 1140b. The X-ray irradiator 1120b may include the high-voltage generator 1121b, the X-ray source 1122b, and the collimator 1123b. The X-ray detecting portion 1150b may include the resting unit 1156b and the X-ray detector 1152b. The workstation 1110b may include the workstation user interface 1111b, the workstation communicator 1115b, the workstation storage 1116b, and the workstation controller 1117b. The X-ray source 1122b may include the X-ray tube 1180b, and the X-ray detector 1152b may include the detector controller 1153b, the detector communicator 1154b, the detector storage 1155b, the light receiving device 1160b, and the read-out circuit 1170b. The workstation user interface 1111b may include the workstation input interface 1112b and the workstation display 1113b.

Referring to FIG. 17, the MRI apparatus 1000c as the controlled medical device 1000 may be connected to the medical device diagnostic apparatus 100, and the MRI apparatus 1000c may include the signal transceiver 1030c, the monitor 1040c, the system controller 1050c, and the operating controller 1060c. The signal transceiver 1030c may include the gradient amplifier 1032c, the transmission/reception switch 1034c, the RF transmitter 1036c, and the RF receiver 1038c. The monitor 1040c may include the system monitor 1042c, the object monitor 1044c, the table controller 1046c, and the display controller 1048c. The system controller 1050c may include the gantry controller 1058c and the sequence controller 1052c. The operating controller 1060c may include the input interface 1066c, the output interface 1064c, and the image processor 1062c.

Referring to FIG. 18, the CT apparatus 1000d as the controlled medical device 1000 may be connected to the medical device diagnostic apparatus 100, and the CT apparatus 1000d may include the X-ray generator 1120d, the X-ray detector 1150d, the image processor 1110d, the storage 1145d, the display 1035d, the input interface 1130d, the table 1190d, and the controller 1140d. The X-ray generator 1120d may include an X-ray tube 1080d, and the X-ray detector 1150d may include the light receiving device 1160d and the read-out circuit 1170d. The image processor 1110d may include the section image creator 1114d, the volume data generator 1115d, and the volume renderer 1116d. The read-out circuit 1170d may include the pre-amplifier 1171d, the comparator 1172d, and the counter 1173d.

Figure 19:
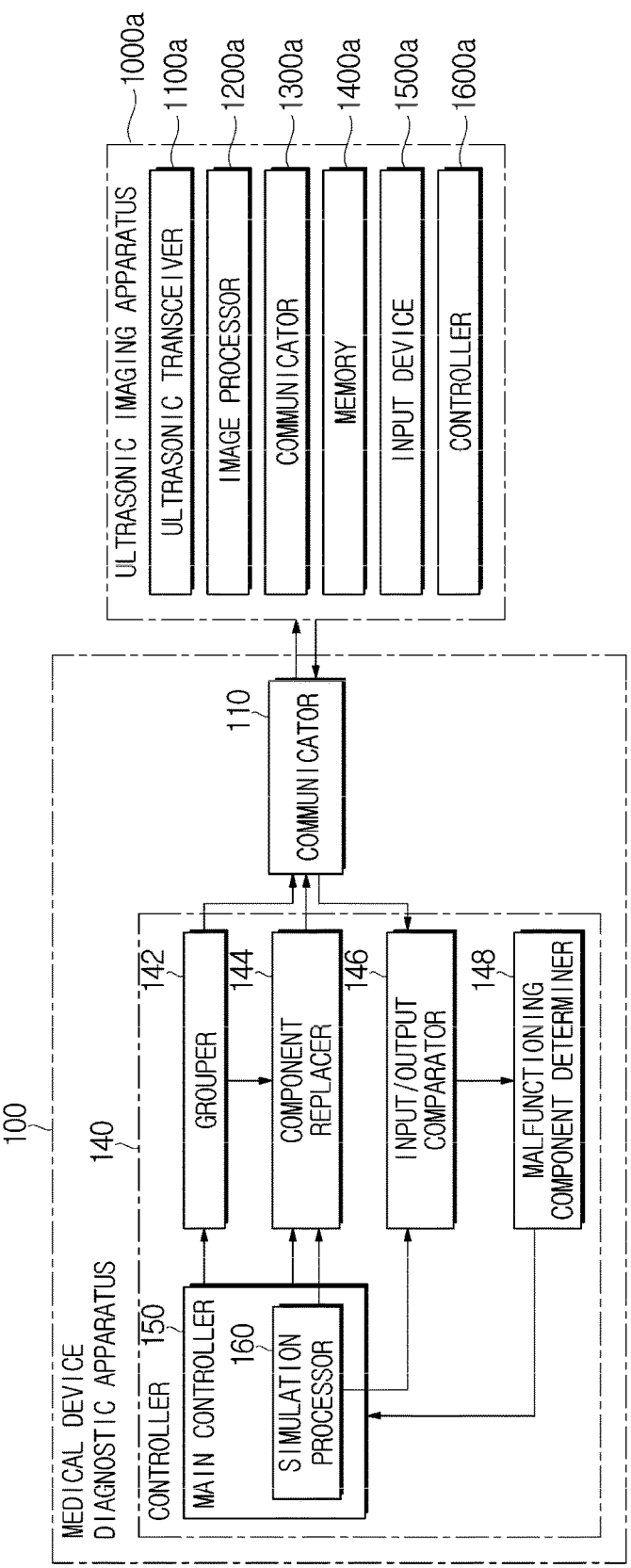
FIGS. 19, 20, and 21 are views illustrating a method in which the medical device diagnostic apparatus diagnoses a malfunction of a controlled medical device, according to an exemplary embodiment.
Figure 20:
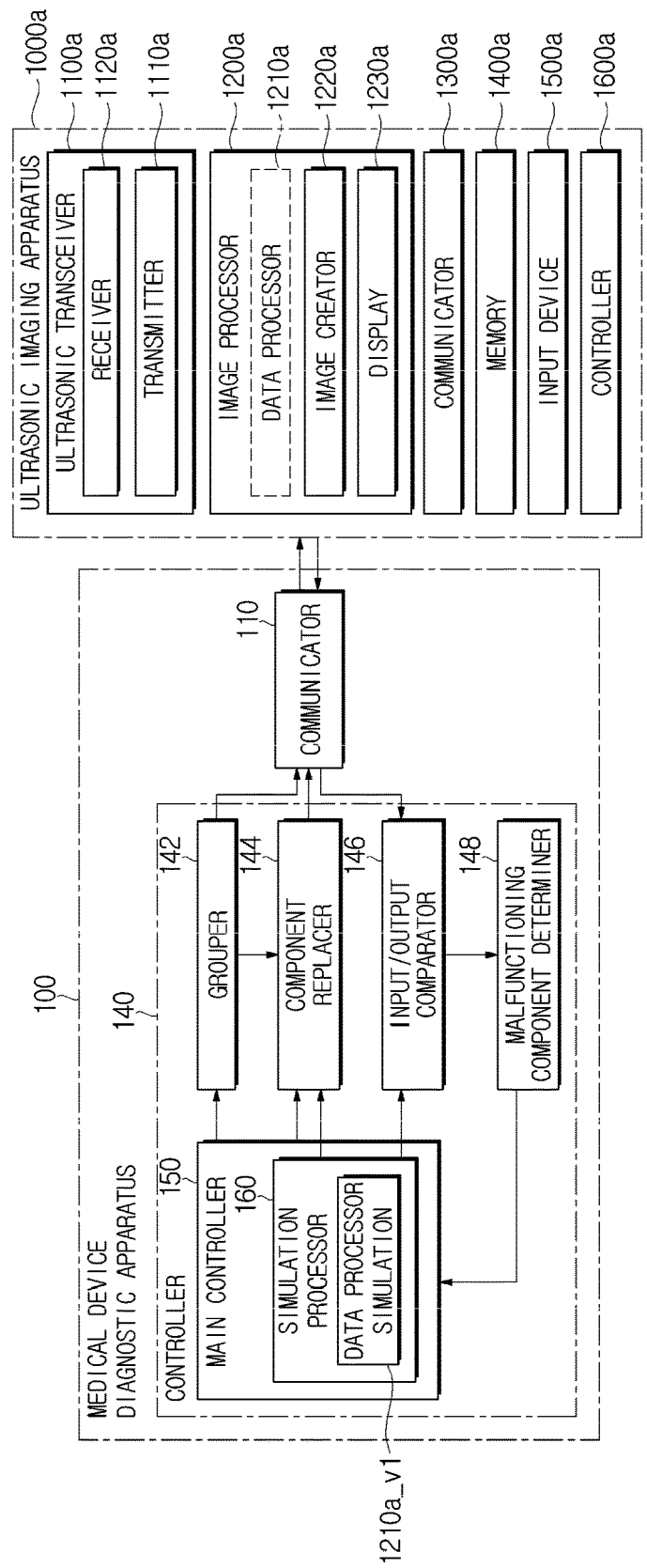
Figure 21:
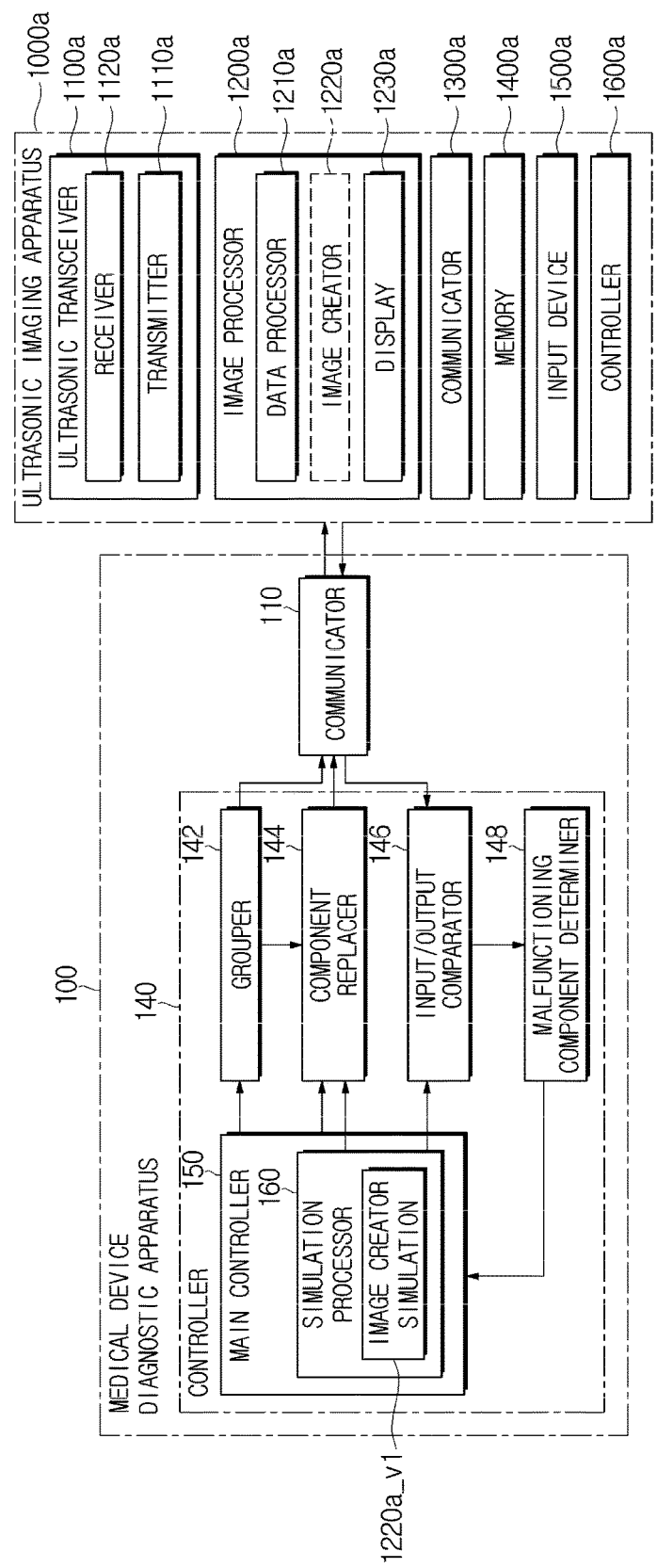

FIGS. 19, 20, and 21 are views illustrating a method in which the medical device diagnostic apparatus 100 diagnoses an abnormal operation of the controlled medical device 1000, according to an exemplary embodiment.

Referring to FIGS. 19 to 21, the controller 140 may control operations of the medical device diagnostic apparatus 100, and may include the main controller 150, the grouper 142, the component replacer 144, the input/output comparator 146, and the malfunctioning component determiner 148.

The main controller 150 may receive data about components of the controlled medical device 1000 through the communicator 110, and replace the components of the controlled medical device 1000 with a simulation. The main controller 150 may receive information about a plurality of components included in the ultrasonic imaging apparatus 1000a from the ultrasonic imaging apparatus 1000a, and transfer the information about the plurality of components to the grouper 142 and the component replacer 144 so that the grouper 142 groups the plurality of components of the ultrasonic imaging apparatus 1000a, and the component replacer 144 replaces a component included in the ultrasonic imaging apparatus 1000a.

The main controller 150 may include the simulation processor 160. The simulation processor 160 may create a virtual medical device corresponding to the controlled medical device 1000 connected to the medical device diagnostic apparatus 100. If the ultrasonic imaging apparatus 1000a as the controlled medical device 1000 is connected to the medical device diagnostic apparatus 100, the simulation processor 160 may configure virtual components corresponding to the ultrasonic transceiver 1100a, the image processor 1200a, the communicator 1300a, the memory 1400a, the input device 1500a, and the controller 1600a, acquire input values input to and output values output from the individual virtual components, and transfer the input values and the output values to the component replacer 144 and the input/output comparator 146.

The grouper 142 may group the plurality of components included in the controlled medical device 1000. If the controlled medical device 1000 is the ultrasonic imaging apparatus 1000a, the grouper 142 may set the ultrasonic transceiver 1100a, the image processor 1200a, the communicator 1300a, the memory 1400a, the input device 1500a, and the controller 1600a to upper components, set the receiver 1120a and the transmitter 1110a to lower components of the ultrasonic transceiver 1100a, and set the data processor 1210a, the image creator 1220a, and the display 1230a to lower components of the image processor 1200a.

After the grouper 142 sets the upper components and the lower components, the controller 140 may replace the upper components with reference data corresponding to the upper components, and determine whether the controlled medical device 1000 operates normally. Also, if the controller 140 determines that a upper component operates abnormally, the controller 140 may replace lower components included in the upper component with reference data corresponding to the lower components, and then determine whether the controlled medical device 1000 operates normally.

For example, as shown in FIG. 19, the controller 140 may replace the ultrasonic transceiver 1100a, the image processor 1200a, the communicator 1300a, the memory 1400a, the input device 1500a, and the controller 1600a with the simulation processor 160 corresponding to the above-mentioned components, and then determine whether the controlled medical device 1000 operates normally. If the controller 140 determines that the image processor 1200a operates abnormally, the controller 140 may replace the data processor 1210a, the image creator 1220a, and the display 1230a, which are lower components of the image processor 1200a, with the simulation processor 160, and then determine whether the controlled medical device 1000 operate normally.

The component replacer 144 may select one of the plurality of components included in the controlled medical device 1000, or a plurality of upper components or a plurality of lower components of the controlled medical device 1000. The component replacer 144 may electrically separate the selected component(s) from the controlled medical device 1000, replace the selected component(s) with data corresponding to the selected component(s) in the simulation processor 160, and then drive the controlled medical device 1000.

For example, as shown in FIG. 20, if the controller 140 determines that the image processor 1200a among the upper components included in the ultrasonic imaging apparatus 1000a operates abnormally, the component replacer 144 may select the data processor 1210a among the lower components of the image processor 1200a. Then, the component replacer 144 may load the simulation processor 160 of the main controller 150, replace the data processor 1210a with a data processor simulation 1210_v1 corresponding to the data processor 1210a in the simulation processor 160, and then drive the ultrasonic imaging apparatus 1000a.

If the input/output comparator 146 and the malfunctioning component determiner 148 determine that the data processor 1210a operates normally, the component replacer 144 may select another component in the image processor 1200a. For example, as shown in FIG. 21, the component replacer 144 may select the image creator 1220a that has not been selected among the lower components of the image processor 1200a. Then, the component replacer 144 may load the simulation processor 160 of the main controller 150, replace the image creator 1220a with an image creator simulation 1220a_v1 corresponding to the image creator 1220a in the simulation processor 160 with, and then drive the ultrasonic imaging apparatus 1000a.

The input/output comparator 146 may read input and output data of a component selected among the plurality of components included in the controlled medical device 1000, compare the read input and output data to input and output data of a simulation corresponding to the selected component, and transfer the results of the comparison to the malfunctioning component determiner 148.

For example, as shown in FIG. 20, the input/output comparator 146 may read input and output data of the data processor 1210a, calculate a difference between the read input and output data and input and output data of the data processor simulation 1210a_v1 corresponding to the data processor 1210a in the simulation processor 160, and transfer the difference to the malfunctioning component determiner 148.

Also, as shown in FIG. 21, the input/output comparator 146 may read input and output data of the image creator 1220a, calculate a difference between the input and output data of the image creator 1220a and input and output data of the image creator simulation 1220a_v1 corresponding to the image creator 1220a in the simulation processor 160, and transfer the difference to the malfunctioning component determiner 148.

Operation in which the component replacer 144 loads reference data, and operation in which the input/output comparator 146 reads input and output data of the controlled medical device 1000 and input and output data of reference data may be performed using Equation (1) below.

```
PseudoSimulationInterface
{
    void Read(deviceID, funtionalID, functionalParam-
        eterAsInput);

void Write(deviceID, funtionalID, functionalParam-
        eterAsOutput);
}                                                    (1)
```

Equation (1) is used by the controller 140 to write reference data and read input and output data. In Equation (1), PseudoSimulationInterface represents a group of functions for the controller 140 to read and write data, void Read( ) represents a function for reading received input/output data, deviceID represents a device ID, functionID represents a function ID, functionalParameterAsInput represents an input functional parameter, void Write( ) represents a function for writing reference data, and functionalParameterAsOutput represents an output functional parameter.

The device ID is data for identifying each component of the controlled medical device 1000. The device ID may include a device model, a serial number, and a device IP. The device model may be a model name of a device manufactured by a manufacturing company. The serial number may be information to identify each of a plurality of devices belonging to the same device model, and may be a manufactured date or a serial number of the corresponding device. The device IP may be information to identify each of a plurality of devices belonging to the same device model and having the same serial number, and may be a protocol set to communicate with the medical device diagnostic apparatus 100.

The malfunctioning component determiner 148 may determine whether the selected component operates abnormally, based on the result of the comparison between the input and output data of the selected component and the input and output data of the simulation corresponding to the selected component in the simulation processor 160, the result of the comparison acquired by the input/output comparator 146.

The malfunctioning component determiner 148 may recognize the selected component based on the device ID, and determine whether the selected component operates abnormally, based on the difference between the input and output data of the selected component and the input and output data of the corresponding simulation, the difference acquired by the input/output comparator 146.

For example, if the malfunctioning component determiner 148 determines that the difference between the input and output data of the selected component and the input and output data of the simulation is greater than a predetermined value, the malfunctioning component determiner 148 may determine that the selected component operates abnormally. If the malfunctioning component determiner 148 determines that the difference between the input and output data of the selected component and the input and output data of the simulation is smaller than or equal to the predetermined value, the malfunctioning component determiner 148 may determine that the selected component operates normally. Here, the predetermined value may be an allowable error between an input and an output when the selected component operates normally. That is, when the difference between the input and output data of the selected component and the input and output data of the simulation exceeds the allowable error, the malfunctioning component determiner 148 may determine that the selected component operates abnormally. The predetermined value may vary depending on the kinds of components, and may have been set in advance according to the kind or specification of the controlled medical device 1000 when the controlled medical device 1000 was manufactured or designed.

Hereinafter, an exemplary embodiment of a method of determining whether a controlled medical device operates abnormally based on normal input/output data will be described with reference to FIGS. 22 to 28.

Figure 22:
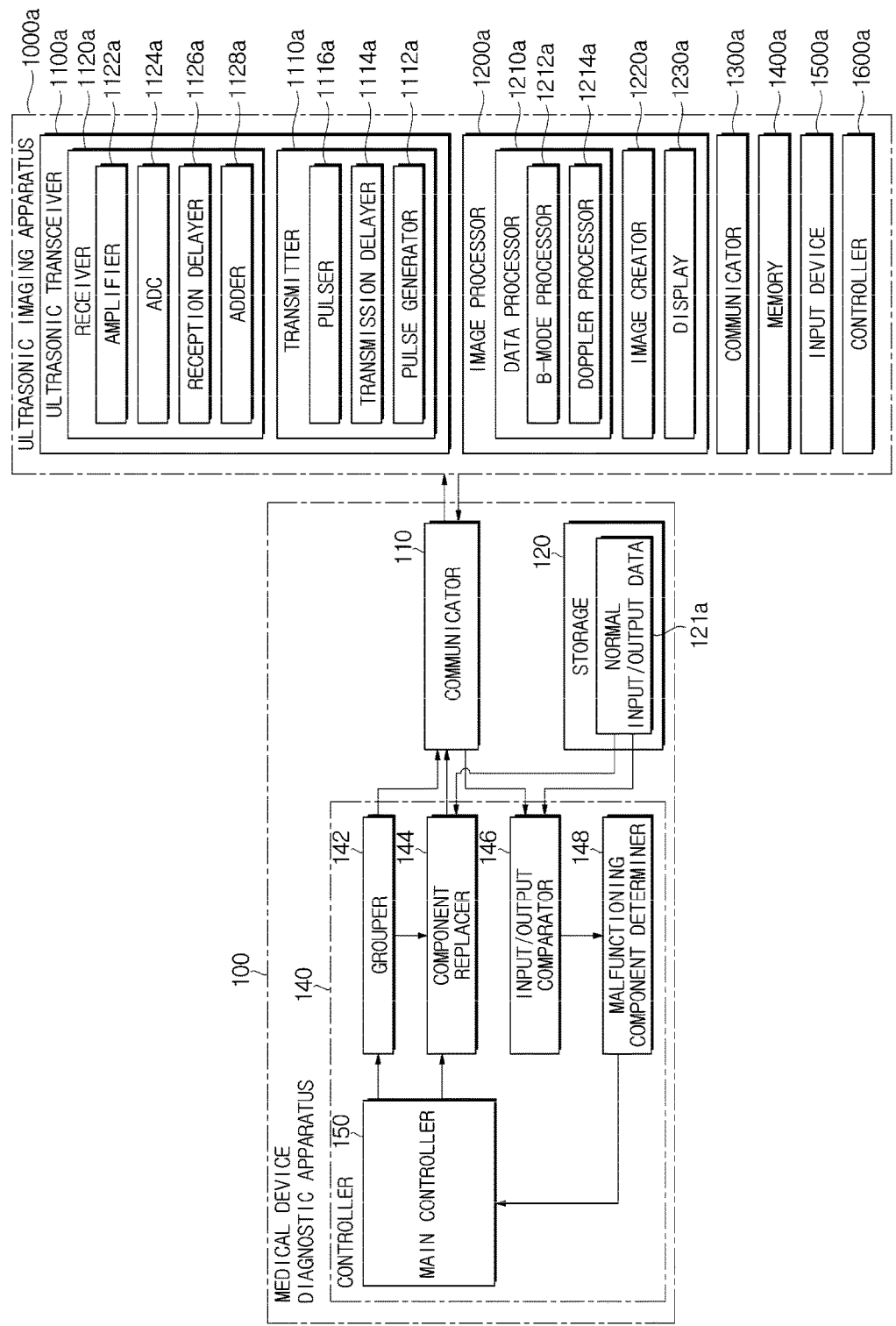
FIG. 22 is a block diagram of a medical device diagnostic apparatus when a controlled medical device is an ultrasonic imaging apparatus, according to another exemplary embodiment.
Figure 23:
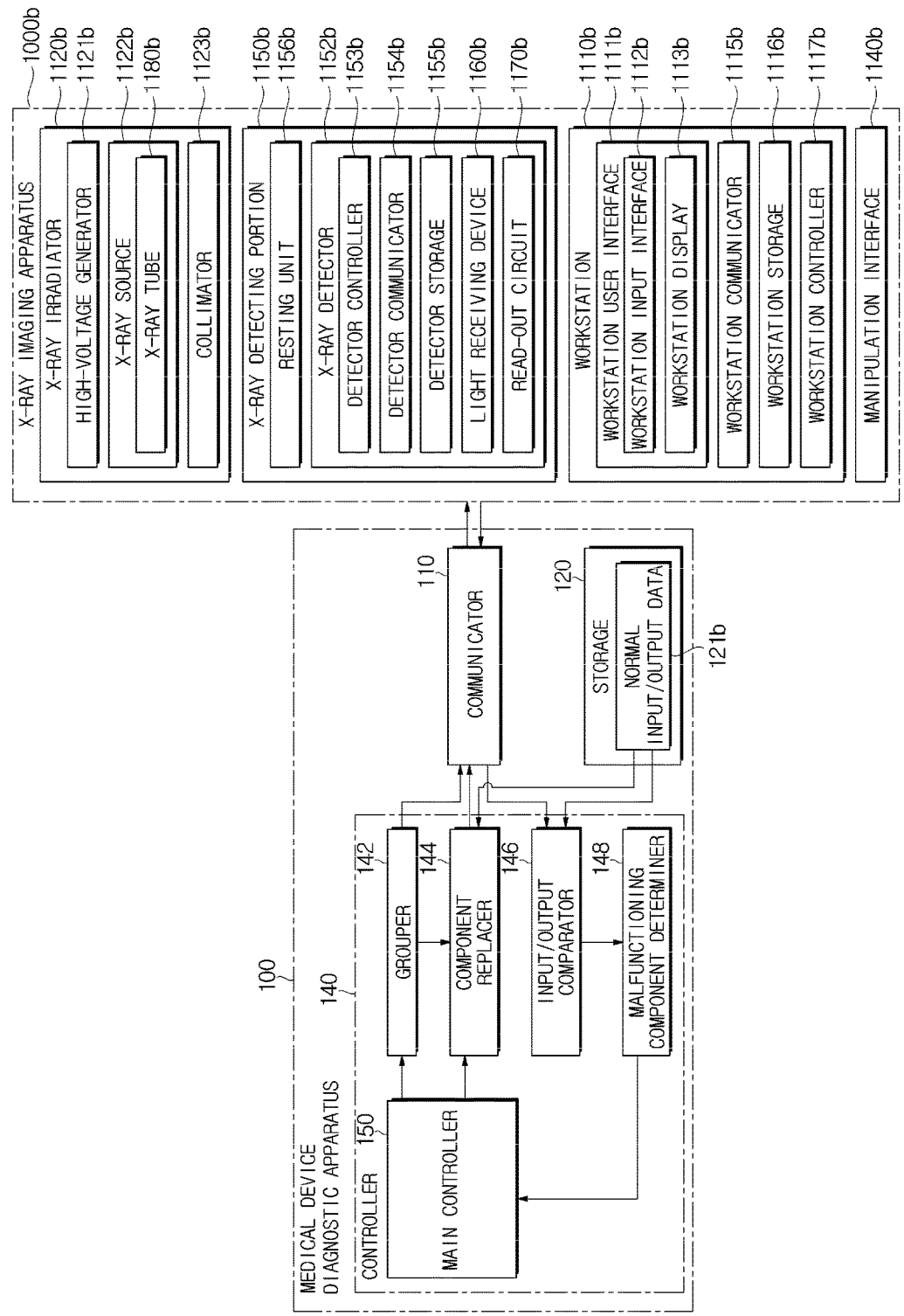
FIG. 23 is a block diagram of the medical device diagnostic apparatus when a controlled medical device is an X-ray imaging apparatus, according to another exemplary embodiment.
Figure 24:
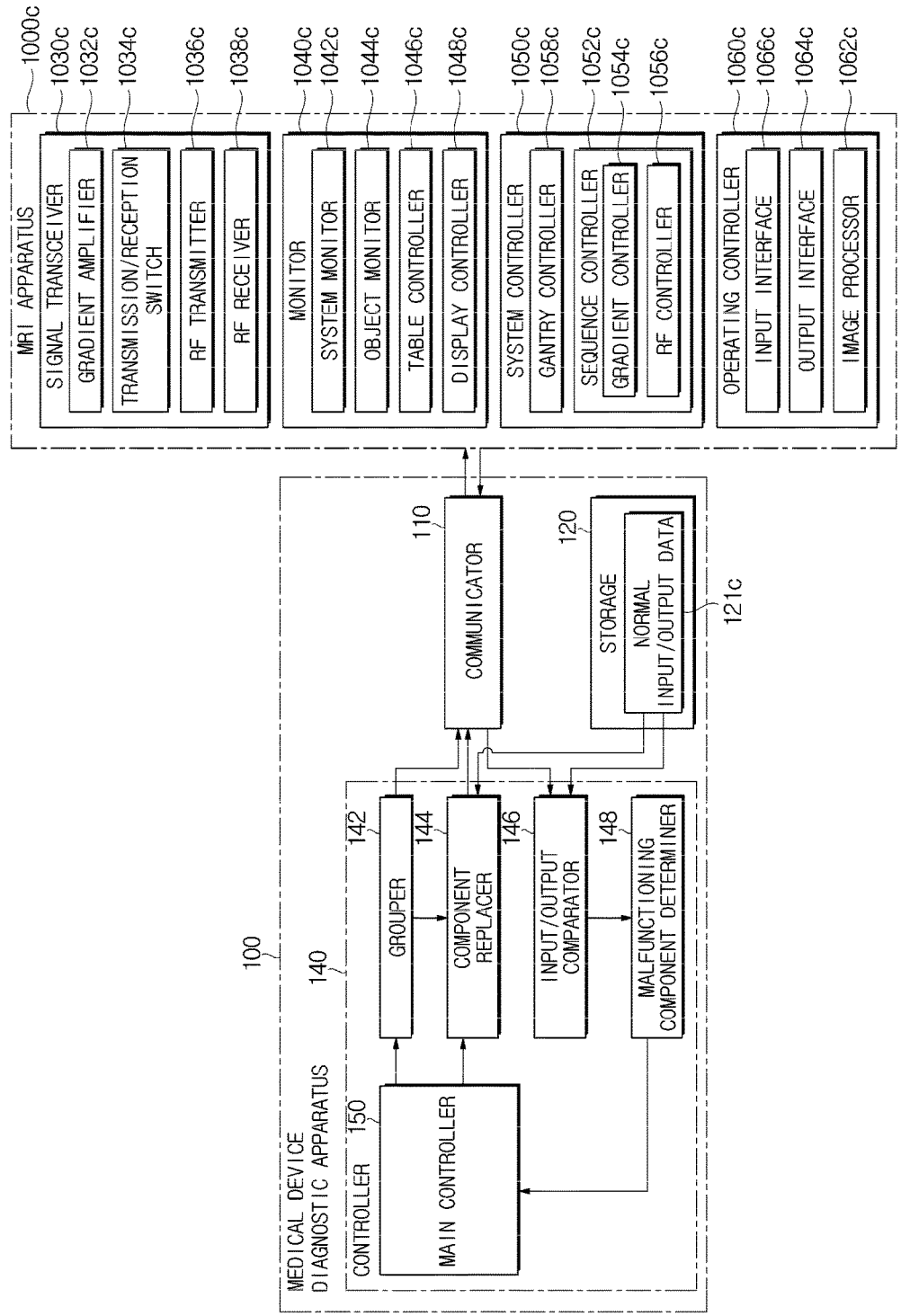
FIG. 24 is a block diagram of the medical device diagnostic apparatus when a controlled medical device is a MRI apparatus, according to another exemplary embodiment.
Figure 25:
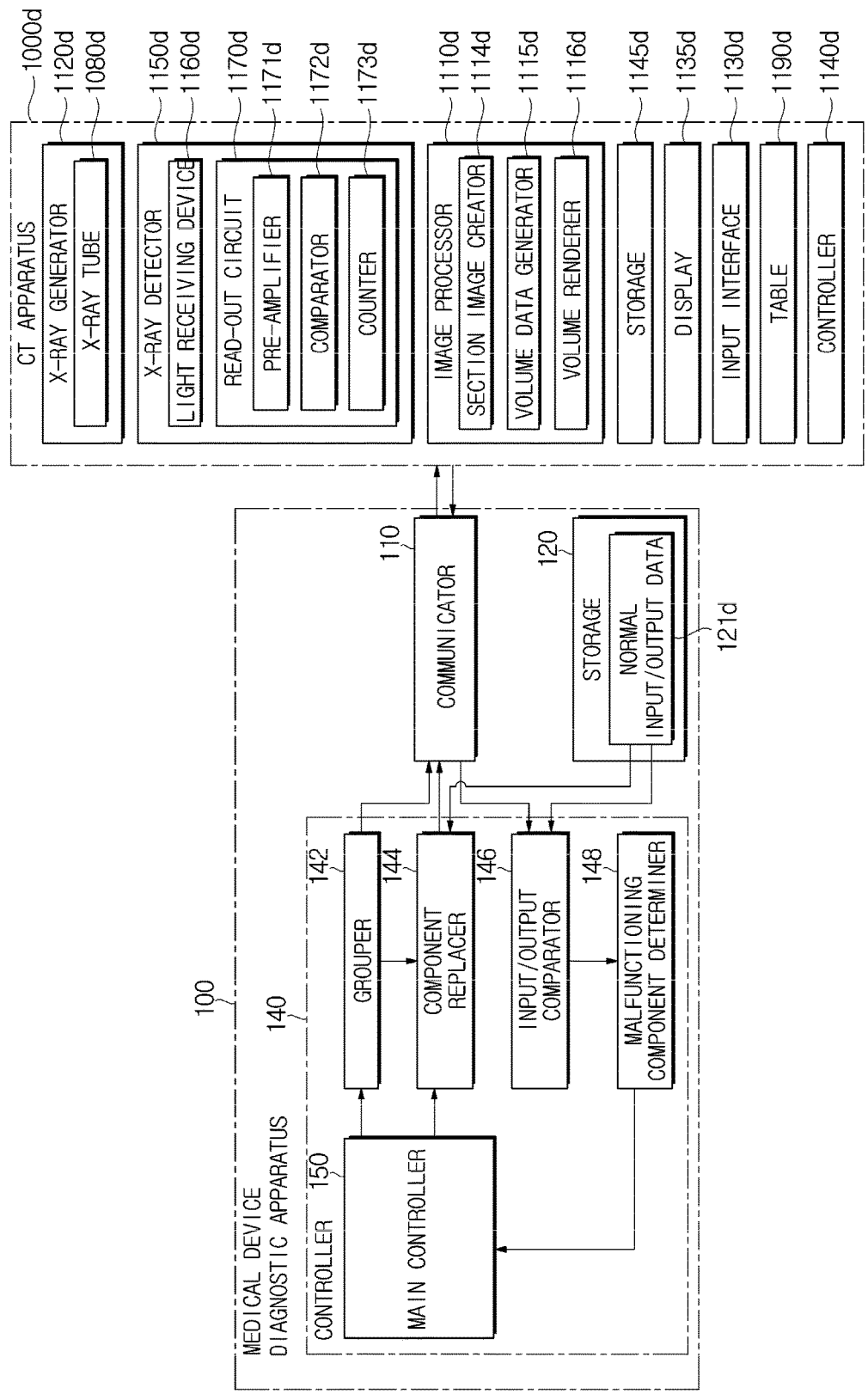
FIG. 25 is a block diagram of the medical device diagnostic apparatus when a controlled medical device is a CT apparatus, according to another exemplary embodiment.

FIG. 22 is a block diagram of the medical device diagnostic apparatus 100 when the controlled medical device 1000 is the ultrasonic imaging apparatus 1000*a*, FIG. 23 is a block diagram of the medical device diagnostic apparatus 100 when the controlled medical device 1000 is the X-ray imaging apparatus 1000*b*, FIG. 24 is a block diagram of the medical device diagnostic apparatus 100 when the controlled medical device 1000 is the MRI apparatus 1000*c*, and FIG. 25 is a block diagram of the medical device diagnostic apparatus 100 when the controlled medical device 1000 is the CT apparatus 1000*d*, according to exemplary embodiments.

Referring to FIGS. 22 to 25, the medical device diagnostic apparatus 100 may include the controller 140 and the communicator 110. The communicator 110 may be connected to the controlled medical device 1000, such as the ultrasonic imaging apparatus 1000*a*, the X-ray imaging apparatus 1000*b*, the MRI apparatus 1000*c*, and the CT apparatus 1000*d*, to perform data exchange between the medical device diagnostic apparatus 100 and the controlled medical device 1000.

The controller 140 may control operations of the medical device diagnostic apparatus 100.

As the controlled medical device 1000, the X-ray imaging apparatus 1000*a*, the X-ray imaging apparatus 1000*b*, the MRI apparatus 1000*c*, or the CT apparatus 1000*d* may be connected to the medical device diagnostic apparatus 100, as described above.

Figure 26:
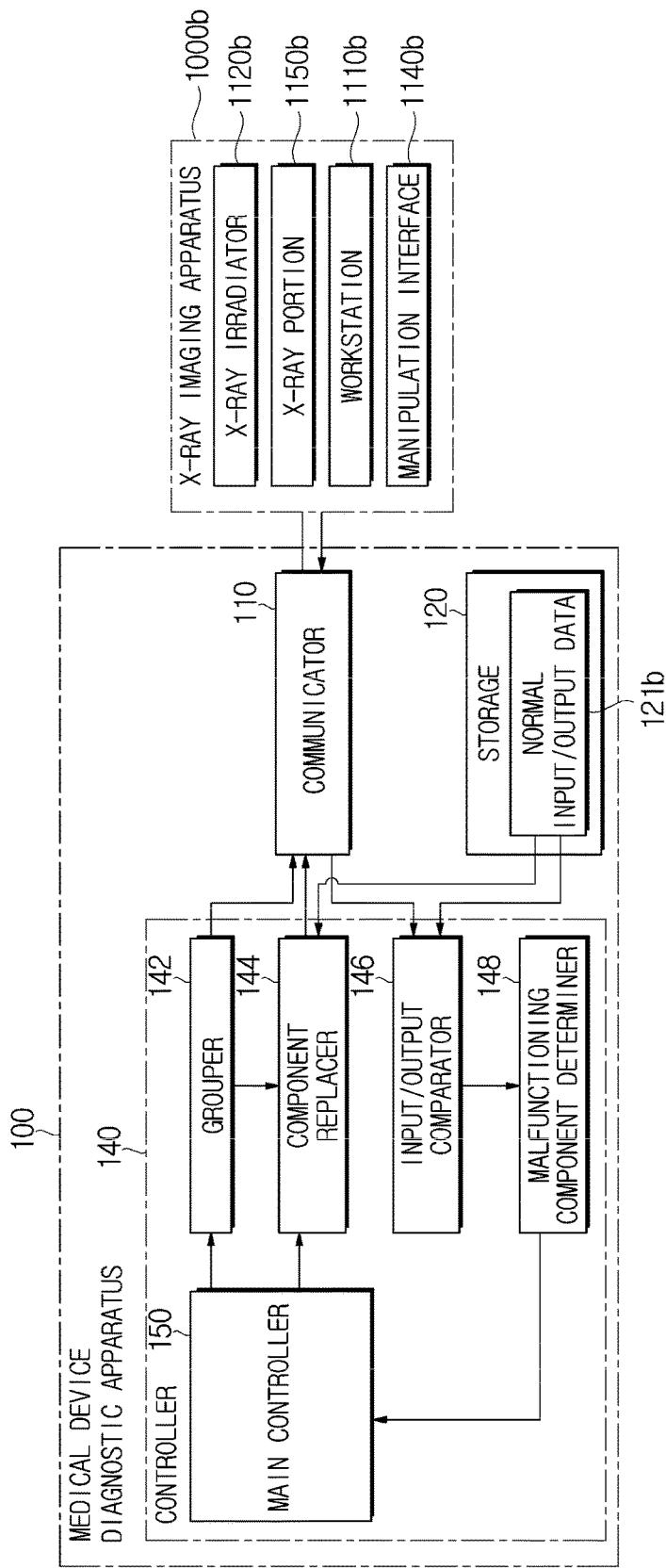
FIGS. 26, 27, and 28 are views illustrating a method in which the medical device diagnostic apparatus diagnoses a malfunction of a controlled medical device, according to another exemplary embodiment.
Figure 27:
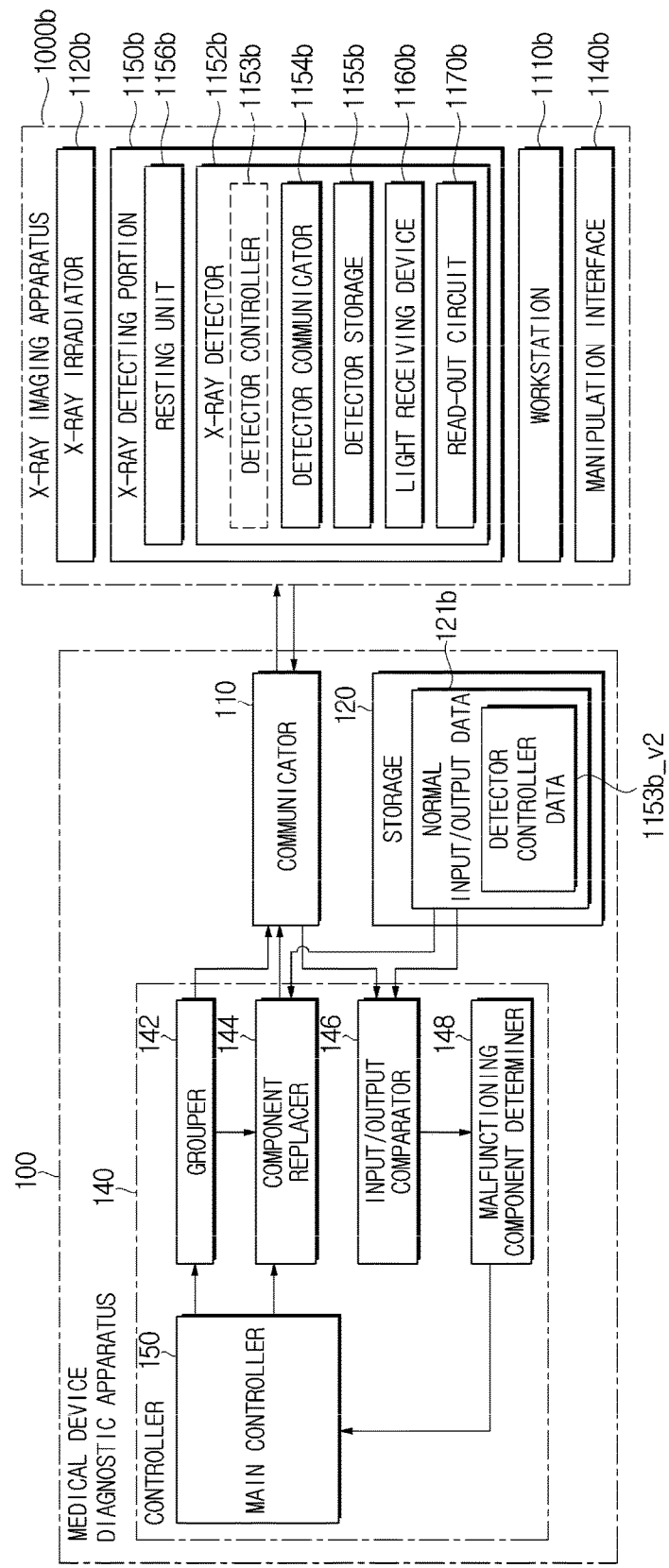
Figure 28:
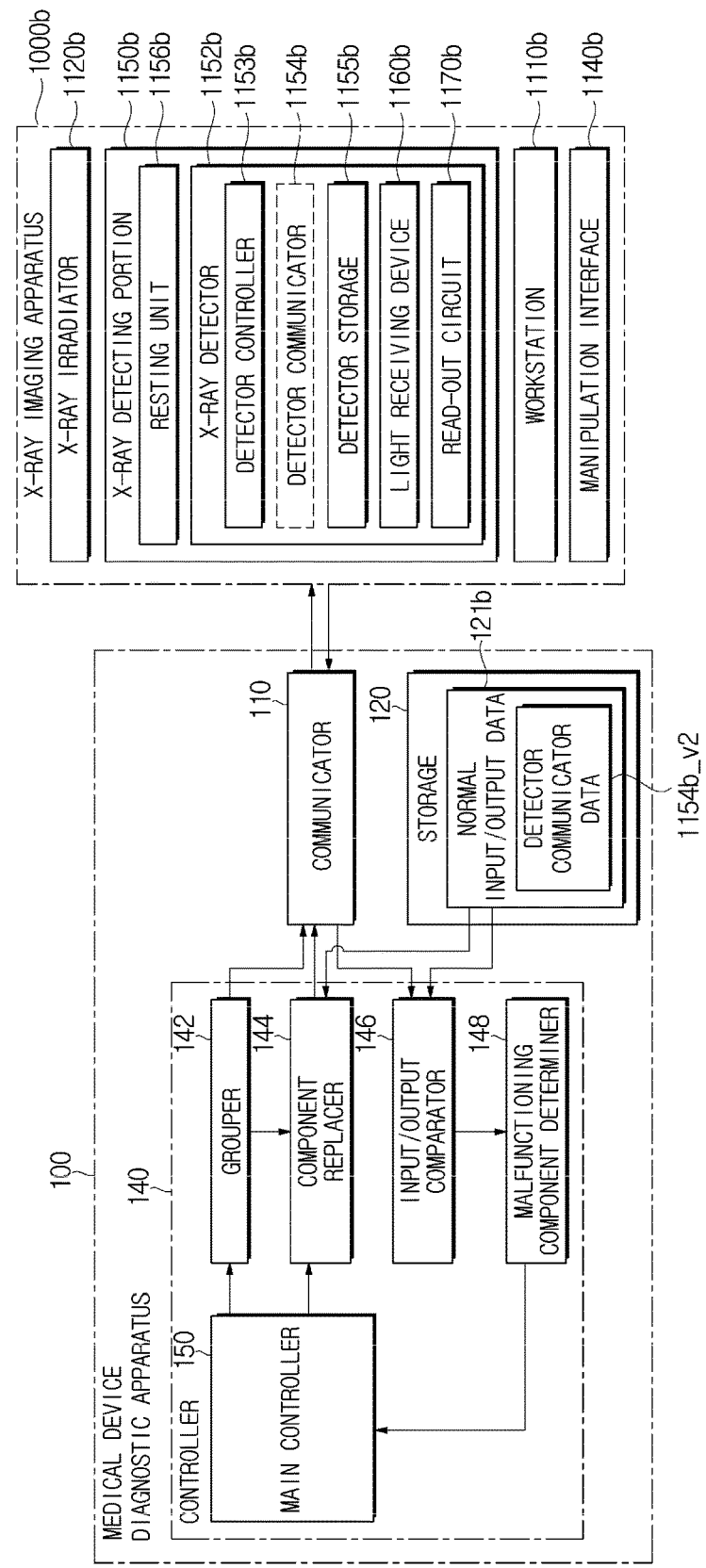

FIGS. 26, 27, and 28 are views illustrating a method in which the medical device diagnostic apparatus 100 diagnoses a malfunction of the controlled medical device 1000, according to an exemplary embodiment.

Referring to FIGS. 26 to 28, the medical device diagnostic apparatus 100 may include the communicator 110, the storage 120, and the controller 140.

The communicator 110 may be connected to the controlled medical device 1000 to transmit and receive data to and from the controlled medical device 1000. The communicator 110 may be the same as or different from the communicator 110 of FIG. 1.

The storage 120 may store normal input/output data 121 (121*a*, 121*b*, 121*c*, or 121*d*). The normal input/output data 121 may be data of inputs and outputs or data of outputs to inputs with respect to the plurality of components included in the controlled medical device 1000. The normal input/output data 121 may be data of inputs and outputs or data of outputs to inputs with respect to the upper and lower components included in the controlled medical device 1000.

The normal input/output data 121 may be stored in a look-up table or a numerical expression. The normal input/output data 121 may be predetermined data set according to the kind or specification of the controlled medical device 1000 when the controlled medical device 1000 was manufactured or designed.

The controller 140 may control operations of the medical device diagnostic apparatus 100. The controller 140 may include the main controller 150, the grouper 142, the component replacer 144, the input/output comparator 146, and the malfunctioning component determiner 148.

The main controller 150 may receive data about the configuration of the controlled medical device 1000 through the communicator 110, and use the received data to replace a component of the controlled medical device 1000 with normal input/output data 121. The main controller 150 may receive information about the plurality of components included in the X-ray imaging apparatus 1000b from the X-ray imaging apparatus 1000b, and transfer the received information to the grouper 142 and the component replacer 144 so that the grouper 142 groups the plurality of components, and the component replacer 144 replaces a component included in the X-ray imaging apparatus 1000b.

The grouper 142 may group the plurality of components included in the controlled medical device 1000. If the controlled medical device 1000 is the X-ray imaging apparatus 1000b, the grouper 142 may set the X-ray irradiator 1120b, the X-ray detecting portion 1150b, the workstation 1110b, the manipulation interface 1140b to upper components, set the high-voltage generator 1121b, the X-ray source 1122b, and the collimator 1123b to lower components of the X-ray irradiator 1120b, set the resting unit 1156b and the X-ray detector 1152b to lower components of the X-ray detecting portion 1150b, and set the workstation user interface 1111b, the workstation communicator 1115b, the workstation storage 1116b, and the workstation controller 1117b to lower components of the workstation 1110b.

After the grouper 142 decides the upper groups and the lower groups, the controller 140 may replace the upper components with reference data corresponding to the upper components, and determine whether the X-ray imaging apparatus 1000b operates normally. If the controller 140 determines that an upper component operates abnormally, the controller 140 may replace lower components included in the corresponding upper component with reference data corresponding to the corresponding lower components, and determine whether the X-ray imaging apparatus 1000b operates normally.

For example, as shown in FIG. 26, the controller 140 may replace the X-ray irradiator 1120b, the X-ray detecting portion 1150b, the workstation 1110b, and the manipulation interface 1140b with normal input/output data 121b corresponding to the X-ray irradiator 1120b, the X-ray detecting portion 1150b, the workstation 1110b, and the manipulation interface 1140b, and determine whether the X-ray imaging apparatus 1000b operates normally. If the controller 140 determines that the X-ray detecting portion 1150b operates abnormally, the controller 140 may replace the resting unit 1156b and the X-ray detector 1152b, which are the lower components of the X-ray detecting portion 1150b, with the corresponding normal input/output data 121b, and determine whether the X-ray imaging apparatus 1000b operates normally. Also, if the controller 140 determines that the X-ray detector 1152b operates abnormally, the controller 140 may replace the detector controller 1153b, the detector communicator 1154b, the detector storage 1155b, the light receiving device 1160b, and the read-out circuit 1170b, which are the lower components of the X-ray detector 1152b, with the corresponding normal input/output data 121b, and determine whether the X-ray imaging apparatus 1000b operates normally.

The component replacer 144 may select one of the plurality of components included in the controlled medical device 1000, or a plurality of upper components or a plurality of lower components included in the controlled medical device 1000. The component replacer 144 may electrically separate the selected component(s) from the controlled medical device 1000, replace the selected component(s) with data corresponding to the selected component(s) in normal input/output data 121b, and then drive the controlled medical device 1000.

For example, as shown in FIG. 27, if the controller 140 determines that the X-ray detector 1152b among the upper components included in the X-ray detecting portion 1150b of the X-ray imaging apparatus 1000b operates abnormally, the component replacer 144 may select the detector controller 1153b among the lower components of the X-ray detector 1152b. Then, the component replacer 144 may load the normal input/output data 121b stored in the storage 120, replace the detector controller 1153b with detector controller data 1153b_v2 corresponding to the detector controller 1153b in the normal input/output data 121b, and then drive the X-ray imaging apparatus 1000b.

If the input/output comparator 146 and the malfunctioning component determiner 148 determine that the data controller 1153b operates normally, the component replacer 144 may select another component among the lower components of the X-ray detector 1152b. That is, the component replacer 144 may select the detector communicator 1154b that has not been selected among the lower components of the X-ray detector 1152b, as shown in FIG. 28. Then, the component replacer 144 may load the normal input/output data 121b stored in the storage 120, replace the detector communicator 1154b with detector communicator data 1154b_v2 corresponding to the detector communicator 1154b in the normal input/output data 121b, and then drive the X-ray imaging apparatus 1000b.

The input/output comparator 146 may read input and output data of a component selected among the plurality of components included in the controlled medical device 1000, compare the input and output data of the selected component to input and output data corresponding to the selected component in the normal input/output data 121b, and then transfer the result of the comparison to the malfunctioning component determiner 148.

For example, the input/output comparator 146 may read input and output data of the detector communicator 1154b, calculate a difference between the input and output data of the detector communicator 1154b and detector communicator data 1154b_v2 corresponding to the detector communicator 1154b in the normal input/output data 121b, and then transfer the difference to the malfunctioning component determiner 148, as shown in FIG. 28.

Operation in which the component replacer 144 loads reference data, and operation in which the input/output comparator 146 reads input and output data of a component of the controlled medical device 1000 and reference input and output data may be performed using Equation (1) defined above.

The malfunctioning component determiner 148 may determine whether the selected component operates abnormally, based on the result of the comparison between the input and output data of the selected component and the input and output data corresponding to the selected component in the normal input/output data 121b.

The malfunctioning component determiner 148 may recognize the selected component based on the device ID, and determine whether the selected component operates abnormally, based on a difference between input and output data of the selected component and input and output data of the normal input/output data 121*b*, the difference acquired by the input/output comparator 146.

For example, if the malfunctioning component determiner 148 determines that a difference between input and output data of the selected component and the corresponding normal input/output data 121*b* is greater than a predetermined value, the malfunctioning component determiner 148 may determine that the selected component operates abnormally. If the malfunctioning component determiner 148 determines that the difference between the input and output data of the selected component and the corresponding normal input/output data 121*b* is smaller than or equal to the predetermined value, the malfunctioning component determiner 148 may determine that the selected component operates normally. Here, the predetermined value may be an allowable error between an input and an output when the selected component operates normally. If the difference between the input and output data of the selected component and the input and output data of the normal input/output data 121*b* exceeds the allowable error, the malfunctioning component determiner 148 may determine that the selected component operates abnormally. The predetermined value may vary depending on the kinds of components, and may have been set in advance according to the kind or specification of the controlled medical device 1000 when the controlled medical device 1000 was manufactured or designed.

Hereinafter, an exemplary embodiment of a method of determining whether the controlled medical device 1000 operates abnormally, through a reference medical device, will be described with reference to FIGS. 29 to 35.

Figure 29:
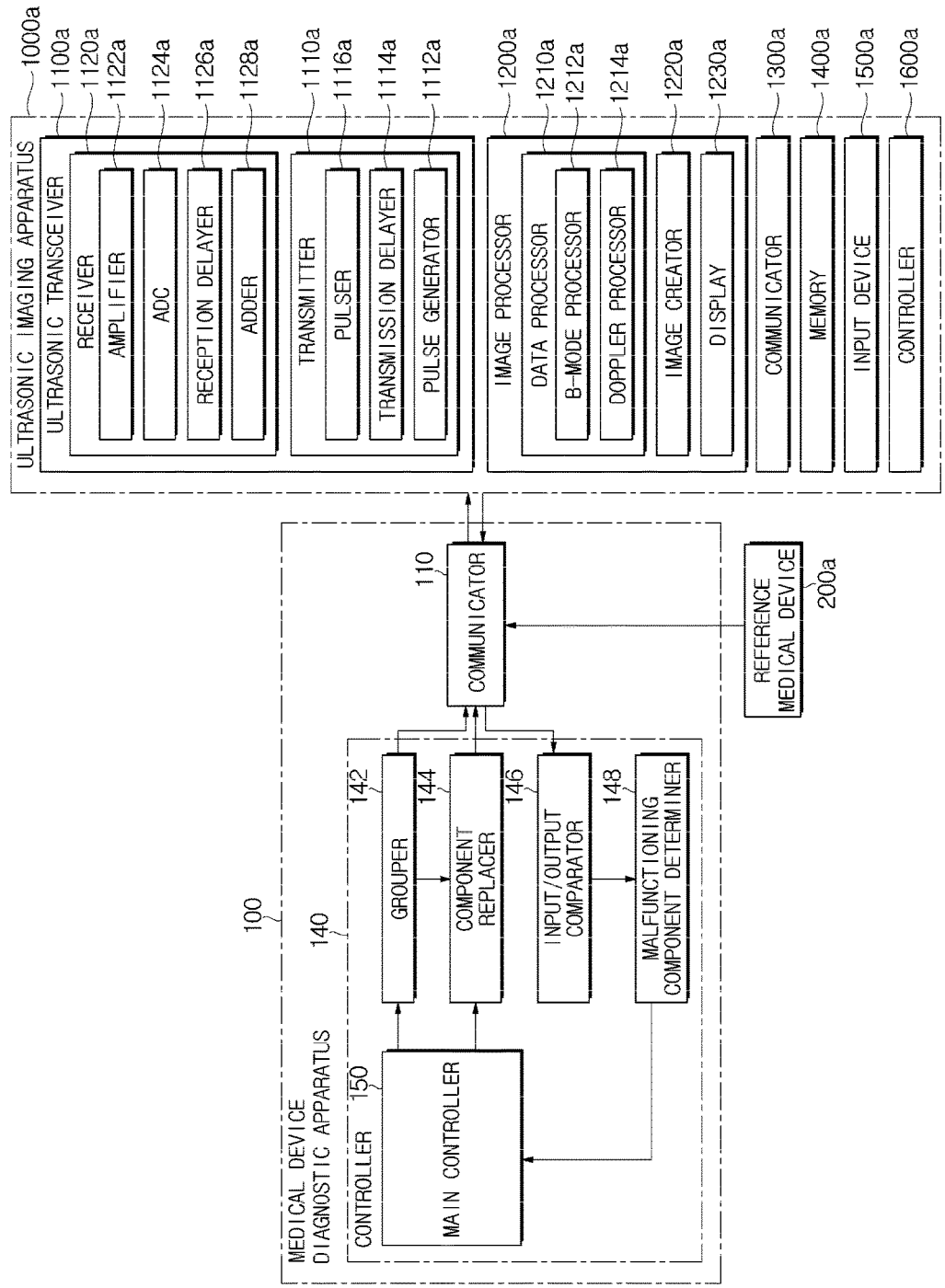
FIG. 29 is a block diagram of a medical device diagnostic apparatus when a controlled medical device is an ultrasonic imaging apparatus, according to another exemplary embodiment.
Figure 30:
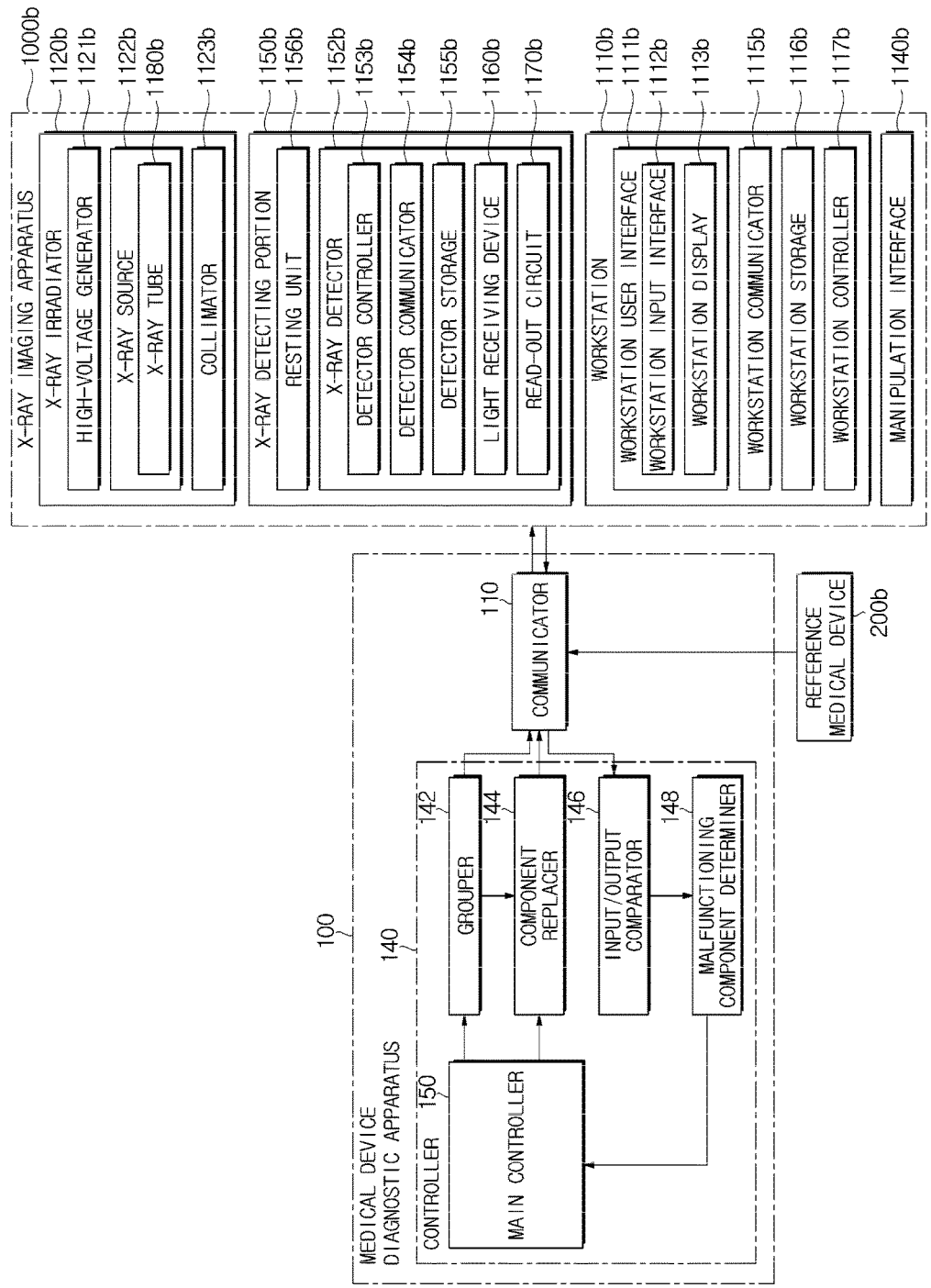
FIG. 30 is a block diagram of the medical device diagnostic apparatus when a controlled medical device is an X-ray imaging apparatus, according to another exemplary embodiment.
Figure 31:
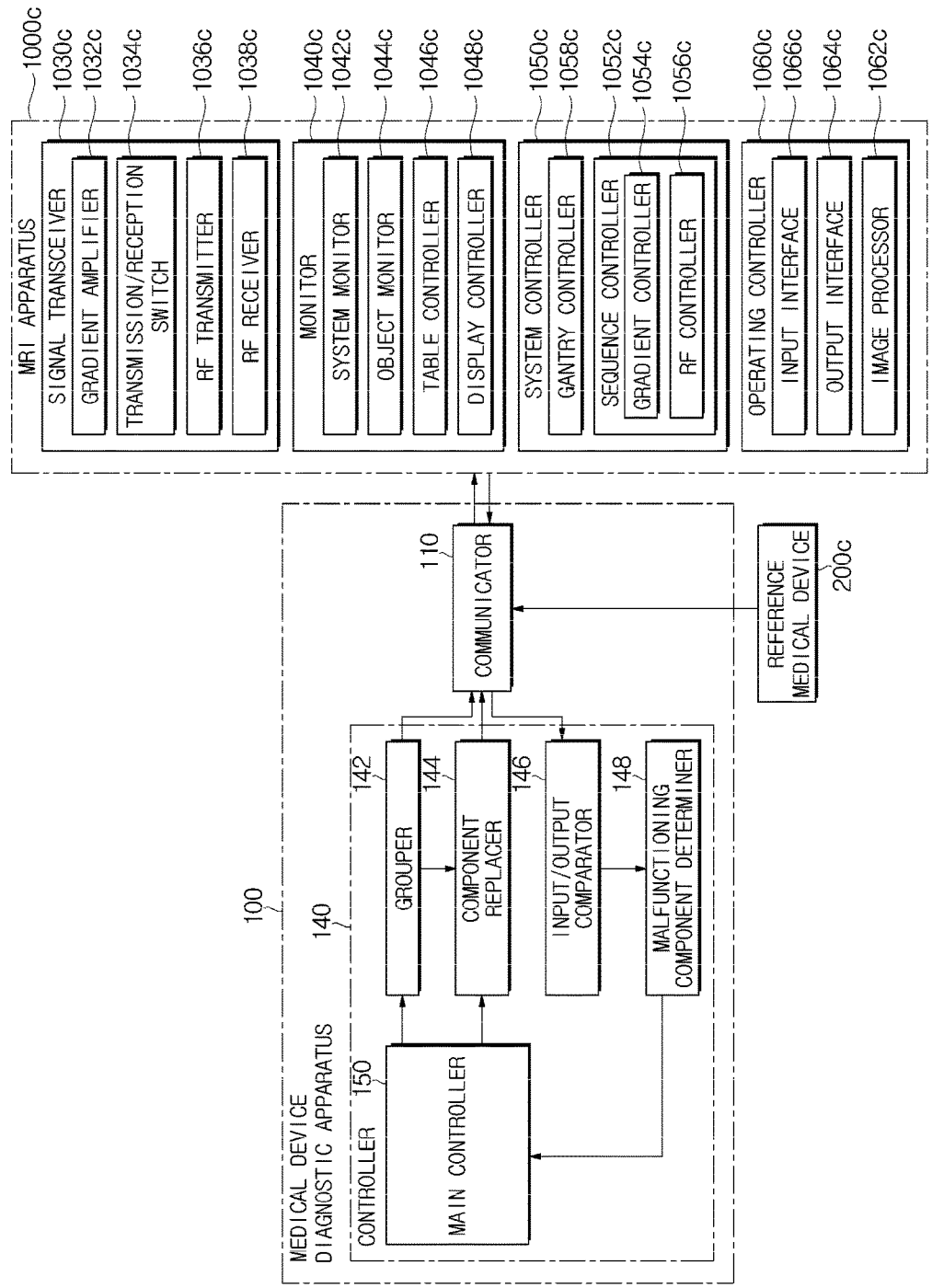
FIG. 31 is a block diagram of the medical device diagnostic apparatus when a controlled medical device is a MRI apparatus, according to another exemplary embodiment.
Figure 32:
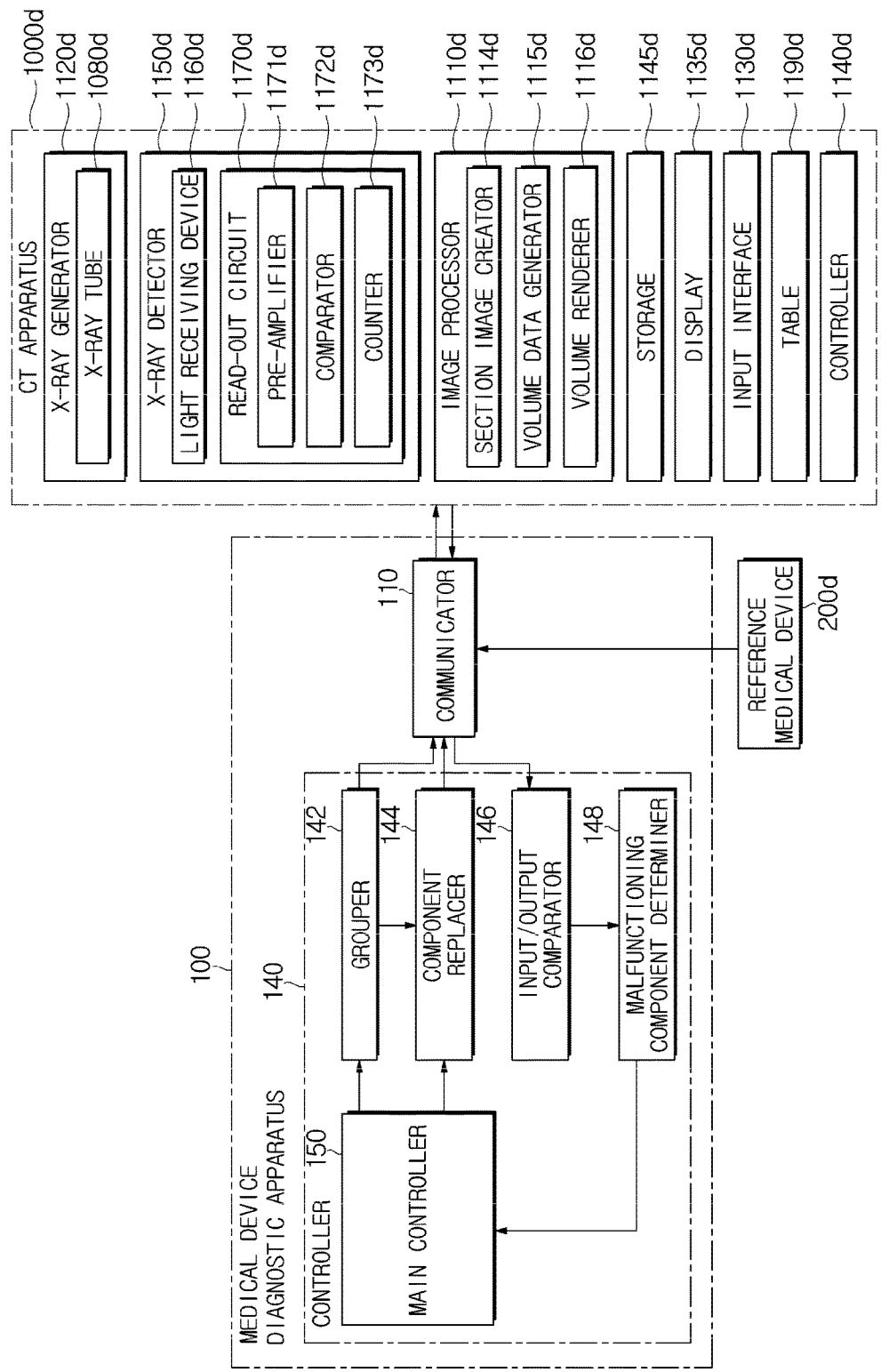
FIG. 32 is a block diagram of the medical device diagnostic apparatus when a controlled medical device is a CT apparatus, according to another exemplary embodiment.

FIG. 29 is a block diagram of the medical device diagnostic apparatus 100 when the controlled medical device 1000 is the ultrasonic imaging apparatus 1000*a*, FIG. 30 is a block diagram of the medical device diagnostic apparatus 100 when the controlled medical device 1000 is the X-ray imaging apparatus 1000*b*, FIG. 31 is a block diagram of the medical device diagnostic apparatus 100 when the controlled medical device 1000 is the MRI apparatus 1000*c*, and FIG. 32 is a block diagram of the medical device diagnostic apparatus 100 when the controlled medical device 1000 is the CT apparatus 1000*d*, according to exemplary embodiments.

Referring to FIGS. 29 to 32, the medical device diagnostic apparatus 100 may include the controller 140 and the communicator 110. The communicator 110 may be connected to the controlled medical device 1000, such as the ultrasonic imaging apparatus 1000*a*, the X-ray imaging apparatus 1000*b*, the MRI apparatus 1000*c*, and the CT apparatus 1000*d*, to perform data exchange between the medical device diagnostic apparatus 100 and the controlled medical device 1000.

The controller 140 may control operations of the medical device diagnostic apparatus 100.

As the controlled medical device 1000, the ultrasonic imaging apparatus 1000*a*, the X-ray imaging apparatus 1000*b*, the MRI apparatus 1000*c*, or the CT apparatus 1000*d* may be connected to the medical device diagnostic apparatus 100, as described above with reference to FIGS. 15 to 18.

Figure 33:
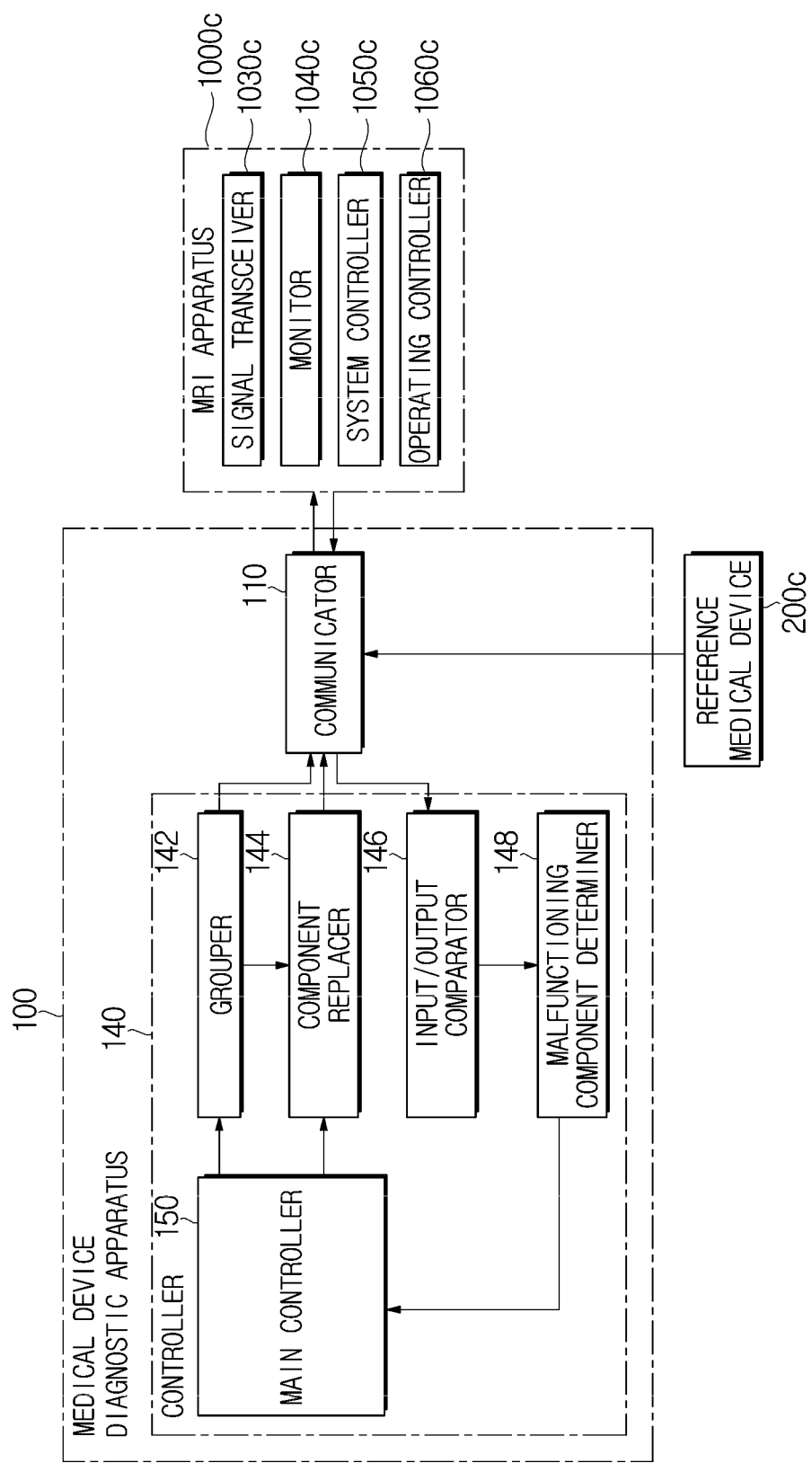
FIGS. 33, 34, and 35 are views illustrating a method in which the medical device diagnostic apparatus diagnoses a malfunction of controlled medical device, according to another exemplary embodiment.
Figure 34:
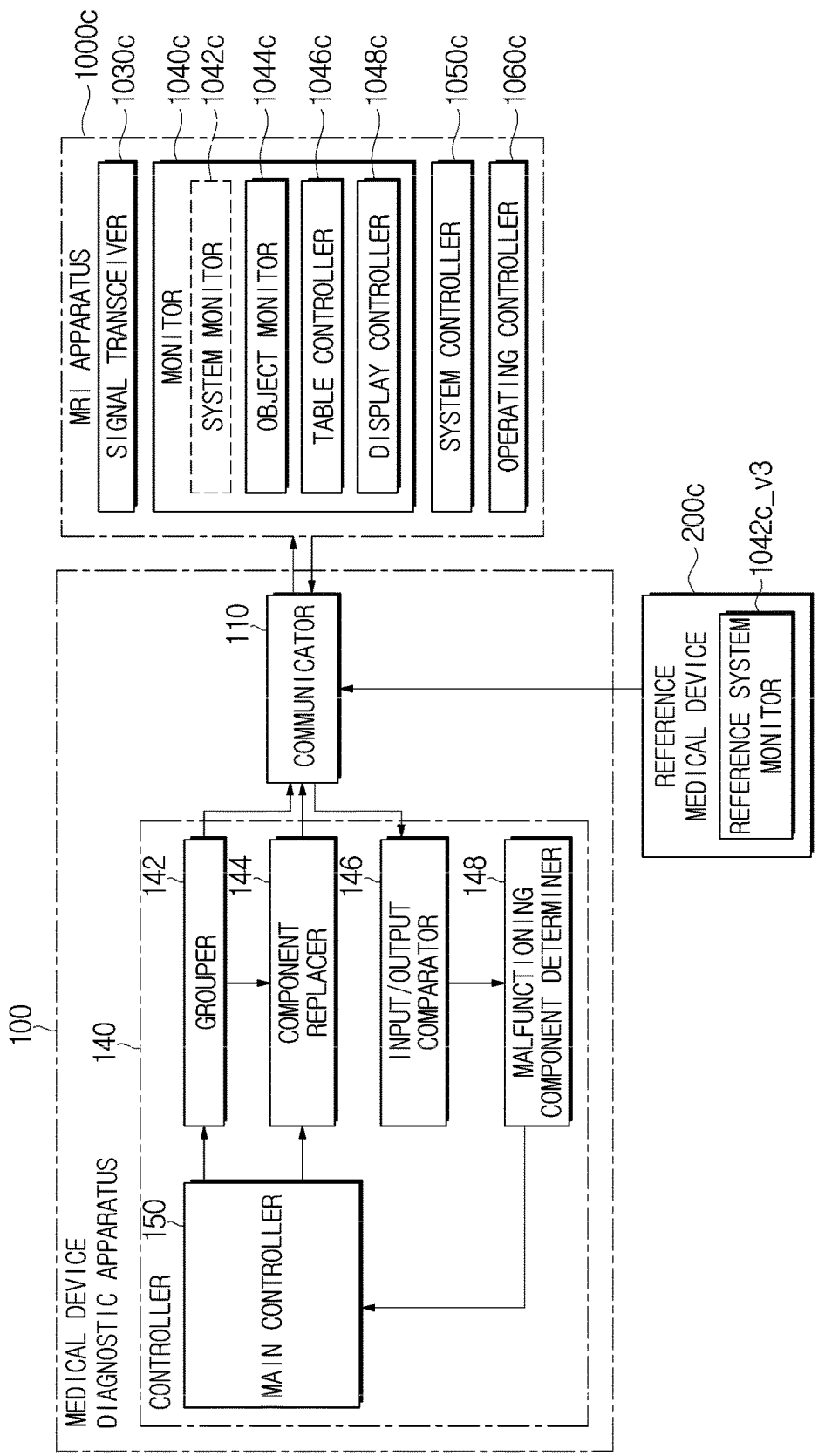
Figure 35:
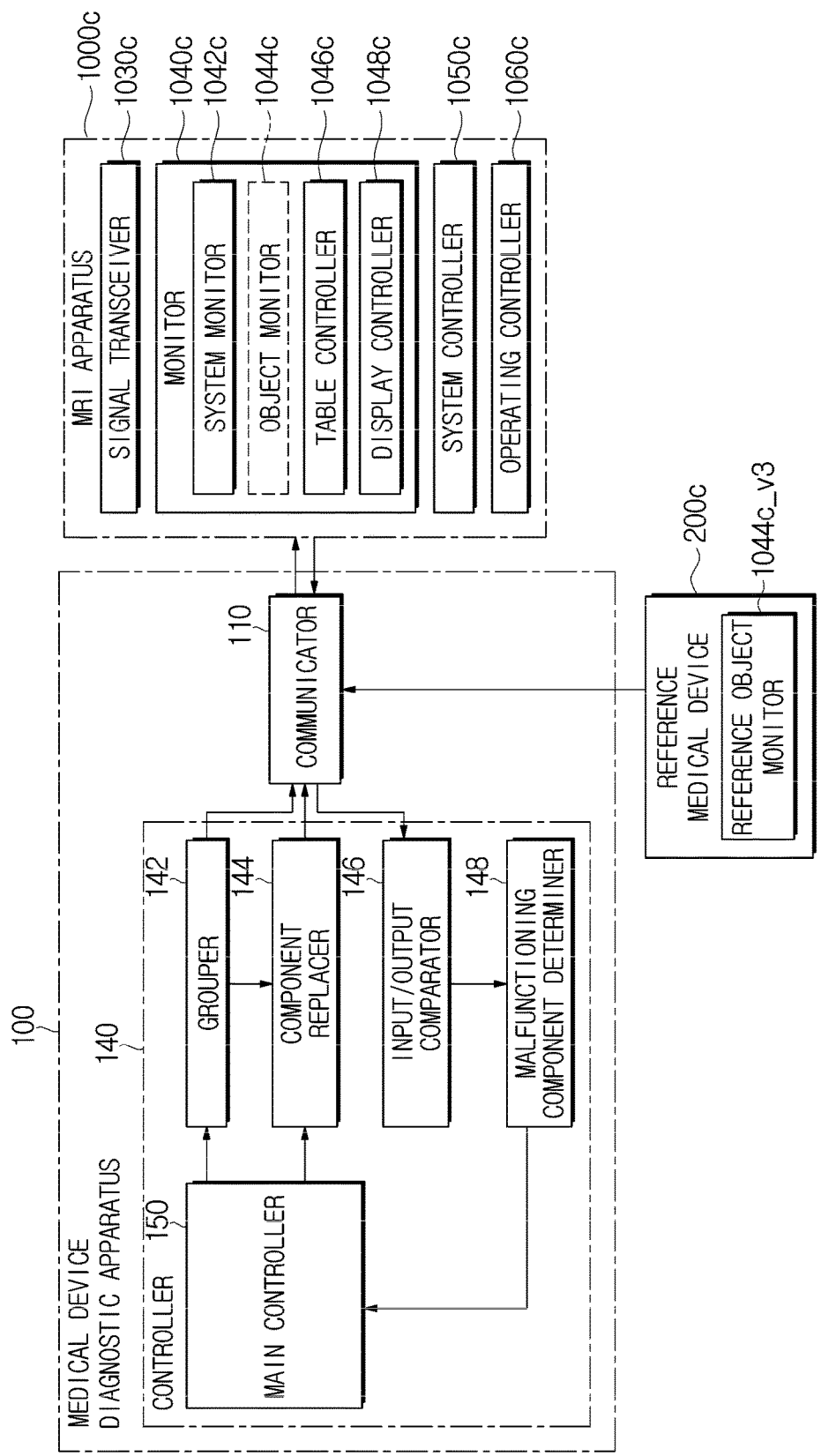

FIGS. 33, 34, and 35 are views illustrating a method in which the medical device diagnostic apparatus 100 diagnoses a malfunction of the controlled medical device 1000, according to an exemplary embodiment.

The medical device diagnostic apparatus 100 may include the communicator 110 and the controller 140.

The communicator 110 may be connected to the controlled medical device 1000 to transmit and receive data to and from the controlled medical device 1000. The communicator 110 may be the same as or different from the communicator 110 of FIG. 1.

The communicator 110 may be connected to a reference medical device 200 (200*a*, 200*b*, 200*c*, or 200*d*), as well as the controlled medical device 1000. The reference medical device 200 may be a medical device corresponding to the controlled medical device 1000 determined to operate normally. The reference medical device 200 may be connected to the communicator 110 of the medical device diagnostic apparatus 100 by a wire or wirelessly. Accordingly, the reference medical device 200 may be provided in the same space where the controlled medical device 1000 is placed or in different space from where the controlled medical device 1000 is placed.

The controller 140 may control operations of the medical device diagnostic apparatus 100. The controller 140 may include the main controller 150, the grouper 142, the component replacer 144, the input/output comparator 146, and the malfunctioning component determiner 148.

The main controller 150 may receive data about a plurality of components included in the controlled medical device 1000 through the communicator 110, and use the receive data to replace a component with data of the reference medical device 200. For example, the main controller 150 may receive information about a plurality of components included in the MRI apparatus 1000*c* from the MRI apparatus 1000*c*, and transfer the received information to the grouper 142 and the component replacer 144 so that the grouper 142 groups the plurality of components included in the MRI apparatus 1000*c*, and the component replacer 144 replaces a component included in the MRI apparatus 1000*c*.

The grouper 142 may group the plurality of components included in the controlled medical device 1000. If the controlled medical device 1000 is the MRI apparatus 1000*c*, the grouper 142 may set the signal transceiver 1030*c*, the monitor 1040*c*, the system controller 1050*c*, and the operating controller 1060*c* to upper components, set the gradient amplifier 1032*c*, the transmission/reception switch 1034*c*, the RF transmitter 1036*c*, and the RF receiver 1038*c* to lower components of the signal transceiver 1030*c*, set the system monitor 1042*c*, the object monitor 1044*c*, the table controller 1046*c*, and the display controller 1048*c* to lower components of the monitor 1040*c*, set the gantry controller 1058*c* and the sequence controller 1052*c* to lower components of the system controller 1050*c*, and set the input interface 1066*c*, the output interface 1064*c*, and the image processor 1062*c* to lower components of the operating controller 1060*c*.

After the grouper 142 decides the upper components and the lower components, the controller 140 may replace the upper components with data corresponding to the upper components in the reference medical device 200, and then determine whether the MRI apparatus 1000*c* operates normally. Also, if the controller 140 determines that an upper component operates abnormally, the controller 140 may replace lower components included in the corresponding upper component with data corresponding to the lower components in the reference medical device 200, and determine whether the MRI apparatus 1000*c* operates normally.

For example, as shown in FIG. 33, the controller 140 may replace the signal transceiver 1030*c*, the monitor 1040*c*, the system controller 1050*c*, and the operating controller 1060*c* with the corresponding components of the reference medical device 200*c*, and then determine whether the MRI apparatus 1000*c* operates normally. If the controller 140 determines that the monitor 1040*c* operates abnormally, the controller 140 may replace each of the system monitor 1042c, the object monitor 1044c, the table controller 1046c, and the display controller 1048c, which are the lower components of the monitor 1040c, with the corresponding component of the reference medical device 200c, and then determine whether the MRI apparatus 1000c operates normally.

The component replacer 144 may select one of the plurality of components included in the controlled medical device 1000, or a plurality of upper components or a plurality of lower components included in the controlled medical device 1000. The component replacer 144 may electrically separate the selected component(s) from the controlled medical device 1000, replace the selected component(s) with a component(s) corresponding to the selected component(s) among the components included in the reference medical device 200c, and then drive the controlled medical device 1000.

For example, as shown in FIG. 34, if it is determined that the monitor 1040c among the upper components included in the MRI apparatus 1000c operates abnormally, the component replacer 144 may select the system monitor 1042c among the lower components of the monitor 1040c. Then, the component replacer 144 may load data about components of the reference medical device 200c, replace the system monitor 1042c with a reference system monitor 1042c_v3 corresponding to the system monitor 1042c in the reference medical device 200c, and then drive the MRI apparatus 1000c.

If the input/output comparator 146 and the malfunctioning component determiner 148, which will be described later, determine that the system monitor 1042c operates normally, the component replacer 144 may select another component among the lower components of the monitor 1040c. That is, the component replacer 144 may select the object monitor 1044c that has not been selected among the lower components of the monitor 1040c, as shown in FIG. 35. Then, the component replacer 144 may load data of the reference medical device 200c, replace the object monitor 1044c with a reference object monitor 1044c_v3 corresponding to the object monitor 1044c among the components of the reference medical device 200c, and then drive the MRI apparatus 1000c.

The input/output comparator 146 may read input and output data of a component selected among the plurality of components included in the controlled medical device 1000, compare the read input and output data to input and output data corresponding to the selected component among the components of the reference medical device 200c, and then transfer the result of the comparison to the malfunctioning component determiner 148.

For example, the input/output comparator 146 may read input and output data of the object monitor 1044c, calculate a difference between the input and output data of the object monitor 1044c and input and output data of the reference object monitor 1044c_v3 corresponding to the object monitor 1044c among the components of the reference medical device 200c, and transfer the difference to the malfunctioning component determiner 148, as shown in FIG. 35.

Operation in which the component replacer 144 loads reference data, and operation in which the input/output comparator 146 reads input and output data of a component of the controlled medical device 1000 and input and output data of reference data may be performed using Equation (1) defined above.

The malfunctioning component determiner 148 may determine whether the selected component operates abnormally, based on the result of the comparison between the input and output data of the selected component and the input and output data corresponding to the selected component among the components of the reference medical device 200c.

The malfunctioning component determiner 148 may recognize the selected component based on the device ID, and determine whether the selected component operates abnormally, based on the difference between the input and output data of the selected component and the input and output data of the reference medical device 200c, the difference acquired by the input/output comparator 146.

For example, if the malfunctioning component determiner 148 determines that the difference between the input and output data of the selected component and the input and output data of the corresponding component included in the reference medical device 200c is greater than a predetermined value, the malfunctioning component determiner 148 may determine that the selected component operates abnormally. If the malfunctioning component determiner 148 determines that the difference between the input and output data of the selected component and the input and output data of the corresponding component included in the reference medical device 200c is smaller than or equal to the predetermined value, the malfunctioning component determiner 148 may determine that the selected component operates normally. Here, the predetermined value may be an allowable error between an input and an output when the selected component operates normally. If the difference between the input and output data of the selected component and the input and output data of the corresponding component included in the reference medical device 200c exceeds the allowable error, the malfunctioning component determiner 148 may determine that the selected component operates abnormally. The predetermined value may vary depending on the kinds of components, and may have been set in advance according to the kind or specification of the controlled medical device 1000 when the controlled medical device 1000 was manufactured or designed.

Figure 36:
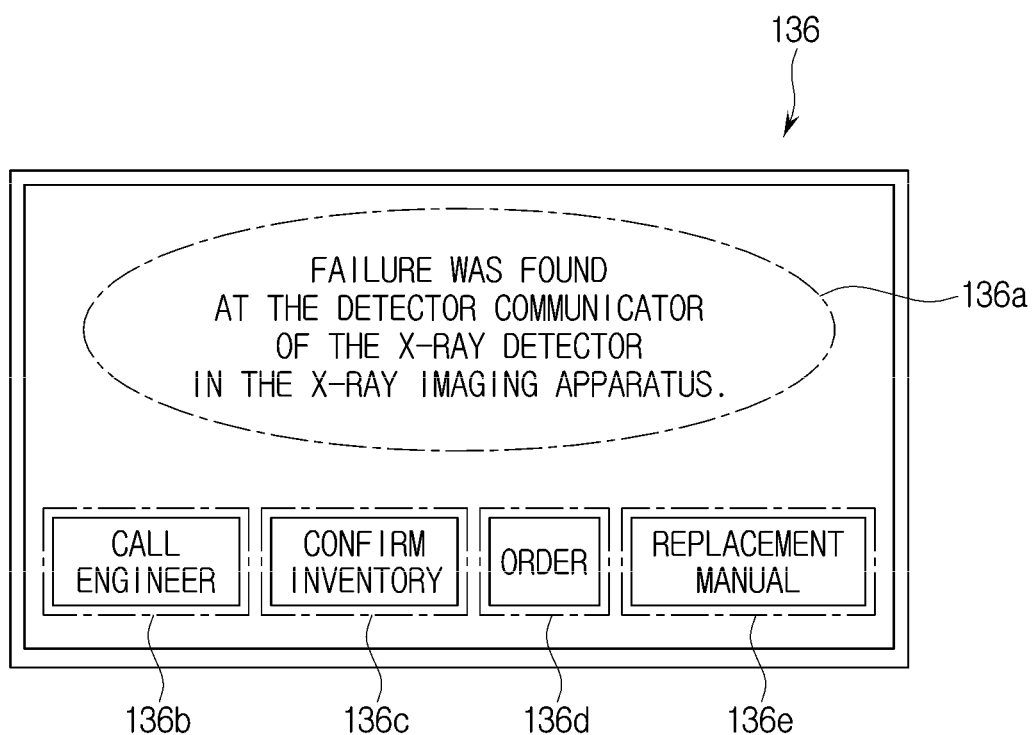
FIG. 36 is a screen that is displayed on a user interface, according to an exemplary embodiment.

FIG. 36 is a screen that is displayed on a user interface, according to an exemplary embodiment.

If it is determined that at least one of components included in a controlled medical device with a controller operates abnormally, the display 136 may display the corresponding component included in the controlled medical device, and display one or more input buttons to allow a user to call an engineer, to confirm the corresponding component in stock, to order the corresponding component, or to select a manual for replacing the corresponding component with a new one.

For example, if a controlled medical device connected to a medical device diagnostic apparatus is an X-ray imaging apparatus, the display 136 may display text "failure was found at the detector communicator of the X-ray detector in the X-ray imaging apparatus" as a malfunctioning component display image 136a. The display 136 may display an engineer call image 136b for repairing the X-ray imaging apparatus, an inventory image 136c for confirming an X-ray detector or a detector communicator in stock, an order image 136d for ordering an X-ray detector or a detector communicator, and a replacement manual image 136e to guide a user to replace an X-ray detector or a detector communicator with a new one.

If the user selects any one of the engineer call image 136b, the inventory image 136c, the order image 136d, and the replacement manual image 136e, the controller can execute the corresponding function through component order data or a self-replacement manual stored in a storage.

Figure 37:
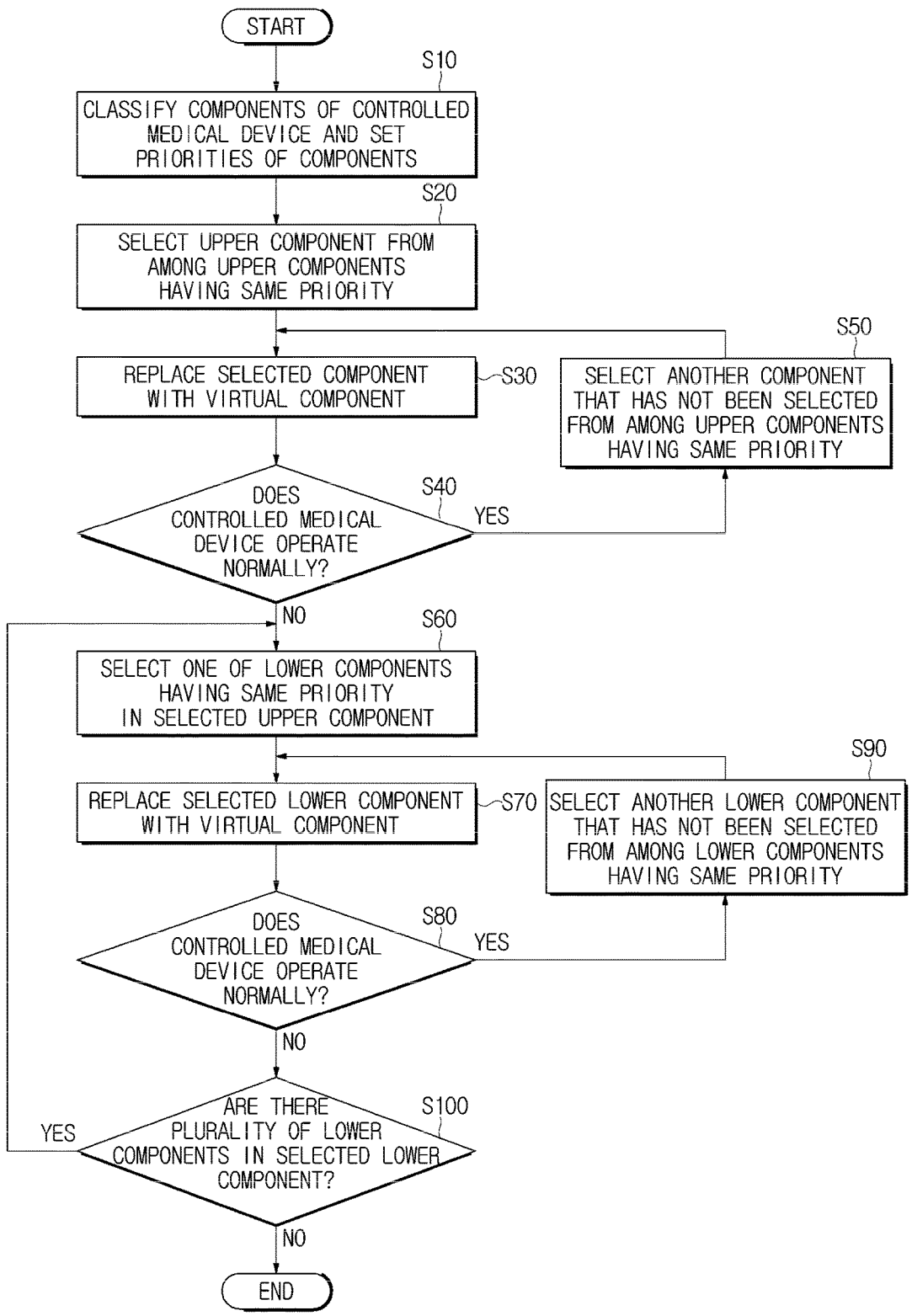
FIG. 37 is a flowchart illustrating a method in which a medical device diagnostic apparatus determines an abnormal operation of a controlled medical device, according to an exemplary embodiment.

FIG. 37 is a flowchart illustrating a method in which the medical device diagnostic apparatus determines an abnormal operation of a controlled medical device, according to an exemplary embodiment.

In operation S10, a grouper may classify a plurality of components of the controlled medical device, and set priorities of the classified components. In operation S20, a component replacer may select an upper component from among a plurality of upper components having the same priority. In operation S30, the component replacer may replace the selected component with a virtual component based on reference data.

In operation S40, an input/output comparator and a malfunctioning component determiner may determine whether the selected component included in the controlled medical device or the controlled medical device operates normally. If the input/output comparator and the malfunctioning component determiner determine that the selected component included in the controlled medical device or the controlled medical device operates normally, the method continues in operation S50. Otherwise, the method continues in operation S60.

In operation S50, the component replacer may select another component that has not been selected from among the upper components having the same priority, and the method returns to operations S30 to S40.

In operation S60, the component replacer may select one of lower components having the same priority in the selected upper component. In operation S70, the component replacer may replace the selected lower component with a virtual component based on the reference data.

In operation S80, the input/output comparator and the malfunctioning component determiner 148 may determine whether the selected lower component included in the selected upper component or the selected upper component operates normally. If the input/output comparator and the malfunctioning component determiner determine that the selected lower component included in the selected upper component or the selected upper component operates normally, the method continues in operation S90. Otherwise, the method continues in operation S100.

In operation S90, the component replacer may select another lower component that has not been selected from among the lower components having the same priority, and the method returns to operations S70 and S80.

In operation S100, a main controller may determine whether there are a plurality of lower components in the selected lower component. If the main controller determines that there are a plurality of lower components in the selected lower component, the method returns to operations S60 to S80. If the main controller determines that there is no lower component in the selected lower component, the main controller may control the display to display the result of diagnosis on the controlled medical device, and then terminate operation of the medical device diagnostic apparatus.

According to the medical device diagnostic apparatus and the control method thereof as described above, by replacing a component suspected as a malfunctioning component with a virtual component corresponding to the malfunctioning component without actually replacing the malfunctioning component with a new one, it is possible to accurately determine a component suspected as a malfunctioning component.

The foregoing exemplary embodiments and advantages are exemplary and are not to be construed as limiting. The present teaching may be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A medical device diagnostic apparatus comprising:
a communicator connected to a controlled medical device, the communicator being configured to transmit and receive data to and from the controlled medical device; and
a controller configured to:
select one of first components of the controlled medical device, based on the received data;
calculate a first difference value between first input and output data of the selected one of the first components and second input and output data corresponding to the selected one of the first components in reference data;
determine whether the first difference value is greater than a value;
based on the first different value being determined to be greater than the value:
determine that the selected one of the first components operates abnormally;
select one of second components included in the one of the first components determined to operate abnormally;
calculate a second difference value between third input and output data of the selected one of the second components and fourth input and output data corresponding to the selected one of the second components in the reference data;
determine whether the second difference value is greater than the value; and
based on the second different value being determined to be greater than the value, determine that the selected one of the second components operates abnormally; and
based on the first different value being determined to be less than or equal to the value, select another one of the first components, based on the received data, to determine whether the selected other one of the first components operates abnormally.

2. The medical device diagnostic apparatus according to claim 1, wherein the reference data is a medical device simulation corresponding to the controlled medical device.

3. The medical device diagnostic apparatus according to claim 1, further comprising a storage configured to store normal input and output data being inputs and outputs of the first components,
wherein the reference data is the normal input and output data.

4. The medical device diagnostic apparatus according to claim 1, wherein the communicator is connected to an external reference medical device corresponding to the controlled medical device, the external reference medical device operating normally, and
the communicator is further configured to receive the reference data from the external reference medical device.

5. The medical device diagnostic apparatus according to claim 1, further comprising a user interface configured to:
display a state of the controlled medical device; and
receive a diagnosis command.

6. The medical device diagnostic apparatus according to claim 1, further comprising a user interface configured to:
    display the first components; and
    receive an input selection of the one of the first components to determine whether the selected one of the first component operates abnormally.

7. The medical device diagnostic apparatus according to claim 1, wherein the controller is further configured to randomly select the one of the first components, the selected one of the first components having not been subject to determination on whether the selected one of the first components operates abnormally.

8. The medical device diagnostic apparatus according to claim 1, further comprising a user interface configured to display an inventory of the one of the first components determined to operate abnormally.

9. The medical device diagnostic apparatus according to claim 8, wherein the communicator is further configured to order the one of the first components of which the inventory is displayed.

10. The medical device diagnostic apparatus according to claim 1, further comprising:
    a storage configured to store a self-replacement manual for replacing the one of the first components determined to operate abnormally; and
    a user interface configured to display a method of replacing the one of the first components determined to operate abnormally, based on the self-replacement manual.

11. The medical device diagnostic apparatus according to claim 1, wherein the communicator is further configured to receive data for updating the reference data, from a server.

12. A method of controlling a medical device diagnostic apparatus, the method comprising:
    transmitting and receiving data to and from a controlled medical device;
    selecting one of first components of the controlled medical device, based on the received data;
    calculating a first difference value between first input and output data of the selected one of the first components and second input and output data corresponding to the selected one of the first components in reference data;
    determining whether the first difference value is greater than a value;
    based on the first different value being determined to be greater than the value:
        determining that the selected one of the first components operates abnormally;
        selecting one of second components included in the one of the first components determined to operate abnormally;
        calculating a second difference value between third input and output data of the selected one of the second components and fourth input and output data corresponding to the selected one of the second components in the reference data;
        determining whether the second difference value is greater than the value; and
        based on the second different value being determined to be greater than the value, determining that the selected one of the second components operates abnormally; and
    based on the first different value being determined to be less than or equal to the value, selecting another one of the first components, based on the received data, to determine whether the selected other one of the first components operates abnormally.

13. The method according to claim 12, wherein the reference data is a medical device simulation corresponding to the controlled medical device.

14. The method according to claim 12, wherein the reference data is normal input and output data being inputs and outputs of the first components.

15. The method according to claim 12, further comprising receiving the reference data from an external reference medical device connected to and corresponding to the controlled medical device, the external reference medical device operating normally.

16. The method according to claim 12, further comprising:
    displaying the first components; and
    receiving an input selection of the one of the first components to determine whether the selected one of the first components operates abnormally.

17. The method according to claim 12, wherein the selecting the one of the first components comprises randomly selecting the one of the first components, the selected one of the first components having not been subject to determination on whether the selected one of the first components operates abnormally.

18. The method according to claim 12, further comprising displaying an inventory of the one of the first components determined to operate abnormally.

19. The method according to claim 18, further comprising ordering the one of the first components of which the inventory is displayed.

20. The method according to claim 12, further comprising displaying a method of replacing the one of the first components determined to operate abnormally, based on a self-replacement manual for replacing the one of the first components determined to operate abnormally.

21. The method according to claim 12, further comprising receiving data for updating the reference data, from a server.

* * * * *